US012746219B2

(12) United States Patent
Benny et al.

(10) Patent No.: US 12,746,219 B2
(45) Date of Patent: Sep. 29, 2026

(54) METHODS AND COMPOSITIONS FOR PREVENTING SKIN TOXICITIES CAUSED BY BIOLOGICAL TARGETED CANCER DRUGS

(71) Applicants: Hadasit Medical Research Services & Development Limited, Jerusalem (IL); Yissum Research Development Company of the Hebrew University of Jerusalem Ltd., Jerusalem (IL)

(72) Inventors: Ofra Benny, Mevasseret Zion (IL); Sharon Merims, Bat Hefer (IL); Yelena Mostinski, Kokhav Yair (IL)

(73) Assignees: Hadasit Medical Research Services & Development Limited, Jerusalem (IL); Yissum Research Development Company of the Hebrew University of Jersusalem Ltd.

( * ) Notice: Subject to any disclaimer, the term of this patent is extended or adjusted under 35 U.S.C. 154(b) by 1189 days.

(21) Appl. No.: 17/633,560

(22) PCT Filed: Aug. 12, 2020

(86) PCT No.: PCT/IL2020/050887

§ 371 (c)(1),
(2) Date: Feb. 7, 2022

(87) PCT Pub. No.: WO2021/028919

PCT Pub. Date: Feb. 18, 2021

(65) Prior Publication Data

US 2022/0296543 A1 Sep. 22, 2022

Related U.S. Application Data

(60) Provisional application No. 62/885,559, filed on Aug. 12, 2019.

(51) Int. Cl.
*A61K 31/17* (2006.01)
*A61K 9/51* (2006.01)
(Continued)

(52) U.S. Cl.
CPC ........... *A61K 31/17* (2013.01); *A61K 9/5153* (2013.01); *A61K 31/4436* (2013.01); *A61K 45/06* (2013.01); *A61P 17/00* (2018.01)

(58) Field of Classification Search
CPC .. A61K 31/17; A61K 9/5153; A61K 31/4436; A61K 45/06; A61K 31/136;
(Continued)

(56) References Cited

FOREIGN PATENT DOCUMENTS

| | | | |
|---|---|---|---|
| WO | 2006/074919 | A2 | 7/2006 |
| WO | 2019/016843 | A1 | 1/2019 |

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113 (Year: 1989).*

(Continued)

*Primary Examiner* — Renee Claytor
*Assistant Examiner* — Andrew P Lee
(74) *Attorney, Agent, or Firm* — JMB Davis Ben-David

(57) ABSTRACT

Provided are methods for inhibiting binding of systemically administered drugs to a target in the skin by topically administering materials prior to or concomitantly with administration of the systemic drugs.

4 Claims, 21 Drawing Sheets

(51) Int. Cl.
*A61K 31/4436* (2006.01)
*A61K 45/06* (2006.01)
*A61P 17/00* (2006.01)

(58) Field of Classification Search
CPC .. A61K 31/166; A61K 31/167; A61K 31/397; A61K 31/4035; A61K 31/422; A61K 31/4355; A61K 31/4375; A61K 31/4402; A61K 31/454; A61K 31/519; A61K 31/4365; A61K 2300/00; A61P 17/00; A61P 17/04; A61P 17/10; A61P 17/14
See application file for complete search history.

(56) References Cited

OTHER PUBLICATIONS

Ahmed et al., "Microwave Assisted Synthesis and Antimicrobial Activity of New Pyrazolo[5,1-c][1,2,4]triazines and Thieno[2,3-b]pyridine Derivatives", Jordan Journal of Chemistry, vol. 7, No. 4, Jan. 12, 2012, pp. 365-381.
Bakhite et al., "Fluorine-containing heterocycles: Part III. Synthesis of some new furo[2,3-b]-, pyrazolo [3,4-b]- and thieno[2,3-b]pyridines with anticipated biological activities", Arabian Journal of Chemistry, vol. 7, No. 6, Jun. 18, 2014, pp. 936-946.
Boone et al., "Impact and Management of Skin Toxicity Associated with Anti-Epidermal Growth Factor Receptor Therapy: Survey Results", Oncology, 2007, vol. 72, pp. 152-159.
Lacouture et al., "Toxic Side Effects of Targeted Therapies and Immunotherapies Affecting the Skin, Oral Mucosa, Hair, and Nails", Am J Clin Dermatol., Nov. 2018, vol. 19, pp. 31-39.
Lacouture et al., "Dermatologic Toxicity Occurring During Anti-EGFR Monoclonal Inhibitor Therapy in Patients With Metastatic Colorectal Cancer: A Systematic Review", Clin Colorectal Cancer, Jun. 2018, vol. 17, No. 2, pp. 85-96.
Database Registry [Online], Chemical Abstracts Service, Columbus, Ohio, US; Mar. 23, 2003 (Mar. 23, 2003), Database accession No. 500275-10-5; abstract.
Database Registry [Online], Chemical Abstracts Service, Columbus, Ohio, US; Jul. 19, 2010, Database accession No. 1232796-94-9; abstract.
Database Registry [Online], Chemical Abstracts Service, Columbus, Ohio, US; Jul. 19, 2010, Database accession No. 1232780-58-3; abstract.
Database Registry [Online], Chemical Abstracts Service, Columbus, Ohio, US; Jul. 16, 2010, Database accession No. 1232770-36-3; abstract.
Database Registry [Online], Chemical Abstracts Service, Columbus, Ohio, US; Oct. 27, 2009, Database accession No. 1190301-80-4, CAS Registry Nos. 1190247-50-7, 1190247-48-3; abstract.
Database Registry [Online], Chemical Abstracts Service, Columbus, Ohio, US; Aug. 16, 2007, Database accession No. 944769-58-8; abstract.
Database Registry [Online], Chemical Abstracts Service, Columbus, Ohio, US; Dec 10, 2003, Database accession No. 625377-72-2, CAS Registry Nos. 625377-71-1, 625377-67-5, 625377-34-6; abstract.
Database Registry [Online], Chemical Abstracts Service, Columbus, Ohio, US; Oct. 29, 2003, Database accession No. 610259-29-5; abstract.
Database Registry [Online], Chemical Abstracts Service, Columbus, Ohio, US; Feb. 12, 2003, Database accession No. 488824-65-3; abstract.
Database Registry [Online], Chemical Abstracts Service, Columbus, Ohio, US; Nov. 19, 2001, Database accession No. 370869-65-1.
Database Registry [Online], Chemical Abstracts Service, Columbus, Ohio, US; Mar. 27, 2001, Database accession No. 329057-22-9; abstract.

* cited by examiner

METHODS AND COMPOSITIONS FOR PREVENTING SKIN TOXICITIES CAUSED BY BIOLOGICAL TARGETED CANCER DRUGS

TECHNOLOGICAL FIELD

The invention generally concerns methods of preventing and treating skin toxicities caused by systemically administrated drugs, such as anti-neoplastic kinase inhibitors and biologics such as monoclonal antibodies.

BACKGROUND

A great number of drugs administered systemically, among these are antineoplastic molecularly targeted agents, particularly those interfering with signal transduction (e.g., epidermal growth factor receptor [EGFR] inhibitors, mitogen activated protein kinase kinase [MEK] inhibitors), are known to be associated with prominent, and at times, dose-limiting dermatologic complications. To date treatment of skin toxicities caused by these drugs includes the use of topical steroids, antibiotics, skin moisturizers and sunscreens. Current treatment regimens do not show the efficacy needed, and as a result many of the patients undergoing treatment with such drugs require dose modification and interruptions of the anti-cancer treatment.

PUBLICATIONS

[1] Toxic Side Effects of Targeted Therapies and Immunotherapies Affecting the Skin, Oral Mucosa, Hair, and Nails. Mario Lacouture, Vincent Sibaud; Am J Clin Dermatol. 2018 November; 19:31-39.

[2] Dermatologic Toxicity Occurring During Anti-EGFR Monoclonal Inhibitor Therapy in Patients With Metastatic Colorectal Cancer: A Systematic Review. Mario E Lacouture, Milan Anadkat, Aminah Jatoi, Tamer Garawin, Chet Bohac, Edith Mitchell; Clin Colorectal Cancer. 2018 June; 17(2):85-96.

[3] Boone S L, Rademaker A, Liu D, Pfeiffer C, Mauro D J, Lacouture M E. Impact and management of skin toxicity associated with anti-epidermal growth factor receptor therapy: survey results. Oncology. 2007 72:152-9.

SUMMARY OF THE INVENTION

To overcome or at least reduce to a minimum dermatologic complications that impair quality of life of a very high percentage of patients treated with systemically administered drugs, or maintain an effective treatment with such drugs without needing to resort to dose reduction or regimen interruption, the inventors of the technology disclosed herein have explored a novel methodology that uses topical formulations to deliver a drug that is capable of arresting, preventing or reducing to a minimum skin toxicities associated with systemic delivery of drugs.

As known in the art, some steroids may be applied to the skin topically to prevent or diminish indirectly a skin effect of a systemically administered drug. Such agents act in a different fashion. Therefore, agents such steroids, antibiotics and vitamins, which effect on skin toxicities is not by direct blocking interaction between the systemic drugs with their targets, are excluded from the scope of the invention disclosed herein.

Topical corticosteroids bind to the cytoplasmic glucocorticoid receptor and are transported to the nucleus. The complex topical corticosteroid-glucocorticoid receptor binds to glucocorticoid response elements in the promoter region of a number of genes and modulates the transcription of a number of genes by inducing or inhibiting the transcription of specific mRNA and protein synthesis. Topical corticosteroids can also inhibit the activity of other transcription factors, including nuclear factor-kappa B (NFkB), activator protein 1 (AP-1), and nuclear factor of activated T cells (NFAT). These events lead to a series of local cellular effects, including the suppression of synthesis and release of prostaglandins and other inflammation mediators; release of the anti-inflammatory proteins (lipocortins, vasocortin, and vasoregulin); reduced release of inflammatory cytokines; inhibition of T cell activation; changes in the function of endothelial cells, granulocytes, mast cells, and Langerhans cells; and inhibition of mitotic activity of epidermal cells and dermal fibroblasts. Lipocortins inhibit phospholipase A2 and block release of arachidonic acid and platelet-activating factor (PAF) from cell membranes, thus preventing the formation of potent inflammation mediators, such as prostaglandins and leukotrienes (Gabros S, Zito P M. Topical corticosteroids. In: StatPearls, StatPearls Publishing, Treasure Island (FL) 2019; Sautebin L, Carnuccio R, Ialenti A, Di Rosa M. Lipocortin and vasocortin: two species of anti-inflammatory proteins mimicking the effects of glucocorticoids. Pharmacol Res 1992; 25:1; Oyanagui Y, Suzuki S. Vasoregulin, a glucocorticoid-inducible vascular permeability inhibitory protein. Agents Actions 1986; 17:270).

Thus, steroids are excluded from compounds administered topically to the skin according to the invention. However, steroids may be administered in combination with any of the compounds disclosed herein for topical administration to the skin.

Antibiotics such as tetracyclines, e.g., doxycycline and minocycline possess anti-inflammatory action in addition to the antibiotic action, and thus, used for the treatment of various skin disorders, including inflammatory acne, and neutrophilic dermatoses. Inhibition of lymphocyte activation and neutrophil chemotaxis is considered to be implicated in the anti-inflammatory action of tetracyclines. Moreover, it is known that both minocycline and doxycycline inhibit the production of interleukin-8 (IL-8), a proinflammatory cytokine, induced by the activation of protease-activated receptor 2 (PAR2) in normal human epidermal keratinocytes. Tetracyclines also reduce the potentiation by TNF-α or interleukin-1β of PAR2-mediated IL-8 production, in which minocycline is more potent than doxycycline (Sapadin A N, Fleischmajer R: Tetracyclines: nonantibiotic properties and their clinical implications. J Am Acad Dermatol 54: 258-265, 2006; Thong Y H, Ferrante A: Inhibition of mitogen-induced human lymphocyte proliferative responses by tetracycline analogues. Clin Exp Immunol 35: 443-446, 1979; shikawa C, Tsuda T, Konishi H, Nakagawa N, Yamanishi K: Tetracyclines modulate proteinase-activated receptor 2-mediated proinflammatory reactions in epidermal keratinocytes. Antimicrob Agents Chemother 53: 1760-1765, 2009).

Antibiotics are thus also excluded from compounds administered topically to the skin according to the herein disclosed invention. However, antibiotics may be administered in combination with any of the compounds disclosed herein for topical administration to the skin.

Without wishing to be bound by a specific mechanism of action, it is clear that the invention allows:

1) Improving the quality of life of patients suffering from skin toxicities associated with existing medical treatments-Current treatment alternatives available have seen limited impact on skin toxicities, with the majority of patients suffering from disabling rash and other visible skin conditions. The methodology of the invention permits effective management of such skin conditions, thereby maximizing benefit for patients.

2) Improving efficacy of skin therapy may further benefit patients by maintaining an optimal drug dosage and regimen, thereby allowing more patients to receive and comply with a treatment protocol.

The invention thus provides a methodology involving use of a topically administered drug to neutralize, inhibit, arrest, block, modulate or otherwise prevent or treat a skin side-effect associated with a drug administrated systemically. The topically administered drug may be administrated prior to commencement of a treatment regimen involving the systemic administration of a drug capable of or known to cause skin side-effects or may be administrated at any stage after said treatment commences.

As demonstrated hereinbelow, the proposed novel medical methodology is effective in conjunction with any medical treatment or prophylaxis that involves systemic administration of a drug capable of inducing skin side-effect or on target skin toxicity.

Targeted therapy or molecularly targeted therapy blocks the growth of cancer cells by interfering with specific targeted molecules needed for carcinogenesis and tumor growth, rather than by simply interfering with all rapidly dividing cells (e.g. with traditional chemotherapy). Because most agents for targeted therapy are biopharmaceuticals, the term biologic therapy is sometimes synonymous with targeted therapy when used in the context of cancer therapy (and thus distinguished from chemotherapy, that is, cytotoxic therapy).

Targeted cancer therapies are expected to be more effective than older forms of treatments and less harmful to normal cells. The most successful targeted therapies are chemical entities that target or preferentially target a protein or enzyme that carries a mutation or other genetic alteration that is specific to cancer cells and not found in normal host tissue. When the target is found in normal host tissue as in skin, this leads to "on target toxicity" as the systemic targeted anti-cancer drug binds and induces damage to the normal host tissue that share the same target as the tumor cells.

The drugs to be administered topically to a skin region of the subject, to neutralize toxicity caused by a systemically administered drug is selected from the following families of organic compounds:

1. Amine-containing compounds;
2. Pyridine-based compounds;
3. Pyrimidine-based compounds;
4. Aniline-based compounds;
5. Heteroaryl-containing compounds, or heterocyclyl-containing compounds, wherein the heteroaryl ring or heterocyclyl comprising between 1 and 3 heteroatoms selected from N, O and S;
6. Thieno pyridines;
7. Sulfonamides; and
8. Fluorinated aryls.

Thus, in a first aspect, the invention provides a method for arresting or inhibiting or interrupting or blocking binding of at least one systemically administered drug to its target in a skin or a skin appendage (keratinocytes, hair follicles, sebaceous glands, apocrine glands of skin, etc), the method comprising topically administering at least one material prior to or concomitantly with administration of the at least one systemically administered drug, to thereby arrest or inhibit or interrupt or block the binding of at least one systemically administered drug to the target in the skin.

The invention further provides a method for preventing or interrupting binding between at least one systemically administered drug and its target, the method comprising topically administering at least one material prior to or concomitantly with administration of the at least one systemically administered drug, to cause association of the at least one topically administered material to the target or to the at least one systemically administered drug, thereby preventing or interrupting or blocking binding of the at least one systemically administered drug to its target in the skin.

The invention further provides a method of reducing or diminishing at least one skin-side effect associated with a systemic administration of at least one drug, the method comprising topically administering at least one material prior to or concomitantly with the systemic administration of the at least one drug.

The invention further provides a method of permitting effective treatment by at least one systemically administered drug known to or capable of causing at least one skin toxicity, the method comprising topically administering at least one material prior to or concomitantly with systemic administration of the at least one drug.

Putting it differently, in a method for interrupting a binding of at least one systemically administered drug to its target in a skin region, the method comprising administering to the skin region at least one material prior to, concomitantly with or following the administration of the at least one systemically administered drug, to thereby arrest or inhibit or interrupt or block binding of at least one systemically administered drug to the target in the skin region. As noted herein, the term "interrupting" comprises arresting, inhibiting, diminishing, competing, reducing, preventing or blocking said binding.

In some embodiments, the invention further provides a method of preventing or treating a disease or disorder in a subject without causing or inducing skin toxicities, the method comprising:

prior to or concomitantly with administering to the subject at least one drug capable of preventing or treating the disease or disorder, topically administering at least one material capable of preventing skin toxicities in said subject, wherein said skin toxicities are induced by or associated with the at least one drug.

In some embodiments, in a method of preventing or treating a disease or disorder, the method comprising:

systemically administering at least one drug capable of inducing or causing skin toxicities;

prior thereto or concomitantly therewith topically administering at least one material capable of preventing or minimizing said skin toxicities.

As noted, the material administrated to a skin region is "administered topically". In other words, it is not administered in a way that delivers the material into the blood circulation. Without wishing to be bound by theory, the ability of the topically administered material to minimize or prevent toxicities associated with the systemically administrated drug may be due to any mechanism of action. Such a mechanism of action may include direct or indirect arrest or inhibition or interruption of binding of the systemically administered drug to its target, by competitive or non-competitive association of the topically administered material to the target and/or association of the topically administrated material to the systemically administered drug, to thereby prevent it from associating to its target and inducing a toxicity. Notwithstanding the particular mechanism of action, it would seem that without influencing systemic activity of the systemically administrated drug, skin toxicity is prevented. The effect of the topically administered material or drug is on the target site of the systemically administered drug, and thus the effect is direct.

The topically administered materials used in accordance with the invention are selected or configured not to penetrate through the skin layers into the blood system, or where penetration occurs it results in blood concentration that is negligible in affecting the activity of the systemically administrated drug. These materials exert their direct effect in skin localities onto which the materials are applied, and may thus be administrable neat or in a carrier or in a delivery vehicle, as known in the art. For specific toxicities, as in papulopustular rash, the topically administrable material is selected to target the follicular unit, while for other toxicities, such as paronychia, the material may be selected to target the nails and thus may be administrable neat or in any carrier or in a delivery vehicle that is capable of collecting or aggregating in the specific skin region. It is believed that the materials are collected or aggregated in hair follicles and potentially also in other skin folding or cavities or appendages.

The topically administrable materials may be formulated into a suitable formulation or composition known for cosmetic use or medicinal use. The carriers may be selected from powders, oils, creams, ointments, lotions, gels, pastes, mousiness, hydrogels or delivery systems such as liposome, niosome, microsponge, microemulsion, microsphere, SLN, aerosol and others. The materials may be effectively dispersed or suspended or solubilized in a liquid medium to form a solution, a suspension or a dispersion that may be applied topically, sprayed onto the skin or delivered by contact via the use of a sponge, a plaster, a pad or any skin dressing. For some applications, controlled release of the active cargo of such delivery systems may be essential.

Thus, in order to permit or allow collection of the topically administered material in hair follicles, and other skin appendages, the material may be encapsulated or carried in a nanoparticle or a microparticle of a selected form, a selected material and/or at a selected load.

The at least one topically administrable material may be in a nanoparticulate or a microparticulate form. In some embodiments, the at least one topically administrable material may be carried in a carrier selected from nanocapsules, nano-carriers, nanoparticles, microcapsules, micro-carriers and microparticles.

The material administered to the skin region may be administered prior to or together with the drug administered systematically. In cases where the two are administered together, the topical administration may continue as long as the systemic treatment is ongoing or to any period of time after the systemic treatment has been discontinued, i.e. 1, 2, 3, 4, 5, 6, 7, 8, 9 or 10 days after the systemic treatment has been discontinued, or 1, 2, 3, 4, 5, 6, 7, 8, 9, or 10 weeks after the systemic treatment has been discontinued. In cases where the material administered topically is administrated prior to the systemic treatment, topical treatment may begin 1, 2, 3, 4, 5, 6, 7, 8, 9 or 10 days before systemic treatment begins, or 1, 2, 3, 4, 5, 6, 7, 8, 9, or 10 weeks before systemic treatment begins.

The skin region onto which the material is topically administered may be any region of the human or animal skin that is affected by the systemically administered drug; namely any skin region which is expected to exhibit the skin toxicities associated with the drug. The skin region may be the whole skin of the subject or a skin of the face, chest back, scalp hands, legs nails, neck or shoulders; or any skin-associated structure, i.e., skin appendage such as hairs, arrector pilli, sebaceous glands, sweat glands and nails.

The topically administrable material is as disclosed herein. Excluded are topically administrable steroids, vitamins, antibiotics, skin moisturizers, sunscreens and topical BRAFi. However, such agents may be administered with a compound used according to the invention (in combination, one after the other or in the same regimen or session).

In some embodiments, the topically administered material is a compound herein designated LW11:

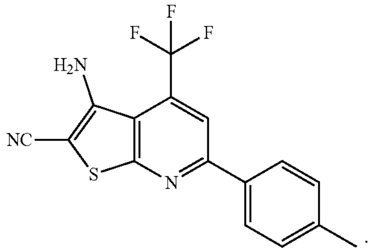 [SMILES: Cc1ccc(-c2cc(C(F)(F)F)c3c(N)c(C#N)sc3n2)cc1]

In some embodiments, the topically administered material is a compound herein designated G4:

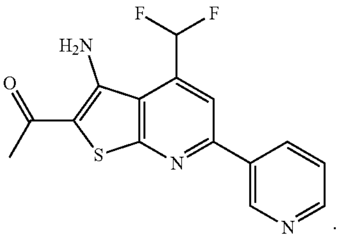 [SMILES: CC(=O)c1sc2nc(-c3cccnc3)cc(C(F)F)c2c1N]

In some embodiments, the topically administered material is a compound selected from:

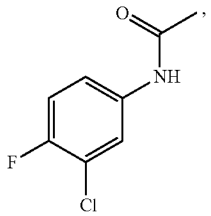

(herein designated compound SN-7)

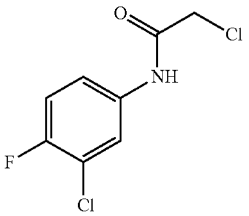

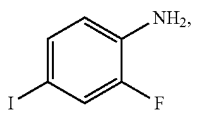

(herein designated compound SN-1)

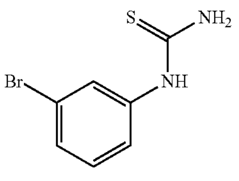

(herein designated compound SN-4)

-continued

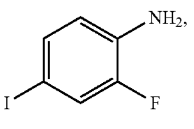

(herein designated compound SN-5)

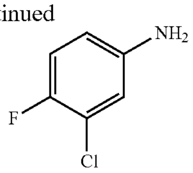

(herein designated compound SN-6)

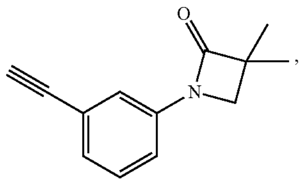

(herein designated compound SN-2)

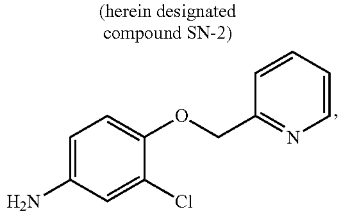

(herein designated compound SN-8)

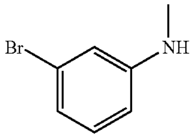

and (herein designated compound SN-3)

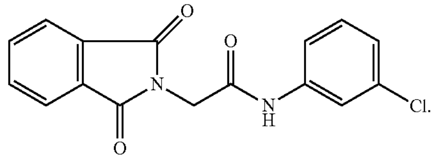

(herein designated compound SN-9)

In some embodiments, the topically administrable compound has a structure of the formula (I):

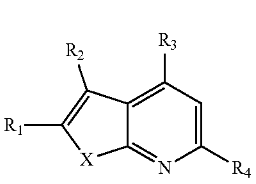

wherein

X is S or O;

each of R1, R2, R3 and R4, independently of the other, is selected from H, halide, —NR'R", —OH, —CN, —C(═NH)$NH_2$, —OC1-C5alkyl, —OC6-C10aryl, —OC5-C10heteroaryl, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5alkyl, —C1-C5haloalkyl, —C1-C5alkyl-C6-C10aryl, —C1-C5alkyl-C5-C10heteroaryl, —C6-C10aryl and —C5-C10heteroaryl, each of R' and R", independently of the other, may be H, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5alkyl, —C1-C5haloalkyl, —C1-C5alkyl-C6-C10aryl, —C1-C5alkyl-C5-C10heteroaryl, —C6-C10aryl and —C5-C10heteroaryl; or wherein R' and R" together with the N atom to which they are bonded form a cyclic moiety having between 2 and 6 carbon atoms.

In some embodiments, R1 is selected from —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5alkyl, —C1-C5haloalkyl, —C1-C5alkyl-C6-C10aryl, —C1-C5alkyl-C5-C10heteroaryl, —C6-C10aryl and —C5-C10heteroaryl.

In some embodiments, R1 is selected from —C(═O)C1-C5alkyl and —C(═O)NR'R", wherein each of R' and R" is selected as herein. In some embodiments, each of R' and R" is H. In some embodiments, R' and R" together with the N atom to which they are bonded form a cyclic moiety having between 2 and 6 carbon atoms. In some embodiments, R1 is —C(═O)OC1-C5alkyl, wherein the alkyl is a methyl or an ethyl. In some embodiments, R1 is a —C6-C10aryl and —C5-C10heteroaryl.

In some embodiments, R2 is selected from H, halide, —NR'R", —OH, —OC1-C5alkyl, —OC6-C10aryl, —C1-C5alkyl and —OC5-C10heteroaryl; and each of R' and R", independently of the other, may be H, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5alkyl, —C1-C5haloalkyl, —C1-C5alkyl-C6-C10aryl, —C1-C5alkyl-C5-C10heteroaryl, —C6-C10aryl and —C5-C10heteroaryl.

In some embodiments, R2 is —NR'R", wherein each of R' and R" is as defined herein.

In some embodiments, R2 is a primary amine, a secondary amine or a tertiary amine. In some embodiments, R2 is $NH_2$.

In some embodiments, R3 is selected from H, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5alkyl, —C1-C5haloalkyl, —C1-C5alkyl-C6-C10aryl, —C1-C5alkyl-C5-C10heteroaryl, —C6-C10aryl and —C5-C10heteroaryl.

In some embodiments, R3 is selected from —C1-C5alkyl, —C1-C5haloalkyl, —C1-C5alkyl-C6-C10aryl, —C1-C5alkyl-C5-C10heteroaryl, —C6-C10aryl and —C5-C10heteroaryl.

In some embodiments, R3 is H or a halogenated alkyl group.

In some embodiments, R3 is a fluorinated alkyl. In some embodiments, the fluorinated alkyl is —C1-C5haloalkyl, wherein the halo atom is fluorine. In some embodiments, the fluorinated alkyl is —$CH_2F$, —$CHF_2$ or —$CF_3$.

In some embodiments, R4 is selected from —C1-C5alkyl, —C1-C5haloalkyl, —C1-C5alkyl-C6-C10aryl, —C1-C5alkyl-C5-C10heteroaryl, —C6-C10aryl and —C5-C10heteroaryl, each of which may be substituted or provided in a fused form.

In some embodiments, R4 is selected from —C1-C5alkyl, —C1-C5alkyl-C6-C10aryl, —C1-C5alkyl-C5-C10heteroaryl, —C6-C10aryl and —C5-C10heteroaryl.

In some embodiments, R4 is selected from —C1-C5alkyl, —C1-C5alkyl-C6-C10aryl, —C1-C5alkyl-C5-C10heteroaryl, —C6-C10aryl and —C5-C10heteroaryl.

As used herein, a C1-C5alkyl is an aliphatic carbon-atom containing groups comprising between 1 and 5 carbon atoms. In some embodiments, the group is selected from methyl, ethyl, propyl, n-butyl, iso-butyl, tert-butyl, iso-pentyl, n-pentyl and others. Where the group is used to define a further group, such as in the case of —C1-C5alkyl-C6-C10aryl or —C1-C5alkyl-C5-C10heteroaryl, the group C1-C5alkyl denotes an alkylene group (e.g., methylene, ethylene, propylene, etc) that is bonded to a C6-C10aryl group or to a C5-C10heteroaryl group, respectively.

A fluorinated alkyl group or a haloalkyl is an alkyl group as defined, wherein one or more of the hydrogen atoms has been replaced with a fluorine atom or another halide atom. For example, where the alkyl is methyl, a fluorinated methyl may be selected from —$CH_2F$, —$CHF_2$ and —$CF_3$. A haloalkyl is defined in a similar fashion to include a bromine atom(s), a chloride atom(s) or an iodine atom(s).

A C6-C10aryl is an aromatic group containing between 6 and 10 carbon atoms. The group may contain a phenyl group that may be further substituted, a naphthyl group that is further substituted or any other aromatic group as defined.

The group —C5-C10heteroaryl is an aromatic group comprising between 5 and 10 carbon atoms and one or more heteroatoms selected from N, S and O.

In some embodiments, the topically administrable compound has a structure selected from:

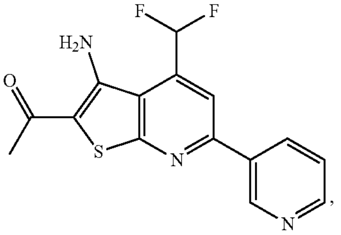

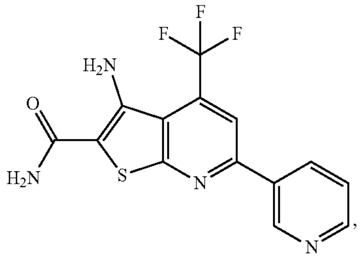

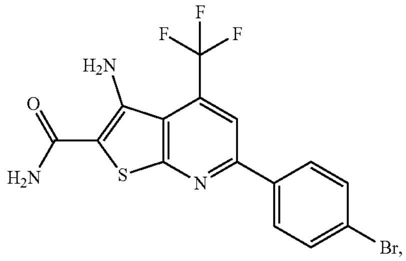

-continued

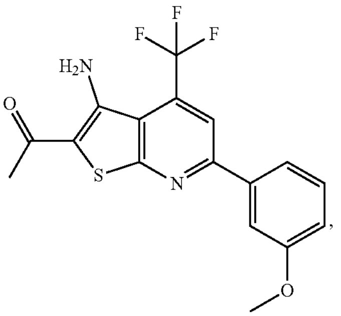

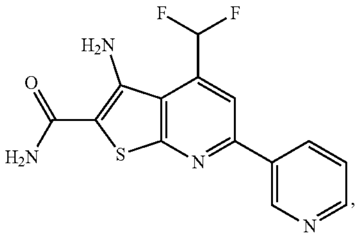

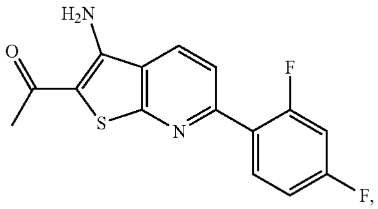

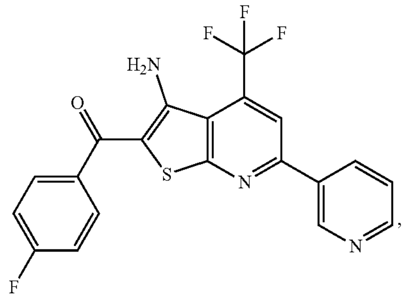

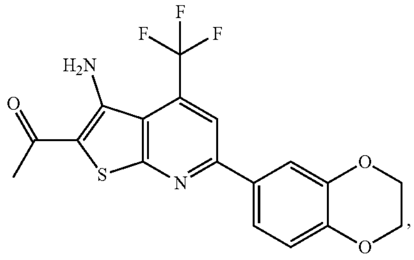

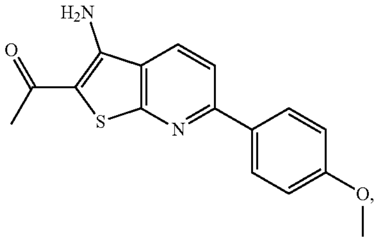

-continued
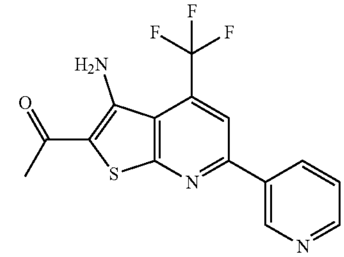,
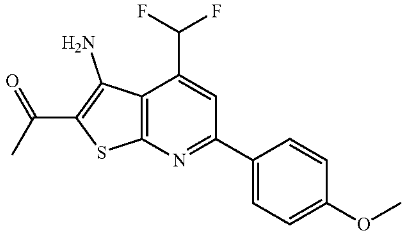,
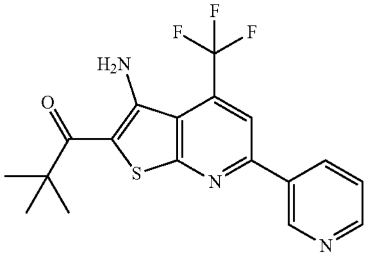,
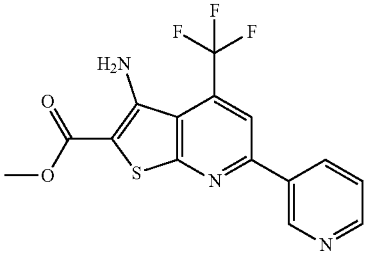,
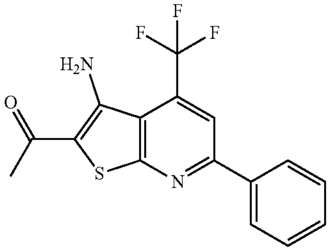,
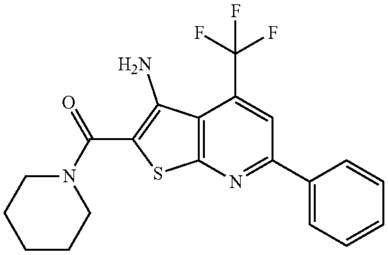,
-continued
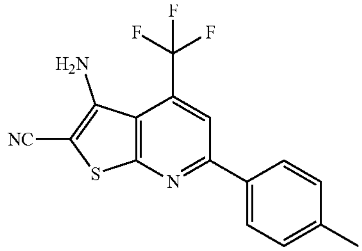,
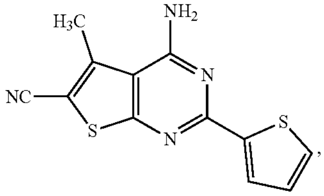,
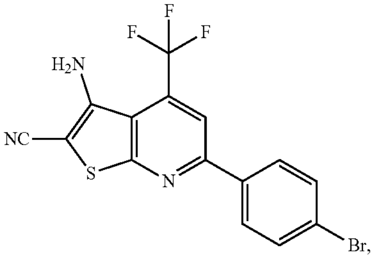,
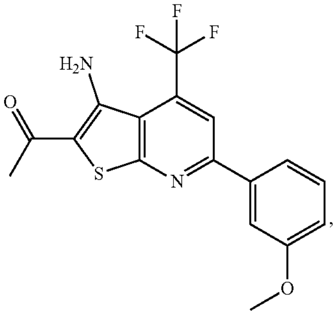,
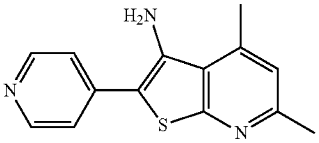,
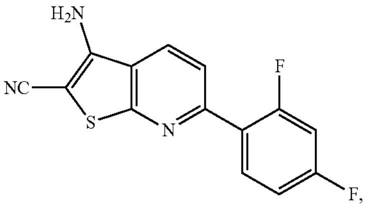,
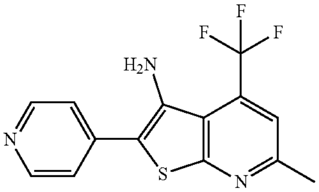, -continued
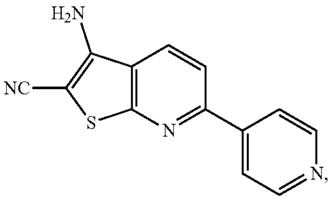,
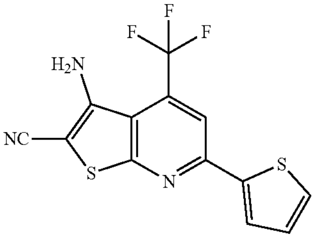
and
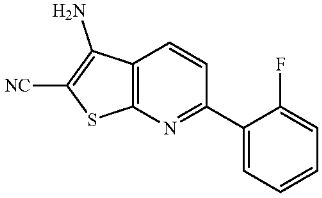.
In some embodiments, the topically administrable compound has a structure selected from:
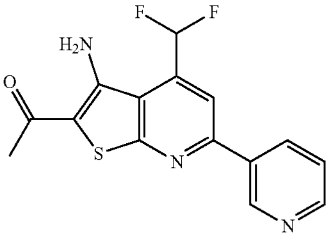,
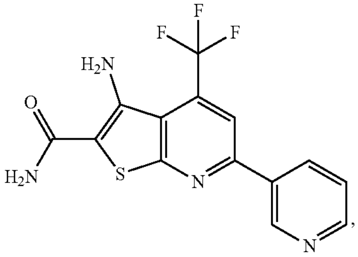,
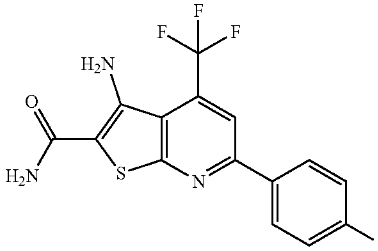,
-continued
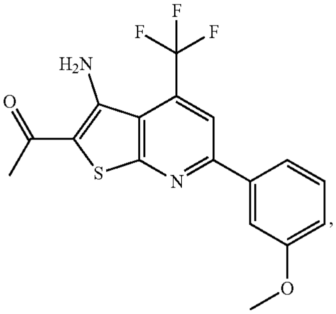,
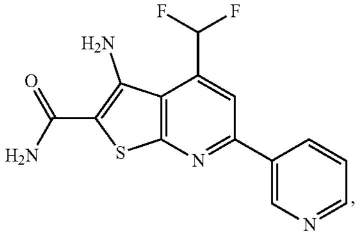,
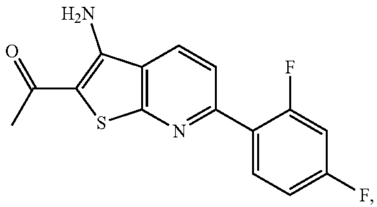,
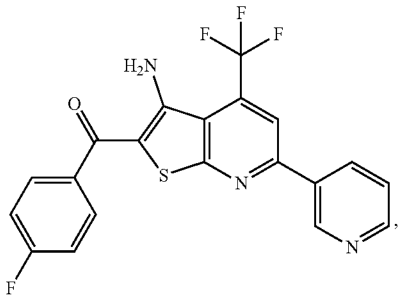,
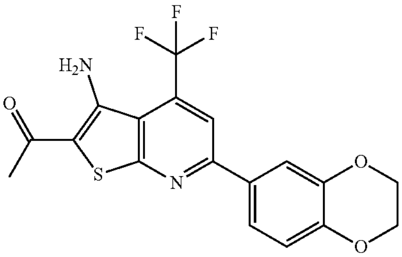,
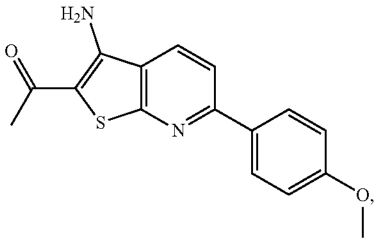, -continued
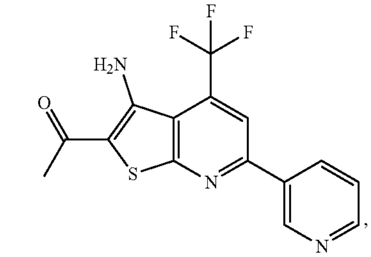,
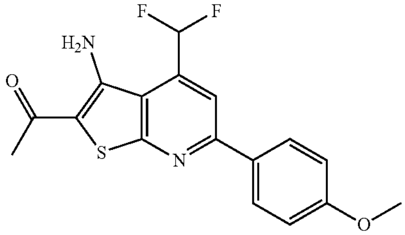,
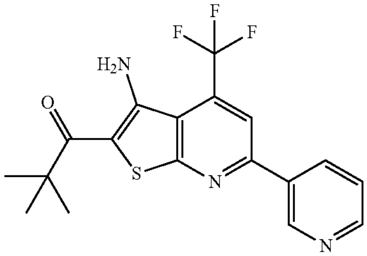,
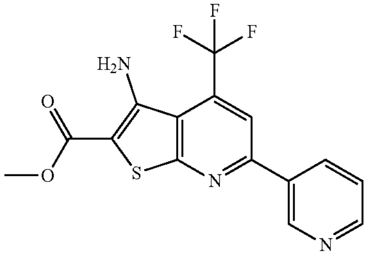,
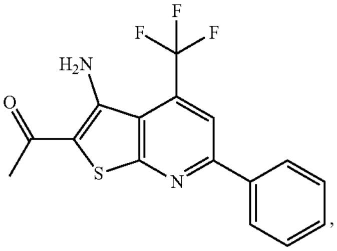,
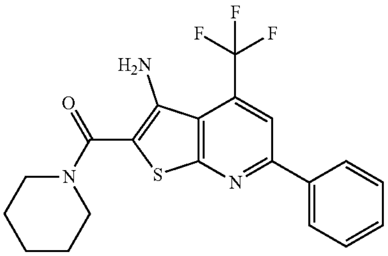,
-continued
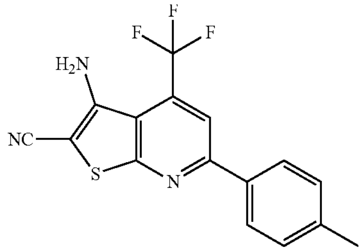,
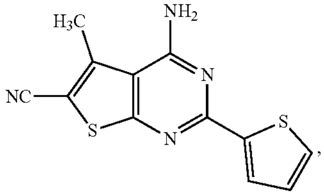,
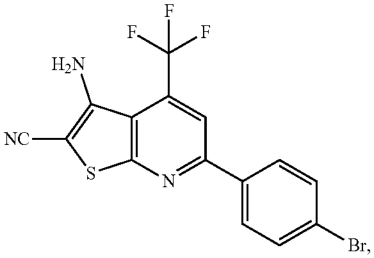,
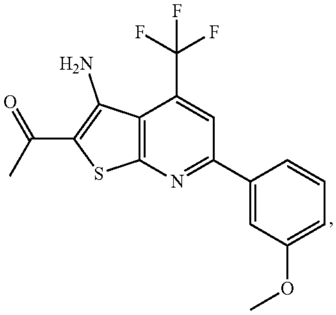,
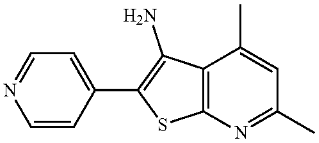,
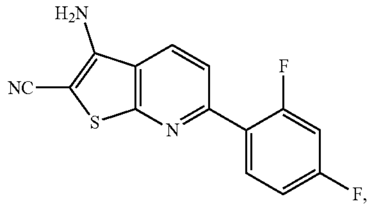,
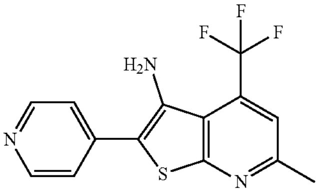, -continued
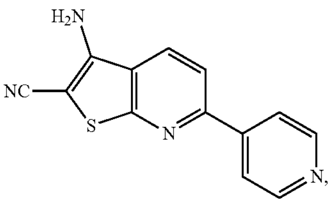
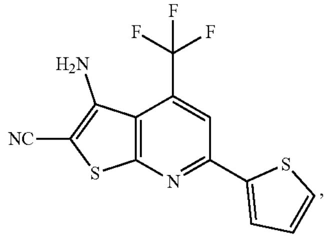
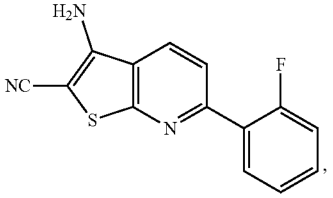
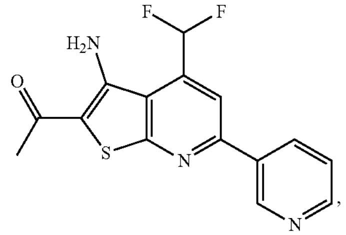
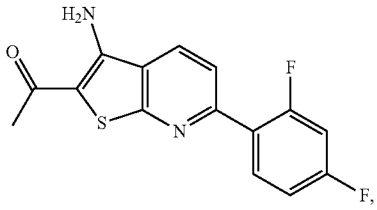
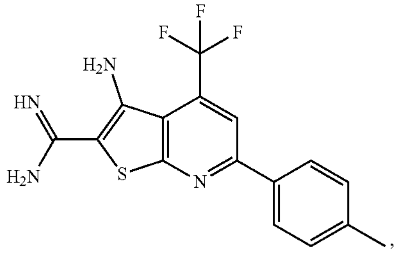
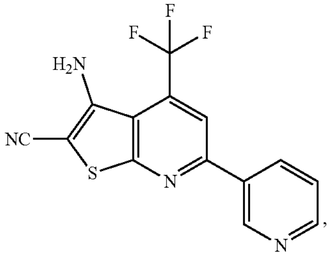
-continued
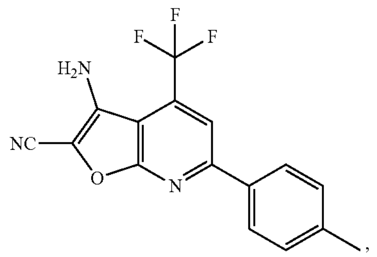
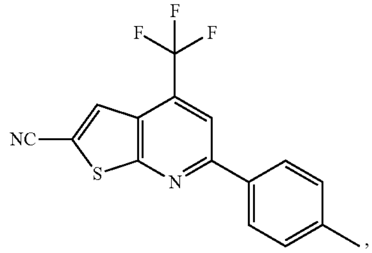
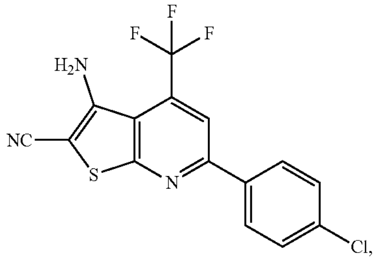
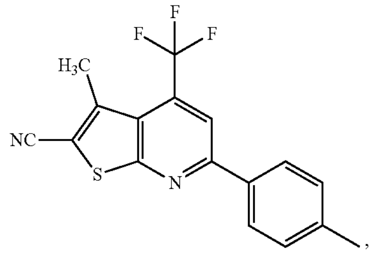
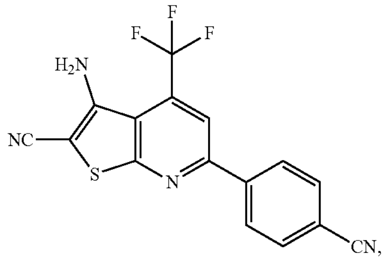
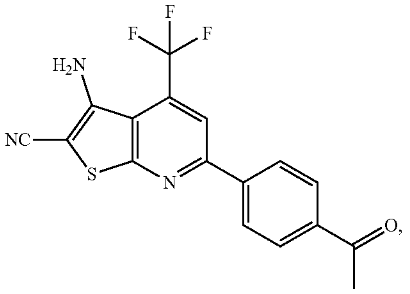

-continued

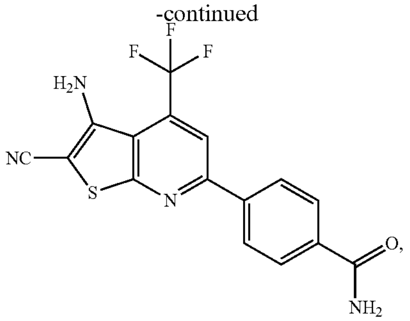

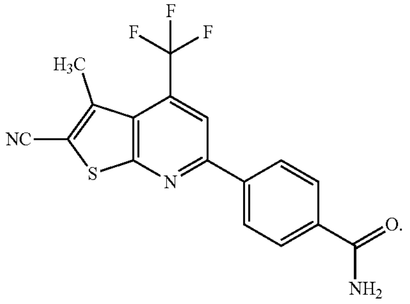

In some embodiments, the material topically administered to a skin region is of the formula (II):

(II)

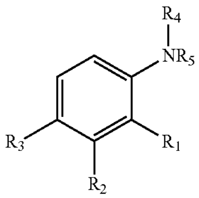

wherein each of R1, R2, R3, R4 and R5 may be H, excluding wherein R1, R2, R3, R4 and R5 are each H;

each of R1, R2 and R3 may, independently, be selected from halide (e.g., F, Cl, Br, I), —C1-C5alkyl, —C2-C6alkenyl, —C2-C6alkynyl, —C6-C10aryl, —C5-C10heteroaryl, —OH, —OC1-C5alkyl, —OC2-C6 alkenyl, —OC2-C6alkynyl, —OC6-C10aryl, —OC5-C10heteroaryl, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5haloalkyl, —C1-C5alkyl-C6-C10aryl, —C1-C5alkyl-C5-C10heteroaryl and —NR'R", each of R4 and R5, independently, is C1-C5alkyl, —C2-C6alkenyl, —C2-C6alkynyl, —C6-C10aryl, —C5-C10heteroaryl, —OH, —OC1-C5alkyl, —OC2-C6 alkenyl, —OC2-C6alkynyl, —OC6-C10aryl, —OC5-C10heteroaryl, —C(═O)H, —C(═O)C1-C5alkyl, —C(═O)C1-C5alkylhalide, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C(═S)H, —C(═S)C1-C5alkyl, —C(═S)C6-C10aryl, —C(═S)C5-C10heteroaryl, —C(═S)NR'R", —C(═S)SC1-C5alkyl, —C(═S)SC6-C10aryl, —C(═S)SC5-C10heteroaryl, —C(═S)C1-C5alkylhalide, —C1-C5haloalkyl, —C1-C5alkyl-C6-C10aryl, —C1-C5alkyl-C5-C10heteroaryl, R4 and R5 together with the nitrogen atom to which they are bonded may form a ring structure comprising between 4 and 7 atoms, the ring structure being optionally substituted by at least one group or atom selected from —H, halide, a carbonyl group, —OH, —SH, —NR'R", C1-C5alkyl, —C2-C6alkenyl, —C2-C6alkynyl, —C6-C10aryl, —C5-C10heteroaryl, —OH, —OC1-C5alkyl, —OC2-C6 alkenyl, —OC2-C6alkynyl, —OC6-C10aryl, —OC5-C10heteroaryl, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5haloalkyl, —C1-C5alkyl-C6-C10aryl and —C1-C5alkyl-C5-C10heteroaryl, each of R' and R", independently of the other, may be H, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5alkyl, —C1-C5haloalkyl, —C1-C5alkyl-C6-C10aryl, —C1-C5alkyl-C5-C10heteroaryl, —C6-C10aryl and —C5-C10heteroaryl.

In some embodiments, at least one of R1, R2 and R3 is a halide (e.g., F, Cl, Br, I). In some embodiments, the halide is F or Cl or Br or I.

In some embodiments, at least one of R1, R2 and R3 is F and another one of R1, R2 and R3 is Cl or I.

In some embodiments, at least one of R1, R2 and R3 is a halide and another one of f R1, R2 and R3 is H.

In some embodiments, at least one of R1, R2 and R3 is selected from —C1-C5alkyl, —C2-C6alkenyl, —C2-C6alkynyl, —C6-C10aryl and —C5-C10heteroaryl.

In some embodiments, each of R4 and R5 is H.

In some embodiments, at least one of R4 and R5 is H and the other is selected from C1-C5alkyl, —C2-C6alkenyl, —C2-C6alkynyl, —C6-C10aryl, —C5-C10heteroaryl, —OH, —OC1-C5alkyl, —OC2-C6 alkenyl, —OC2-C6alkynyl, —OC6-C10aryl, —OC5-C10heteroaryl, —C(═O)H, —C(═O)C1-C5alkyl, —C(═O)C1-C5alkylhalide, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C(═S)H, —C(═S)C1-C5alkyl, —C(═S)C6-C10aryl, —C(═S)C5-C10heteroaryl, —C(═S)NR'R", —C(═S)SC1-C5alkyl, —C(═S)SC6-C10aryl, —C(═S)SC5-C10heteroaryl, —C(═S)C1-C5alkylhalide, —C1-C5haloalkyl, —C1-C5alkyl-C6-C10aryl and —C1-C5alkyl-C5-C10heteroaryl.

In some embodiments, at least one of R4 and R5 is H and the other is —H, —C1-C5alkyl, —C(═O)C1-C5alkylhalide or —C(═S)NR'R".

In some embodiments, R4 and R5 together with the nitrogen atom to which they are bonded may form a ring structure comprising between 4 and 7 atoms. In some embodiments, the ring structure comprises at least 3 carbon atoms and the nitrogen atom. In some embodiments, the ring structure comprises at least one additional heteroatom selected from N, O and S. In some embodiments, the ring structure is a 4-, 5- or 6-membered ring structure.

In some embodiments, the ring structure is a 4-membered ring structure.

In some embodiments, the ring structure is substituted by at least one group or atom selected from —H, halide, a carbonyl group, —OH, —SH, —NR'R", C1-C5alkyl, —C2-C6alkenyl, —C2-C6alkynyl, —C6-C10aryl, —C5-C10heteroaryl, —OH, —OC1-C5alkyl, —OC2-C6 alkenyl, —OC2-C6alkynyl, —OC6-C10aryl, —OC5-C10heteroaryl, —C(═O)H, —C(═O)C1-C5alkyl, —C(═O)C6-C10aryl, —C(═O)C5-C10heteroaryl, —C(═O)NR'R", —C(═O)OC1-C5alkyl, —C(═O)OC6-C10aryl, —C(═O)OC5-C10heteroaryl, —C1-C5haloalkyl, —C1-C5alkyl-C6-C10aryl and —C1-C5alkyl-C5-C10heteroaryl.

In some embodiments, the ring structure is substituted by a halide, a carbonyl group, —C1-C5alkyl, —C2-C6alkenyl, —C2-C6alkynyl or —C6-C10aryl. In some embodiments, the ring structure is substituted by a halide or a carbonyl group.

In some embodiments, the compound is selected from:

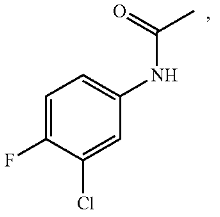

(herein designated compound SN-7)

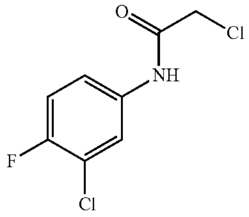

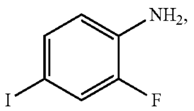

(herein designated compound SN-1)

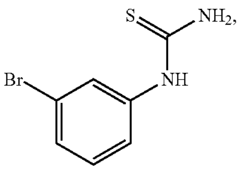

(herein designated compound SN-4)

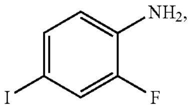

(herein designated compound SN-5)

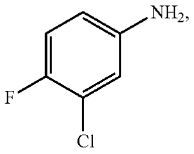

(herein designated compound SN-6)

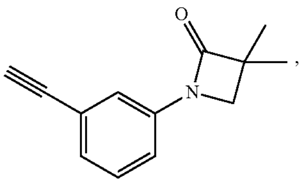

(herein designated compound SN-2)

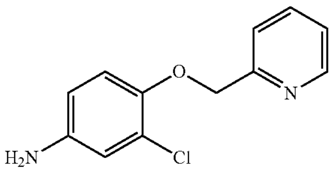

and (herein designated compound SN-8)

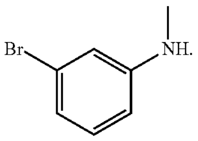

(herein designated compound SN-3)

In some embodiments, the compound is a compound herein designated SN-9:

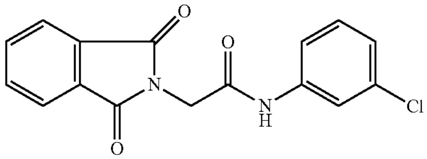 [SMILES: O=C(CN1C(=O)c2ccccc2C1=O)Nc1cccc(Cl)c1]

In some embodiments, the at least one topically administered material is selected amongst:

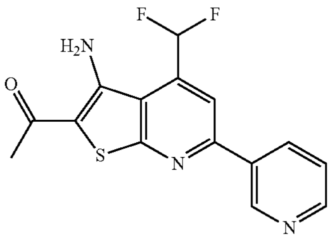 [SMILES: CC(=O)c1sc2nc(-c3cccnc3)cc(C(F)F)c2c1N]

1-[3-amino-4-(difluoromethyl)-6-(3-pyridinyl)thieno[2,3-b]pyridin-2-yl]ethanone (herein referred to as compound G4);

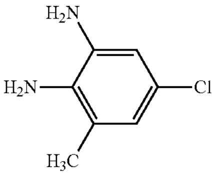

(2-amino-4-chloro-6-methylphenyl)amine hydrochloride (herein referred to as compound E3, as free base or as a salt form, e.g., salt of HCl);

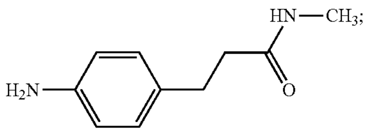

3-(4-aminophenyl)-N-methylpropanamide

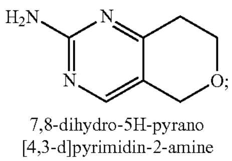

7,8-dihydro-5H-pyrano[4,3-d]pyrimidin-2-amine

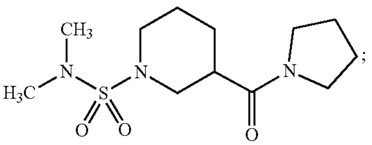

N,N-dimethyl-3-(1-pyrrolidinylcarbonyl)-1-piperidinesulfonamide

-continued

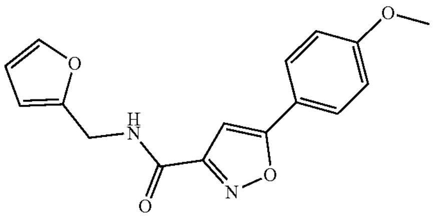
;

N-(2-furylmethyl)-5-(4-methoxyphenyl)-3-isoxazolecarboxamide

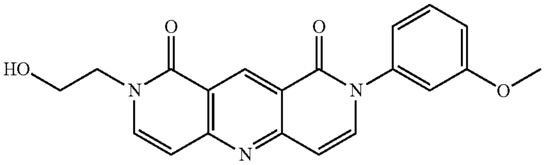
;

2-(2-hydroxyethyl)-8-(3-methoxyphenyl)pyrido[4,3-b]-1,6-naphthyridine-1,9(2H,8H)-dione

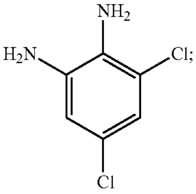
;

(2-amino-3,5-dichlorophenyl)amine

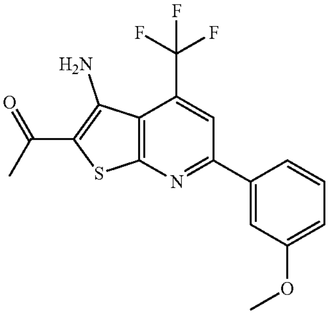
;

1-[3-amino-6-(3-methoxyphenyl)-4-(trifluoromethyl)thieno[2,3-b]pyridin-2-yl]ethanone

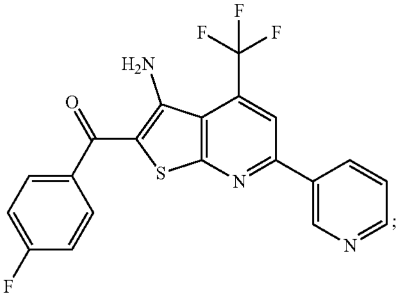
;

[3-amino-6-(3-pyridinyl)-4-(trifluoromethyl)thienol[2,3-b]pyridin-2-yl](4-fluorophenyl)methanone -continued

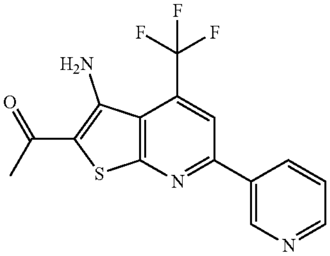
;

1-[3-amino-6-(3-pyridinyl)-4-(trifluoromethyl)thieno[2,3-b]pyridin-2-yl]ethanone

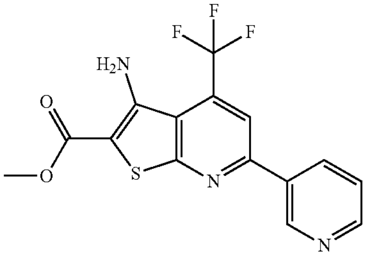

methyl 3-amino-6-(3-pyridinyl)-4-(trifluoromethyl)thieno[2,3-b]pyridine-2-carboxylate and further a compound selected

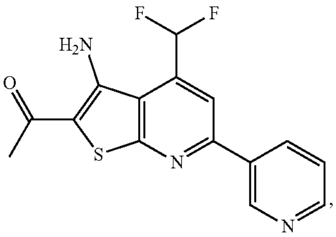
,

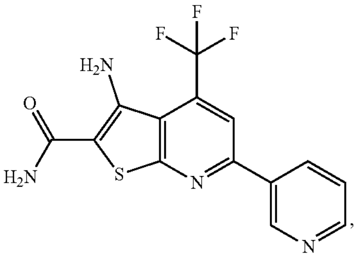
,

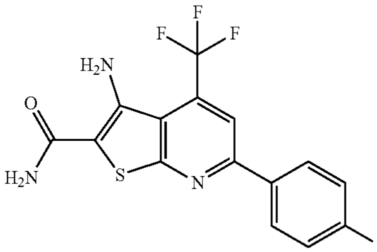
Br,

-continued
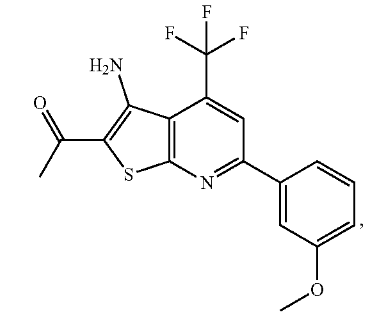
,
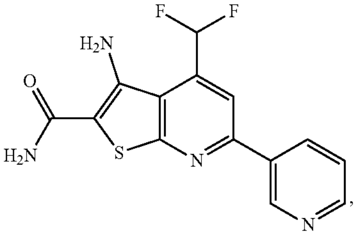
,
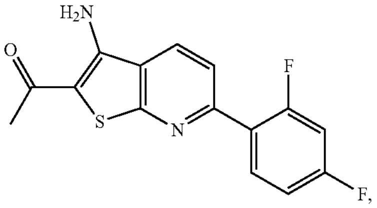
,
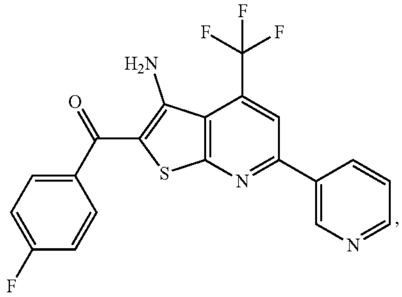
,
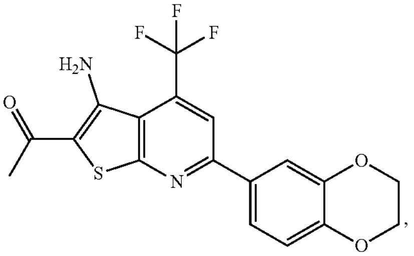
,
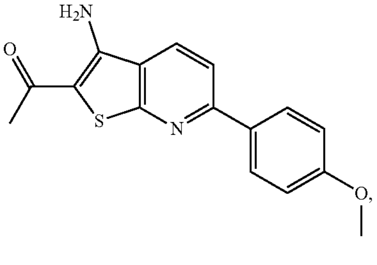
,
-continued
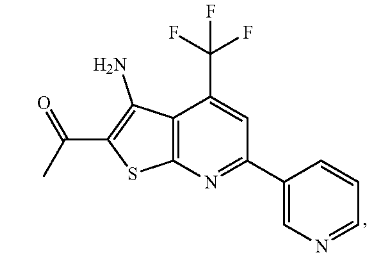
,
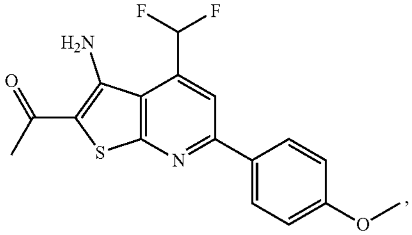
,
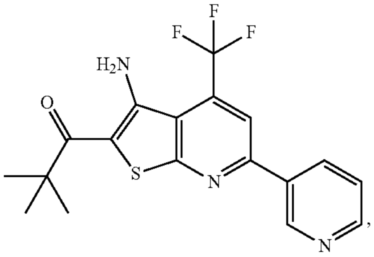
,
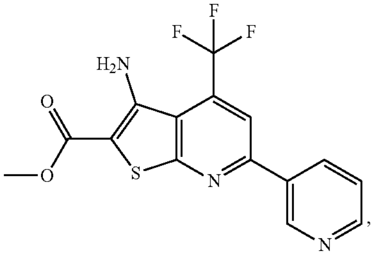
,
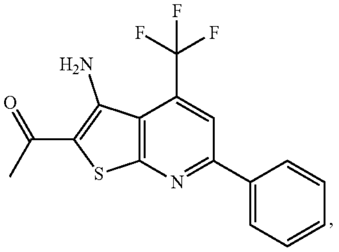
,
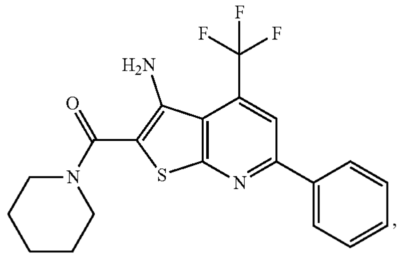
, -continued
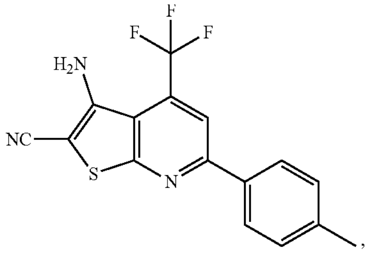
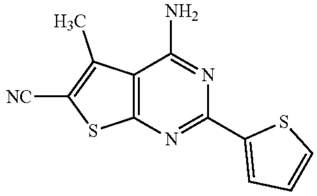
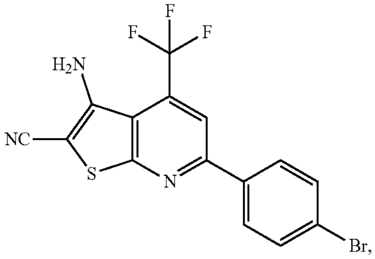
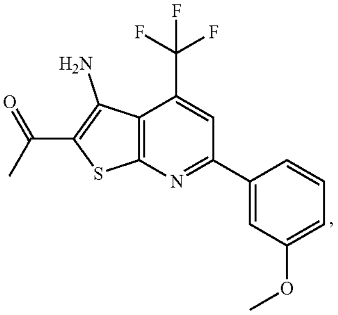
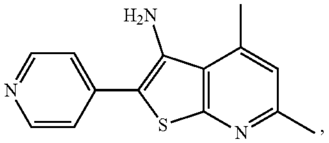
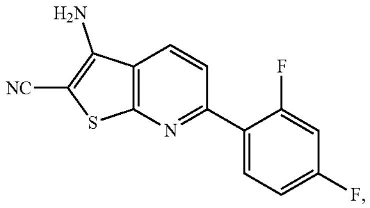
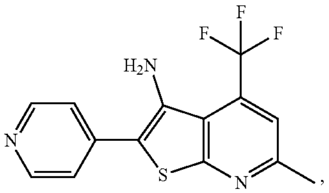
-continued
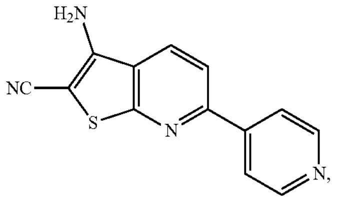
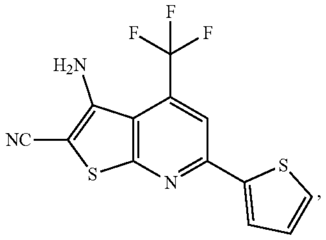
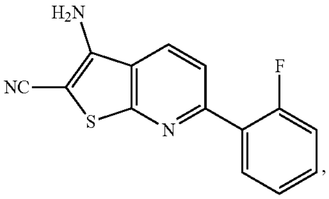
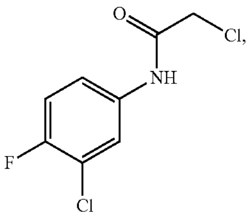
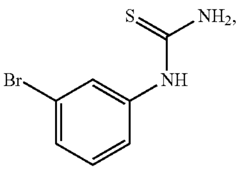
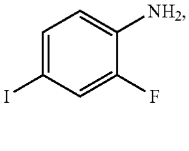
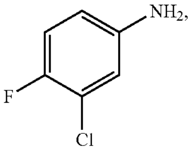
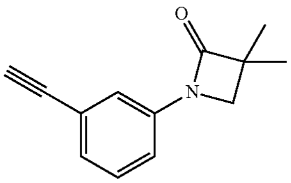
and
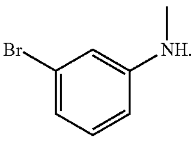

In some embodiments, the at least one topically administered material is selected from:

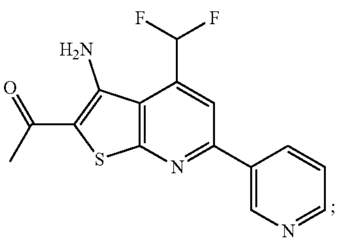

1-[3-amino-4-(difluoromethyl)-6-(3-pyridinyl)thieno[2,3-b]pyridin-2-yl]ethanone
(herein referred to as compound G4)

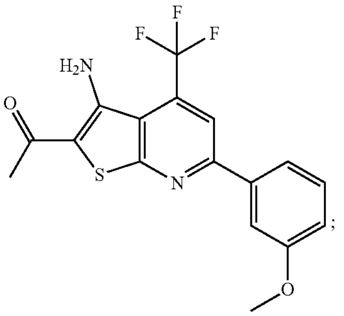

1-[3-amino-6-(3-methoxyphenyl)-4-(trifluoromethyl)thieno[2,3-b]pyridin-2-yl]ethanone

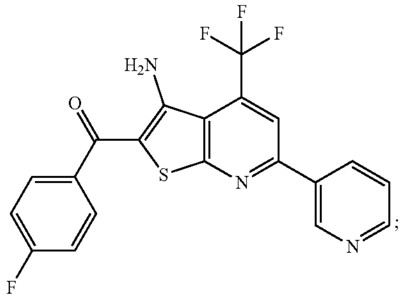

[3-amino-6-(3-pyridinyl)-4-(trifluoromethyl)thienol[2,3-b]pyridin-2-yl](4-fluorophenyl)methanone

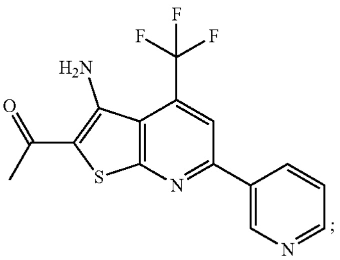

and

1-[3-amino-6-(3-pyridinyl)-4-(trifluoromethyl)thieno[2,3-b]pyridin-2-yl]ethanone -continued

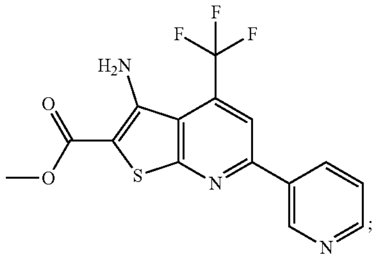

methyl 3-amino-6-(3-pyridinyl)-4-(trifluoromethyl)thieno[2,3-b]pyridine-2-carboxylate or a compound selected from:

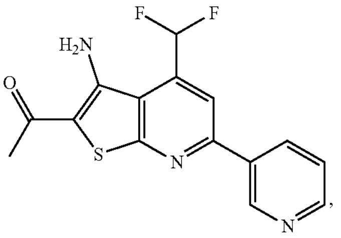

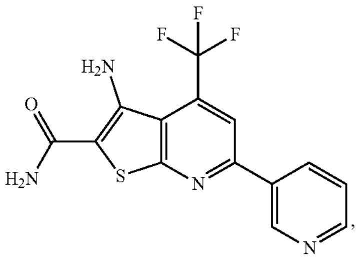

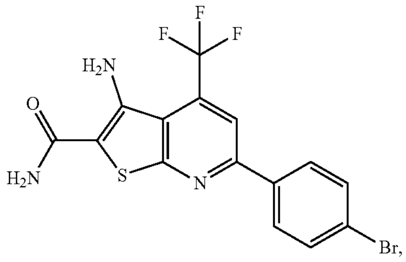

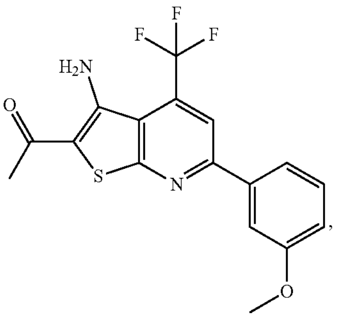

-continued
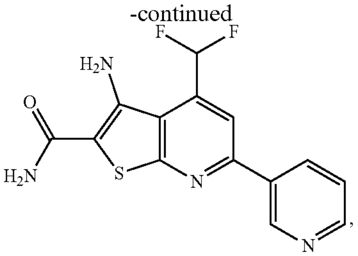
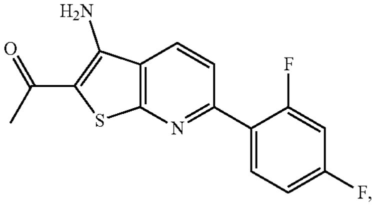
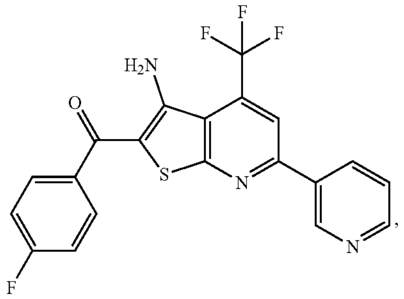
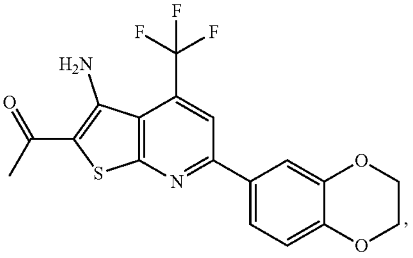
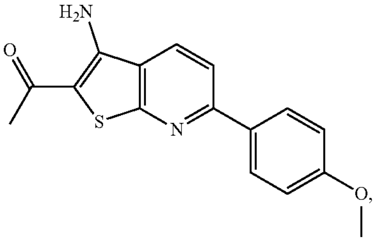
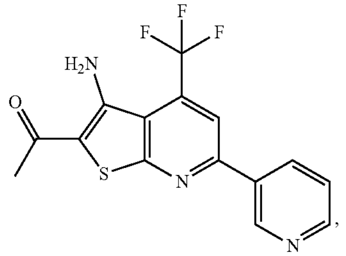
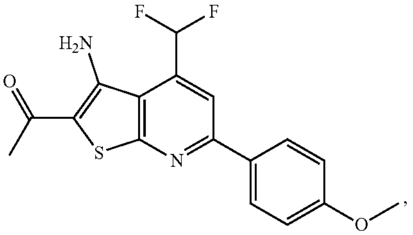
-continued
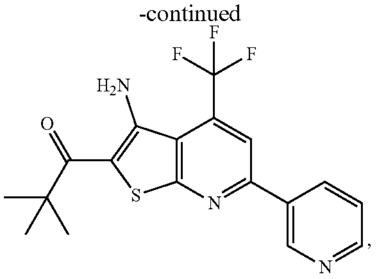
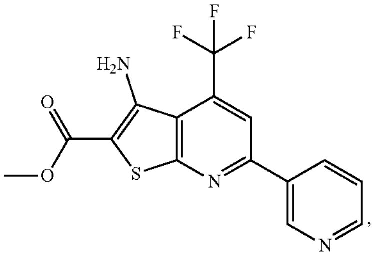
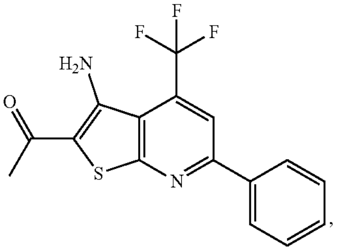
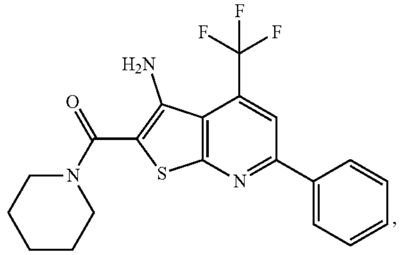
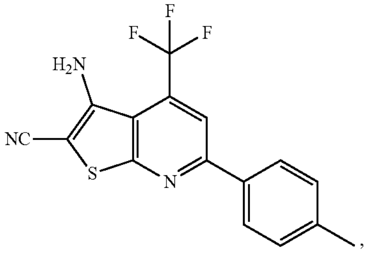
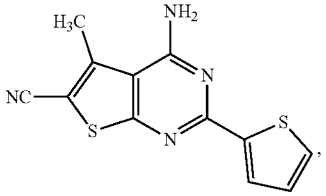
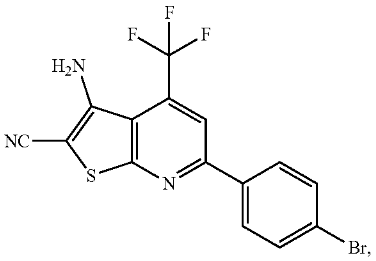

-continued

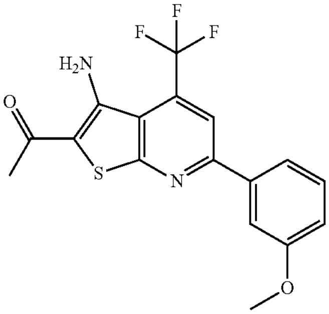,

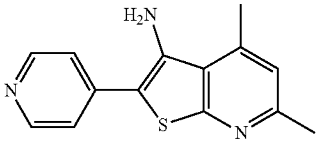,

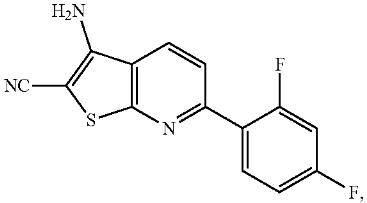

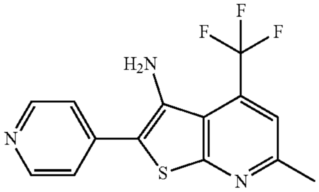,

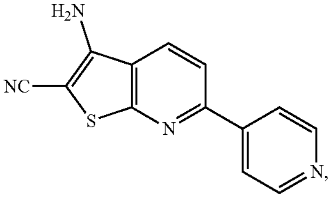

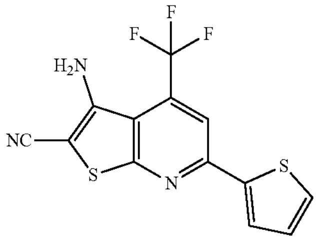,

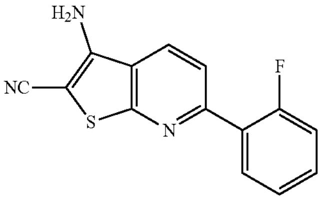,

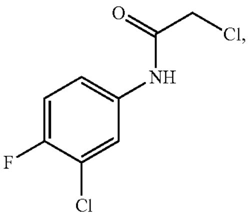

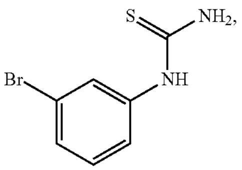

-continued

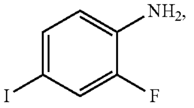

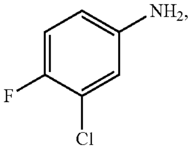

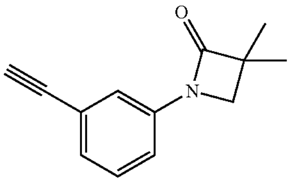

and

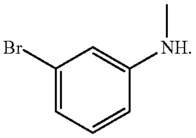

In some embodiments, the at least one material is selected from:

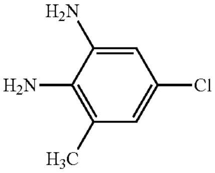

(2-amino-4-chloro-6-methylphenyl)amine hydrochloride (herein referred to as compound E3, as free base or as a salt form, e.g., salt of HCl); and

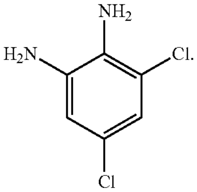

(2-amino-3,5-dichlorophenyl)anime

In some embodiments, the at least one material is selected from

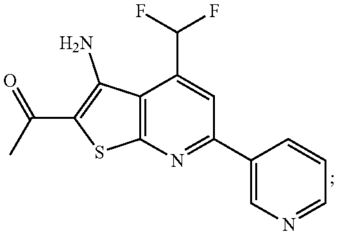; and

1-[3-amino-4-(difluoromethyl)-6-(3-pyridinyl)thieno[2,3-b]pyridin-2-yl]ethanone (herein reffered to as compound G4)

-continued
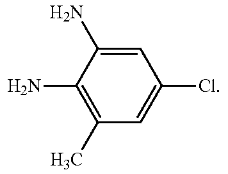
(2-amino-4-chloro-6-methylphenyl)amine hydrochloride (herein reffered to as a compound E3, as free base or as a salt form, e.g., salt of HCl)
In some embodiments, the compound is selected from
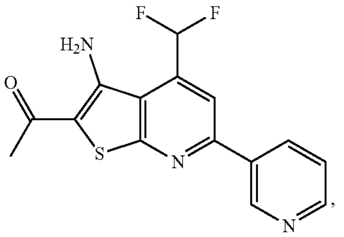
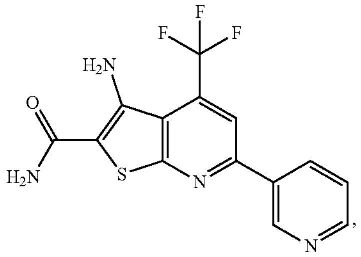
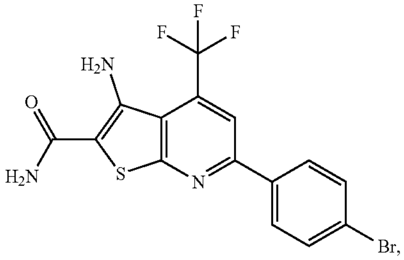
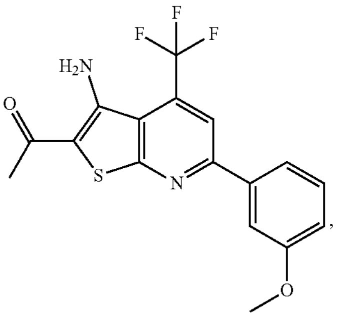
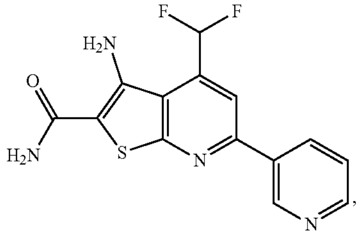
-continued
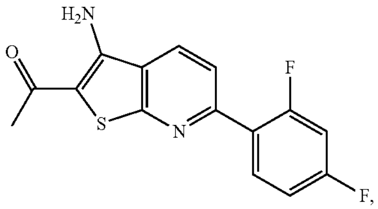
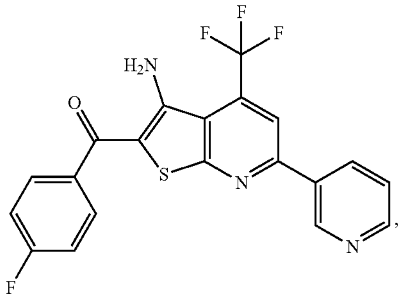
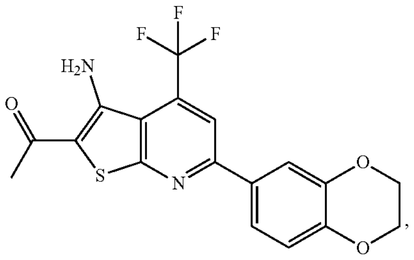
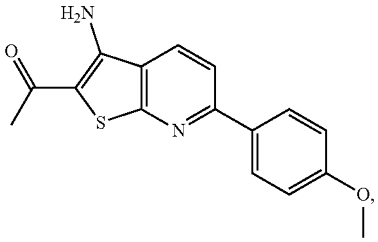
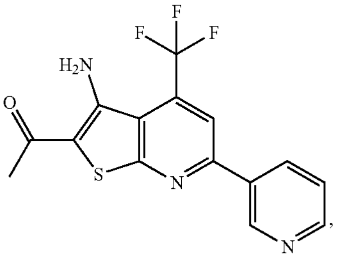
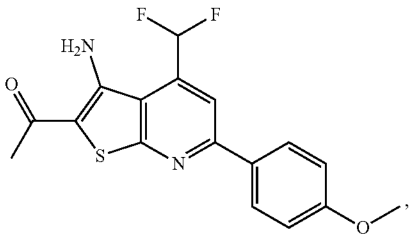

-continued
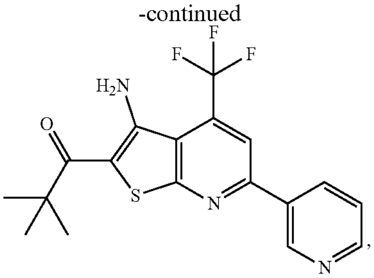
,
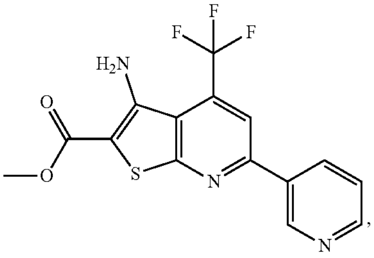
,
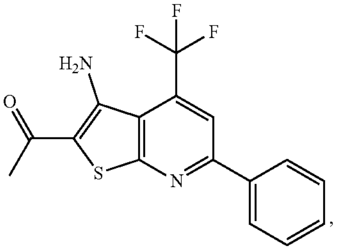
,
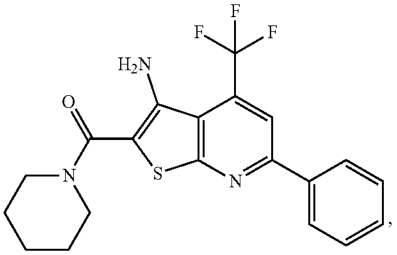
,
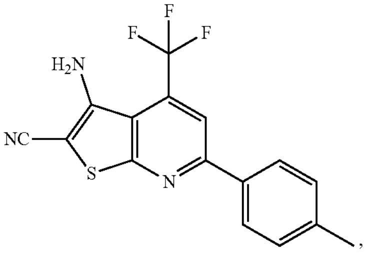
,
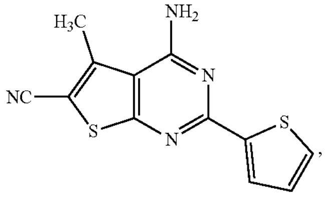
,
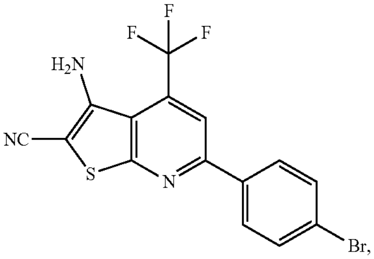
,
-continued
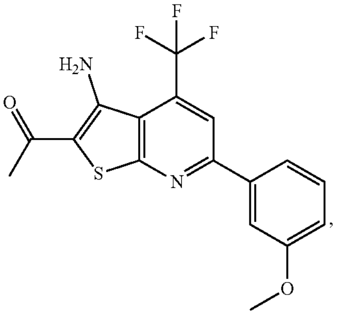
,
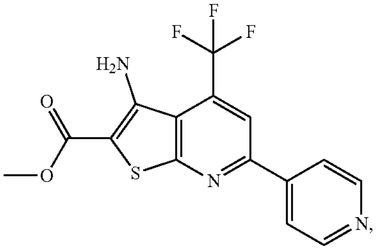
,
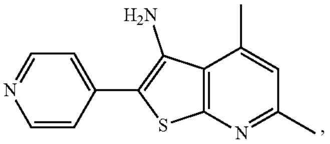
,
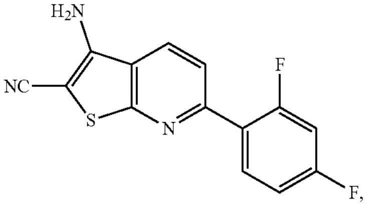
,
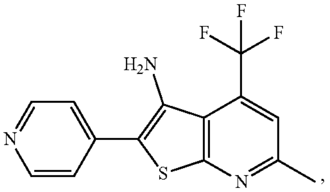
,
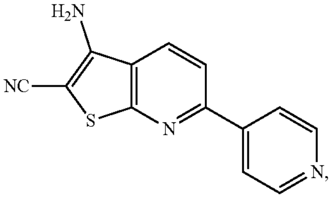
,
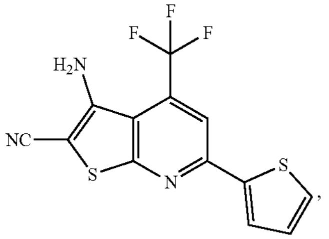
, -continued

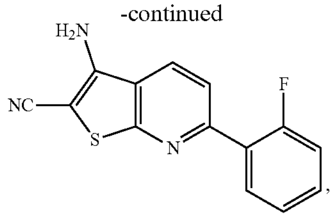

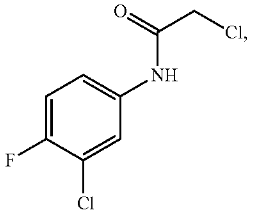

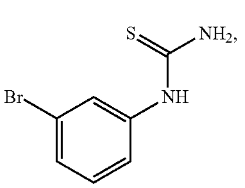

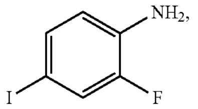

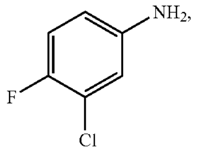

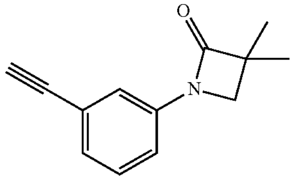

and

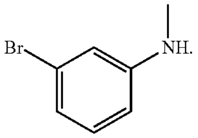

In some embodiments, the material is herein designated LW11:

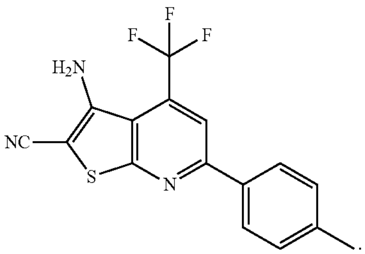 [SMILES: Cc1ccc(-c2cc(C(F)(F)F)c3c(N)c(C#N)sc3n2)cc1]

The at least one systemically administered drug which administration induces the skin toxicities to be prevented, limited or minimized may be any such drug or combination of drugs used in the treatment or prevention of a disease state, a condition or a symptom in a subject undergoing treatment. Unlike the material that is applied to a skin region, the drug is administered by a mode of administration resulting in the drug reaching the systemic blood stream (blood circulation). The drug may be administered by any mode of systemic administration selected from oral, aerosol, parenteral, subcutaneous, intravenous, intramuscular, inter-peritoneal and rectal administrations. The drug is not administered topically onto a skin region.

The skin toxicity associated with the at least one drug may result from a variety of factors, some may be unknown. Notwithstanding any particular toxicity inducing mechanism or pathway, the toxicity induced by the use of any one particular drug may range from mild to severe and may therefore mildly or severely affect compliance of patients and cause interruptions or discontinuation of therapy, and most significantly reduce quality of life of patients undergoing treatment. The toxicity, or side effect, may be in the form of a rash, maculopapular rash (Morbilliform Eruption), dermatomyositis-like rash, folliculitis, acne form eruptions, papulopustular rash, scleroderma-like changes, psoriasiformic rash, scleroderma form dermatitis, seborrheic dermatitis like rash (dandruff), seborrheic inflammation or actinic keratosis, pseudocellulitis, alopecia, tricomegaly, depigmentation, extravasation, pigmentary changes, mucositis, photosensitivity, xerosis, paronychia and others.

The at least one systemically administered drug may be a biological drug, such as an antibody, an antigen-binding fragment of an antibody, an interleukin, a cytokine, a growth factor and a vaccine; or a chemical drug.

The at least one systemically administered drug may be one used in oncological therapies, i.e. an anticancer drug selected in the treatment of at least one cancer; the cancer may be selected amongst breast cancer, cervical cancer, ovarian cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstroem's macroglobinaemia, nasopharyngeal, neuroendocrine cancer, mesothelioma, angiosarcoma, Kaposi's sarcoma, carcinoid, fallopian tube cancer, peritoneal cancerpapillary serous muellerian cancer, malignant ascites, gastrointestinal stromal tumor (GIST), Li-Fraumeni syndrome and Von Hippel-Lindau syndrome (VHL), cancer of unknown origin either primary or metastatic, wherein the cancer is invasive, metastatic or non-metastatic.

The at least one systemically administered drug may be selected from signal transduction inhibitors (such as epidermal growth factor receptor, EGFR, antagonists and multi-kinase inhibitors and tyrosine kinase inhibitors), proteasome inhibitors and spindle inhibitors (Taxanes and Vinca alkaloids).

In some embodiments, the at least one systemically administered drug is a signal transduction inhibitor selected amongst epidermal growth factor receptor, epidermal growth factor receptor (EGFR), antagonists and multi-kinase inhibitors (selected amongst specific and non-specific) including mitogen-activated protein kinase inhibitors.

In some embodiments, the cancer may be associated with EGFR. In some embodiments, the cancer is one treatable with at least one EGFR antagonist. In some embodiments, the cancer is colon cancer, lung cancer, head and neck cancer, breast cancer or pancreas cancer.

In some embodiments, where the drug administrated systematically is an EGFR antagonist, the material administered to a skin region is a material of formula (I), as defined and selected herein. In some embodiments, the material is LW11:

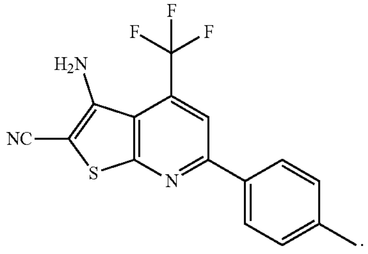 [SMILES: Cc1ccc(-c2cc(C(F)(F)F)c3c(N)c(C#N)sc3n2)cc1]

In some embodiments, the at least one systemically administered drug is an antibody selected from monoclonal antibodies (mAbs) used in therapy.

The monoclonal antibody may be selected from anti-EGFR mAbs.

The mAbs may be any one or more of cetuximab, panitumumab, pertuzumab, nimotuzumab, trastuzumab, rituximab, ofatumumab, veltuzumab, alemtuzumab, labetuzumab, adecatumumab, oregovomab, onartuzumab, dulanermin, apomab, mapatumumab, lexatumumab, conatumumab and tigatuzumab.

In some embodiments, the material administered to a skin region is a compound of formula (I), administered in combination, as defined herein, with an anti-EGFR mAbs.

In some embodiments, the drug is selected from antibody fragments, bi-specific antibodies and bi-specific T-cell engagers (BiTEs). Non-limiting examples may be selected from catumaxomab and blinatumomab.

In some embodiments, the drug is an antibody drug conjugate (ADC) or an immunoconjugate, such as ibritumomab triuxetan, tositumomab, brentuximab vedotin, gemtuzumab ozogamicin, clivatuzumab tetraxetan, pemtumomab and trastuzumab emtansine.

In some embodiments, the drug is one used in an anti-angiogenic therapy, such as bevacizumab, etaracizumab, volociximab, ramucirumab, aflibercept, sorafenib, sunitinib, regorafenib, axitinib, nintedanib, motesanib, pazopanib and cediranib.

In some embodiments, the at least one drug is a tyrosine kinase inhibitor (TKI). In some embodiments, the drug is one or more of nilotinib, midostaurin, gefitinib, erlotinib, dasatinib, bosutinib, ponatinib and ibrutinib.

In some embodiments, the at least one drug is a kinase inhibitor- the BRAF protein is a serine/threonine-kinase involved in the mitogen-activated protein-kinase (MAPK) signaling pathway (B-Raf/Mek/Erk proteins and MEK is a serine/tyrosine/threonine kinase). In some embodiments, the drug is one or more of a MEK inhibitor selected from trametinib, cobimetinib and binimetinib or a BRAF inhibitor such as dabrafenib, vemurafenib, encorafenib.

In some embodiments, the cancer may be treatable with at least one TKI.

In some embodiments, the material administered to a skin region is a compound of formula (II), administered in combination, as defined herein, with at least one TKI.

The invention further provides a drug delivery system for use in a method of preventing or minimizing skin toxicity induced by at least one systemically administered drug, as recited herein. In some embodiments, the drug delivery system allows slow release or sustained release of the material (cargo) at its intended target (e.g., sebaceous glands, hair follicles and nails).

Also provided is drug delivery system for use in a method of preventing or minimizing skin toxicity induced by at least one systemically administered drug, the drug delivery system comprising at least one topically administrable material.

Further provided is a drug delivery system for use in a method of preventing or minimizing skin toxicity induced by at least one systemically administered drug, the drug delivery system comprising at least one topically administrable material, wherein the at least one systemically administered drug is selected from (a) a signal transduction inhibitor, optionally selected amongst epidermal growth factor receptor, EGFR, antagonists and multi-kinase inhibitors; (b) a biological drug optionally selected from an antibody, an antigen-binding fragment of an antibody, an interleukin, a cytokine, a growth factor and a vaccine; (c) an anticancer drug; (d) a proteasome inhibitor; (e) a spindle inhibitor; (f) an antimetabolite; and (g) a genotoxic agent, each of the above- as defined herein.

Also provided is a method of (substantially) preventing skin toxicity associated with a treatment by at least one systemically administered drug, the method comprising topically administering at least one material prior to, concomitantly with or following systemic administration of the at least one drug.

Also provided is a method of preventing or treating a disease or disorder in a subject without (substantially) causing or inducing skin toxicities, the method comprising:

prior to, concomitantly with or following administration to the subject of at least one drug capable of preventing or treating the disease or disorder and causing a skin toxicity, topically administering at least one material capable of preventing the skin toxicity in said subject, wherein said skin toxicity is induced by or associated with the at least one drug.

In some embodiments, said interrupting is achievable by competitive or non-competitive association of the material administered to the skin to the target and/or association thereof to the systemically administered drug.

In some embodiments, the at least one systemically administered drug causes a skin toxicity or side effect selected from a rash, maculopapular rash (Morbilliform Eruption), dermatomyositis-like rash, folliculitis, acneform eruptions, scleroderma-like changes, psoriasisiform rash, sclerodermiform dermatitis, seborrheic dermatitis like rash (dandruff), seborrheic inflammation or actinic keratosis, pseudocellulitis, alopecia, tricomegaly, depigmentation, extravasation, pigmentary changes, mucositis, photosensitivity, xerosis, paronychia and others.

In some embodiments, the at least one systemically administered drug is a biological drug or a chemical drug.

In some embodiments, the biological drug is selected from an antibody, an antigen-binding fragment of an antibody, an interleukin, a cytokine, a growth factor and a vaccine.

In some embodiments, the at least one systemically administered drug is an anticancer drug used in prevention or treatment of a cancer selected amongst breast cancer, cervical cancer, ovarian cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstroem's macroglobinaemia, nasopharyngeal, neuroendocrine cancer, mesothelioma, angiosarcoma, Kaposi's sarcoma, carcinoid, fallopian tube cancer, peritoneal cancer-papillary serous muellerian cancer, malignant ascites, gastrointestinal stromal tumor (GIST), Li-Fraumeni syndrome and Von Hippel-Lindau syndrome (VHL).

In some embodiments, the at least one systemically administered drug is selected from signal transduction inhibitors, proteasome inhibitors, spindle inhibitors, antimetabolites and genotoxic agents.

In some embodiments, the at least one systemically administered drug is a signal transduction inhibitor selected amongst epidermal growth factor receptor, EGFR, antagonists and multi-kinase inhibitors.

In some embodiments, the at least one systemically administered drug is a tyrosine-kinase inhibitor (TKI).

In some embodiments, the at least one TKI drug is one or more of nilotinib, midostaurin, gefitinib, erlotinib, dasatinib, bosutinib, ponatinib and ibrutinib.

In some embodiments, the cancer is associated with epidermal growth factor receptor (EGFR).

In some embodiments, the cancer is one treatable with at least one EGFR antagonist.

In some embodiments, the at least one systemically administered drug is an antibody selected from monoclonal antibodies (mAbs) used in therapy.

In some embodiments, the monoclonal antibody is selected from anti-EGFR mAbs.

In some embodiments, the mAbs is one or more of cetuximab, panitumumab, nimotuzumab, trastuzumab, pertuzumab, rituximab, ofatumumab, veltuzumab, alemtuzumab, labetuzumab, adecatumumab, oregovomab, onartuzumab, dulanermin, apomab, mapatumumab, lexatumumab, conatumumab and tigatuzumab.

In some embodiments, the drug is selected from antibody fragments, bi-specific antibodies and bi-specific T-cell engagers (BiTEs).

In some embodiments, the antibody is selected from catumaxomab and blinatumomab.

In some embodiments, the drug is an antibody drug conjugate (ADC) or an immunoconjugate, selected from ibritumomab triuxetan, tositumomab, brentuximab vedotin, gemtuzumab ozogamicin, clivatuzumab tetraxetan, pemtumomab and trastuzumab emtansine.

In some embodiments, the drug is selected from bevacizumab, etaracizumab, volociximab, ramucirumab, aflibercept, sorafenib, sunitinib, regorafenib, axitinib, nintedanib, motesanib, pazopanib and cediranib.

The invention further provides a compound for use in medicine, the compound being selected from:

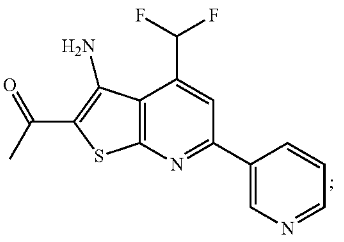

1-[3-amino-4-(difluoromethyl)-6-(3-pyridinyl)thieno[2,3-b]pyridin-2-yl]ethanone
(herein referred to as compound G4)

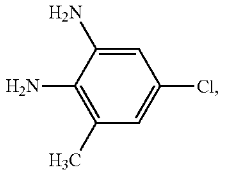

(2-amino-4-chloro-6-methylphenyl)amine hydrochloride
(herein referred to as compound E3 as free base or as a salt form, e.g., salt of HCl);

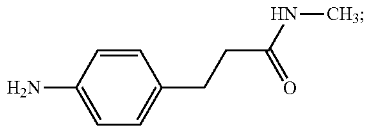

3-(4-aminophenyl)-N-methylpropanamide

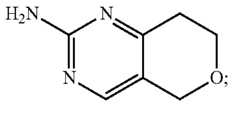

7,8-dihydro-5H-pyrano[4,3-d]pyrimidin-2-amine

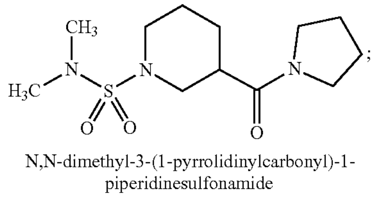

N,N-dimethyl-3-(1-pyrrolidinylcarbonyl)-1-piperidinesulfonamide

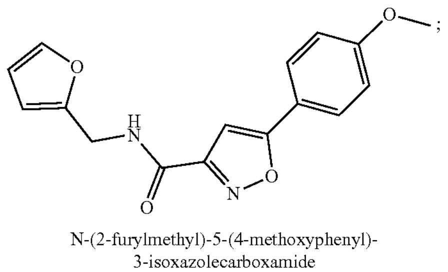

N-(2-furylmethyl)-5-(4-methoxyphenyl)-3-isoxazolecarboxamide

-continued

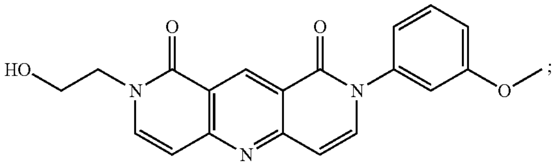

2-(2-hydroxyethyl)-8-(3-methoxyphenyl)pyrido[4,3-b]-1,6-naphthyridine-1,9(2H,8H)-dione

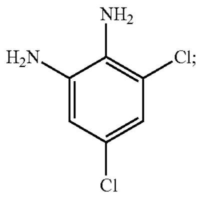

(2-amino-3,5-dichlorophenyl)amine

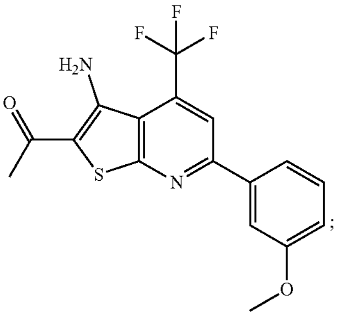

1-[3-amino-6-(3-methoxyphenyl)-4-(trifluoromethyl)thieno[2,3-b]pyridin-2-yl]ethanone

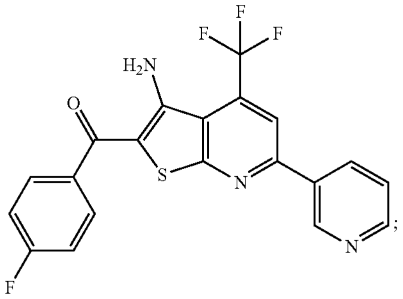

[3-amino-6-(3-pyridinyl)-4-(trifluoromethyl)thienol[2,3-b]pyridin-2-yl](4-fluorophenyl)methanone

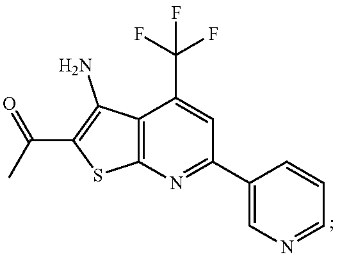

1-[3-amino-6-(3-pyridinyl)-4-(trifluoromethyl)thieno[2,3-b]pyridin-2-yl]ethanone -continued

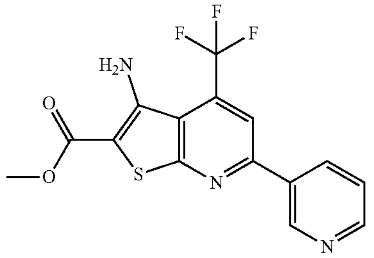

methyl 3-amino-6-(3-pyridinyl)-4-(trifluoromethyl)thieno[2,3-b]pyridine-2-carboxylate In some embodiments, the compound is selected from:

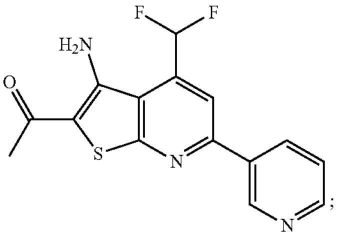

1-[3-amino-4-(difluoromethyl)-6-(3-pyridinyl)thieno[2,3-b]pyridin-2-yl]ethanone
(herein referred to as compound G4)

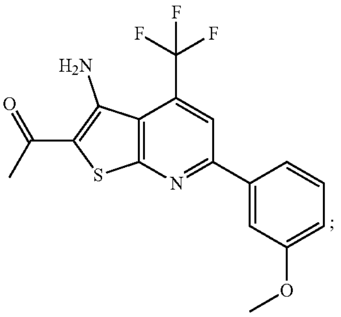

1-[3-amino-6-(3-methoxyphenyl)-4-(trifluoromethyl)thieno[2,3-b]pyridin-2-yl]ethanone

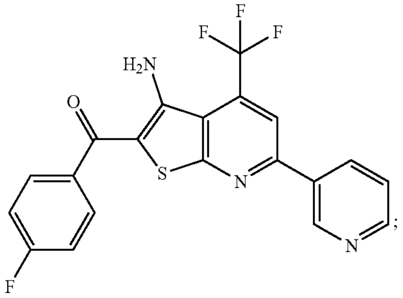

[3-amino-6-(3-pyridinyl)-4-(trifluoromethyl)thienol[2,3-b]pyridin-2-yl](4-fluorophenyl)methanone -continued

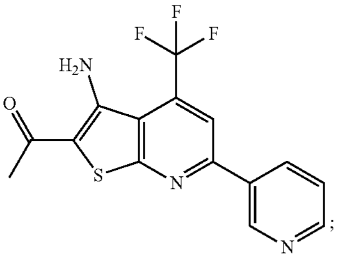

1-[3-amino-6-(3-pyridinyl)-4-(trifluoromethyl)thieno[2,3-b]pyridin-2-yl]ethanone

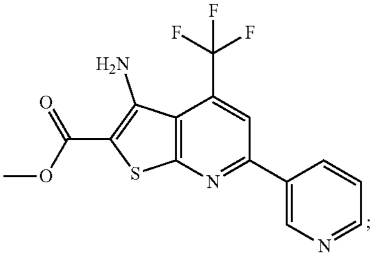

methyl 3-amino-6-(3-pyridinyl)-4-(trifluoromethyl)thieno[2,3-b]pyridine-2-carboxylate

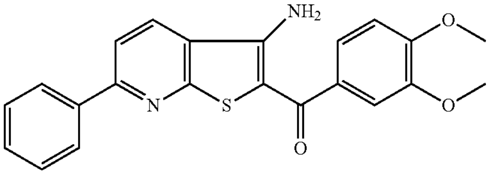

[3-amino-6-phenylthieno[2,3-b]pyridin-2-yl](3,4-dimethoxyphenyl)methanone

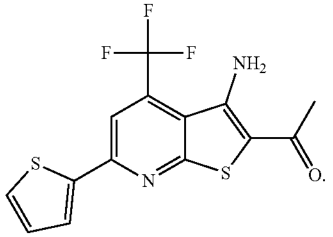

1-(3-amino-6-thiophen-2-yl-4-trifluoromethyl-thieno[2,3-b]pyridin-2-yl)-ethanone In some embodiments, the at least one material is selected from:

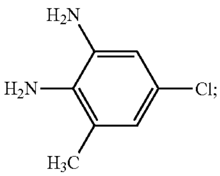
; and (2-amino-4-chloro-6-methylphenyl)amine hydrochloride (herein reffered to as a compound E3, as free base or as a salt form, e.g., salt of HCl)

-continued

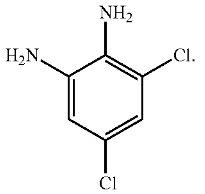

(2-amino-3,5-dichlorophenyl)amine

In some embodiments, the compound is selected from

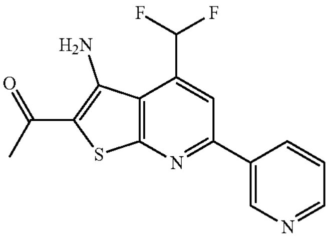
; and

1-[3-amino-4-(difluoromethyl)-6-(3-pyridinyl)thieno[2,3-b]pyridin-2-yl]ethanone (herein referred to as compound G4)

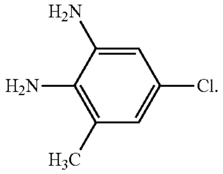

(2-amino-4-chloro-6-methylphenyl)amine hydrochloride (herein refered to as compound E3, as free base or as a salt form, e.g., salt of HCl)

In some embodiments, the compound is selected from

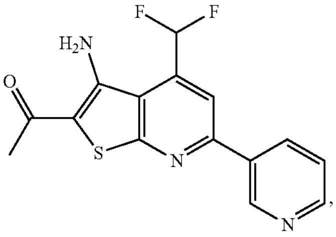
,

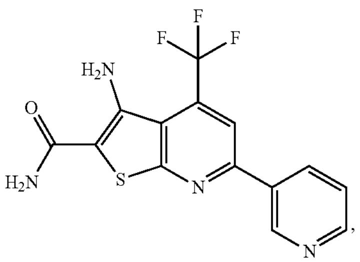
,

-continued
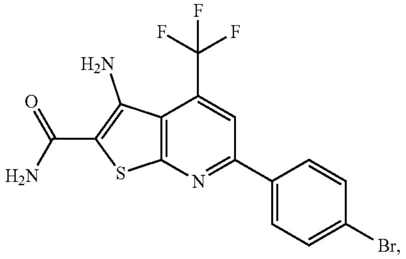
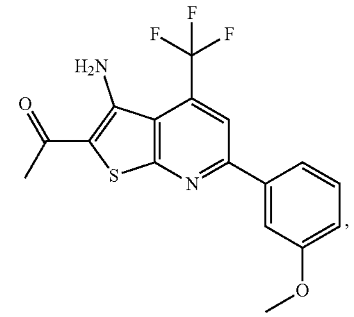
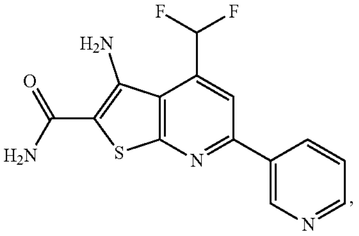
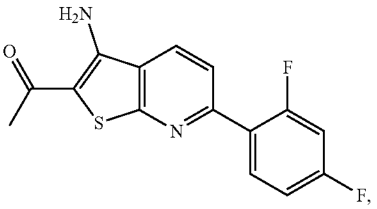
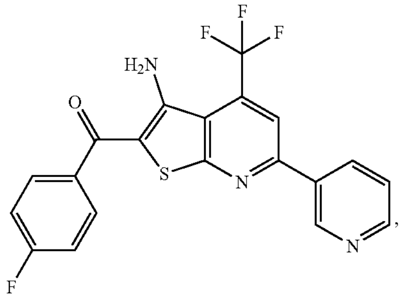
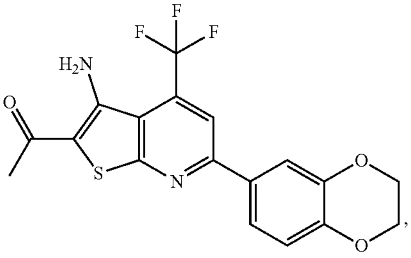
-continued
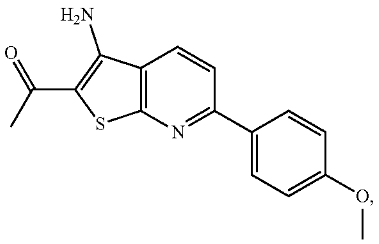
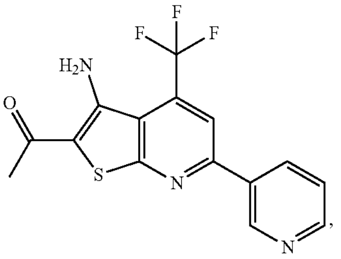
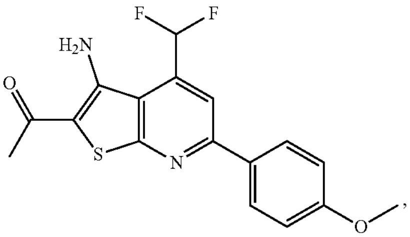
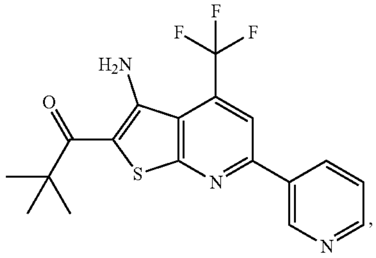
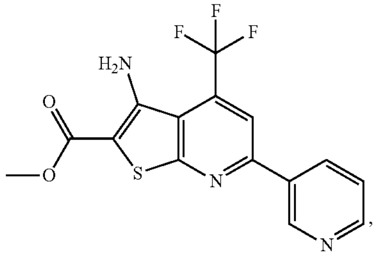
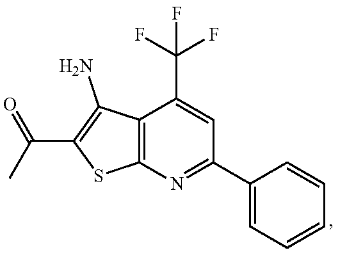

-continued
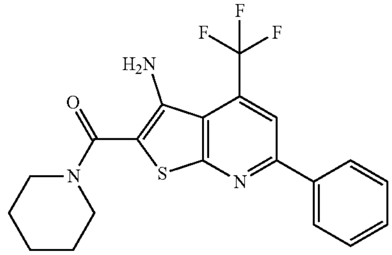,
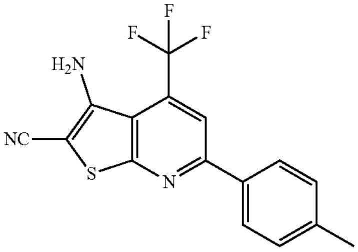,
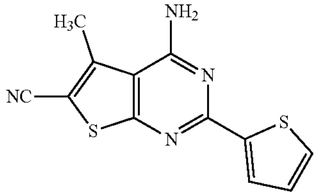,
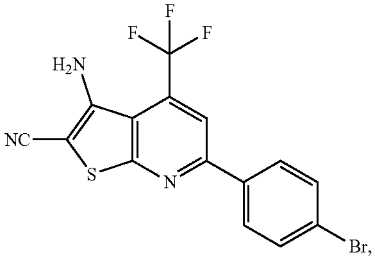,
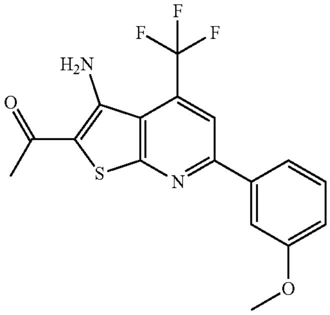,
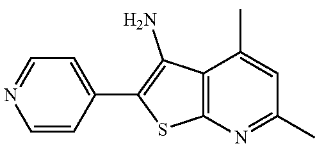,
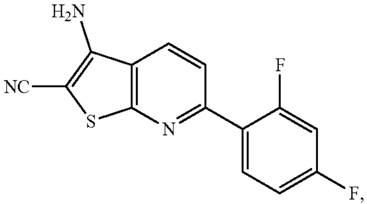,
-continued
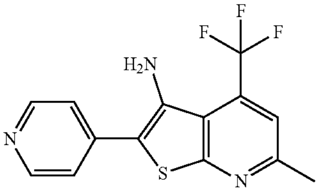,
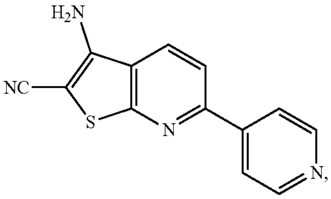,
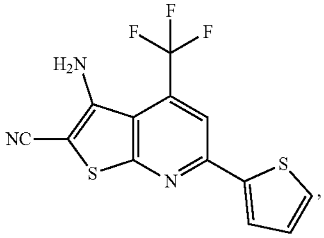,
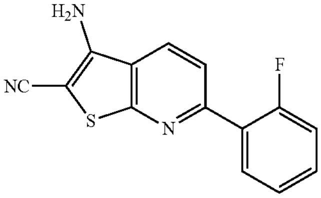,
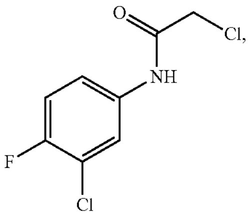, 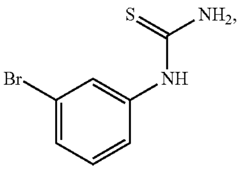,
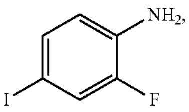, 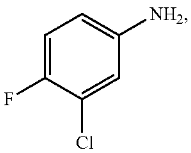,
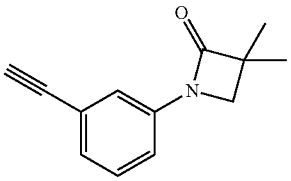 and
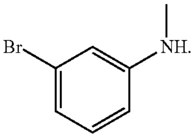.

In some embodiments, the compound has a structure selected from:
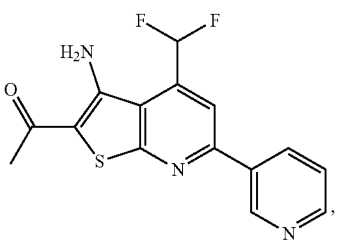
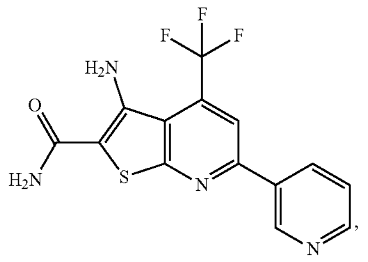
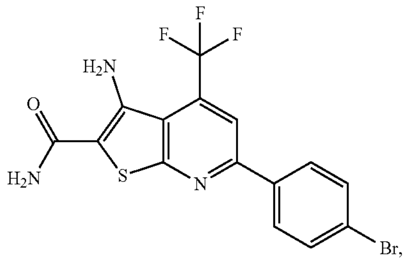
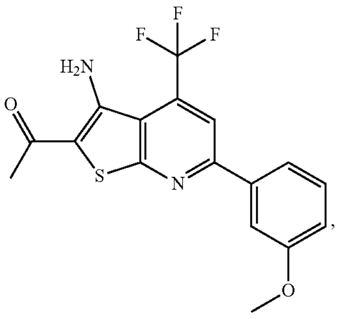
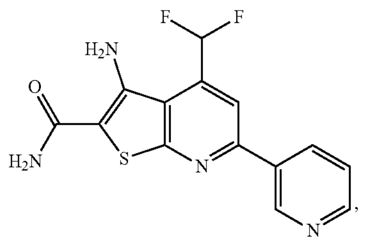
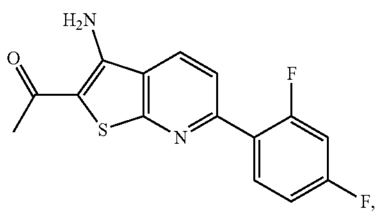
-continued
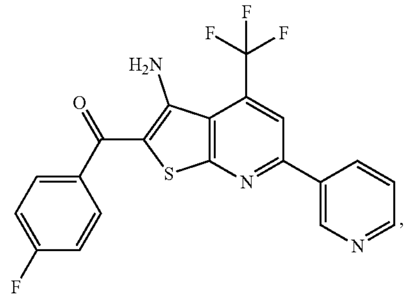
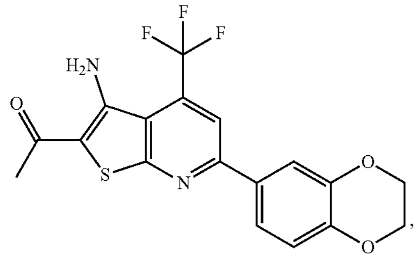
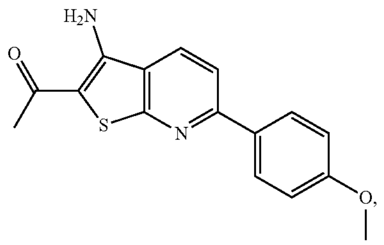
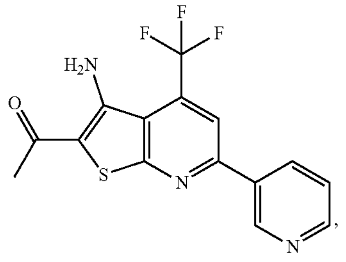
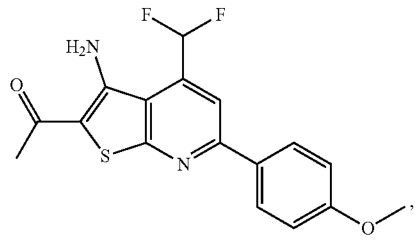
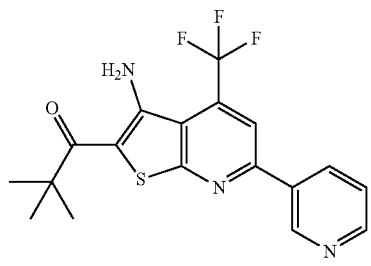

-continued
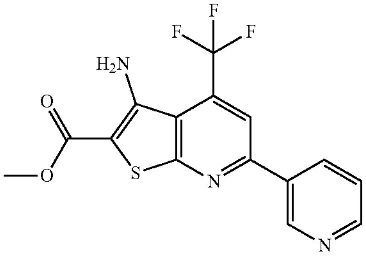
,
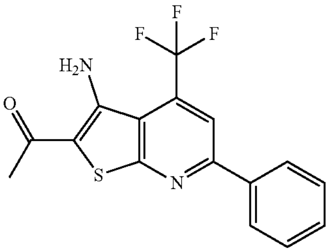
,
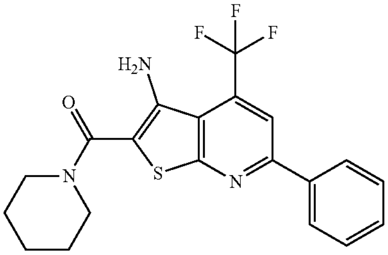
,
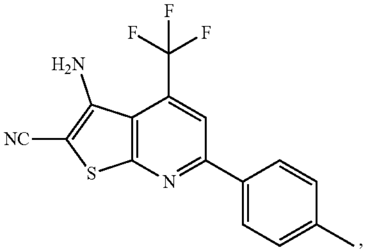
,
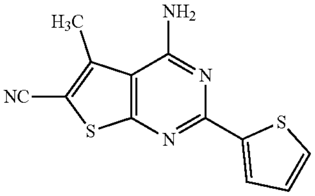
,
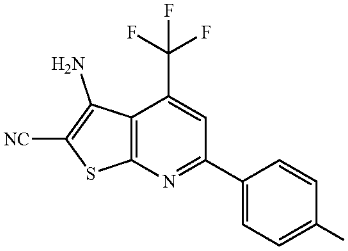
,
-continued
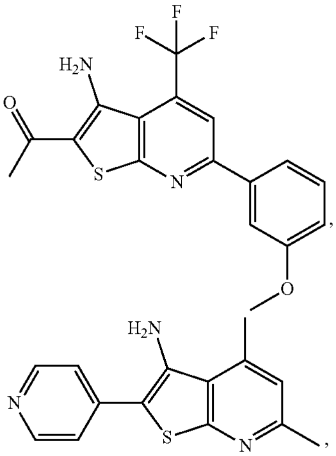
,
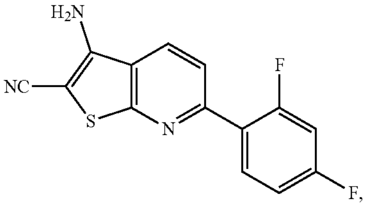
,
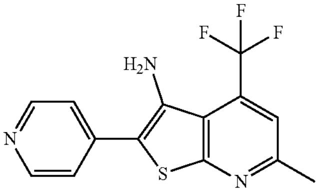
,
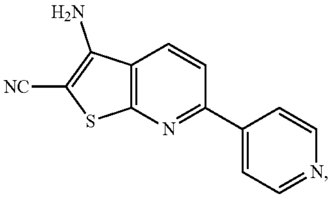
,
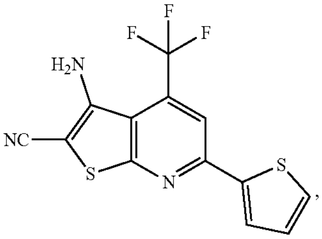
,
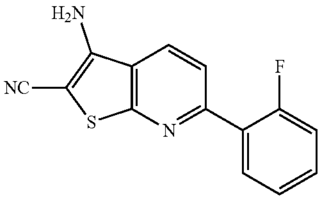
,
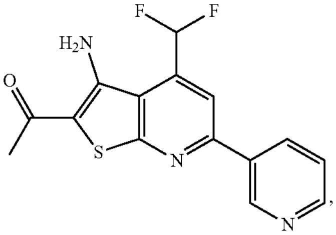
, -continued
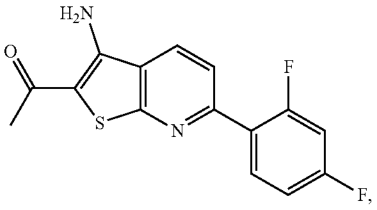
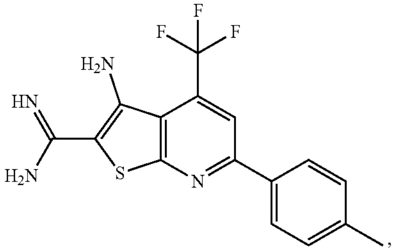
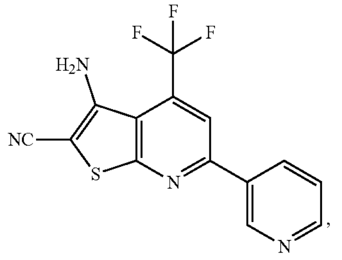
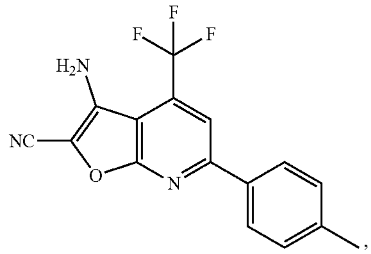
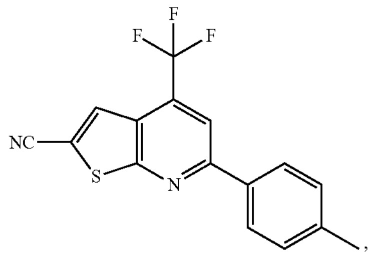
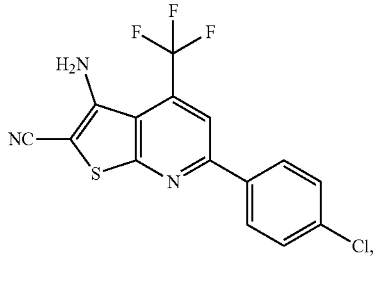
-continued
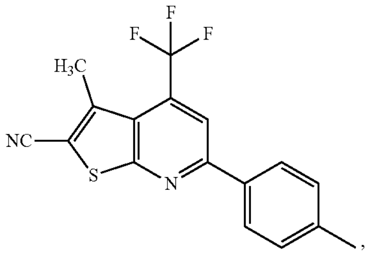
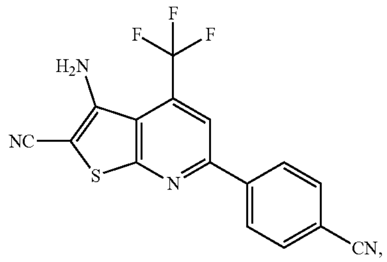
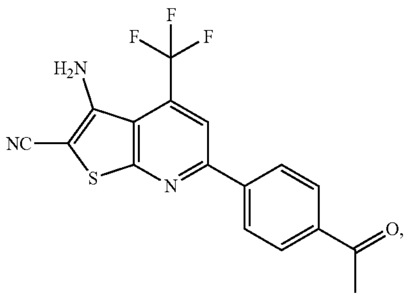
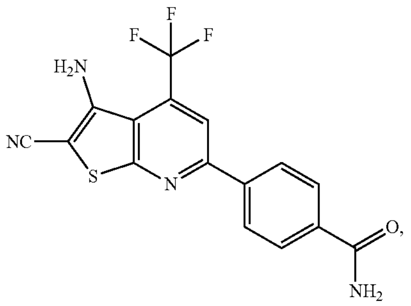
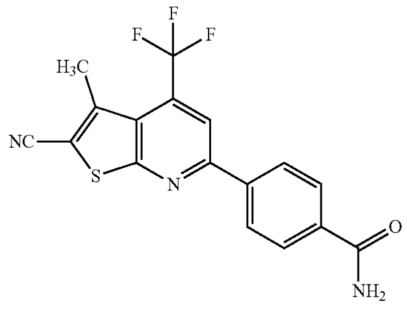

Also provided are the following compounds used in accordance with aspects and embodiments of the invention:

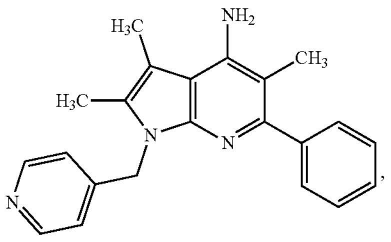

(herein desiganted LW23)

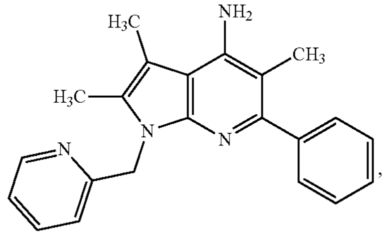

(herein desiganted LW24)

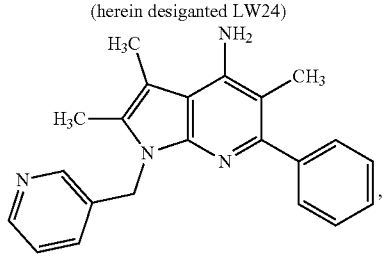

(herein desiganted LW 25)

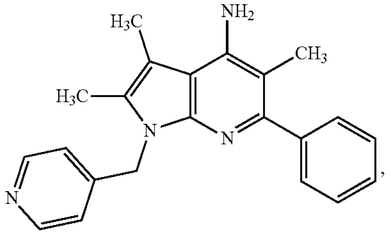

(herein desiganted LW 26)

In some embodiments, the aforementioned compounds are used in methods of the invention, as disclosed.

The invention further provides a formulation comprising at least one compound according to the invention (namely any compound mentioned herein or disclosed herein in Formula (I) or Formula (II)).

In some embodiments, the formulation is for topical use.

In some embodiments, the formulation is intended for reducing, arresting or diminishing at least one skin side effect or toxicity associated with at least one drug, as disclosed herein.

In some embodiments, the formulation is a pharmaceutical formulation comprising an effective amount or a dilutable amount of the at least one compound. In some embodiments, the at least one compound is carried (in solution, dispersion or suspension form) in at least one liquid or solid pharmaceutically acceptable carrier. The carrier may be selected to meet one or more desired formulation characteristics or one or more delivery modalities.

A formulation according to the invention may comprise an effective amount of the at least one compound to be topically delivered, said effective amount being suitable for purposes herein is determined by such considerations as may be known in the art. The effective amount may be determined in appropriately designed clinical trials and the person versed in the art will know how to properly conduct such trials in order to determine the effective amount.

The dosage regimen may vary depending upon known factors such as the particular material, the subject's age, sex, health, medical condition, and weight; the nature and extent of the symptoms to be expected and prevented; the kind of concurrent treatment: the frequency of treatment. Compounds utilized in accordance with the present invention may be administered in a single daily dose, or the total daily dosage may be administered in divided doses of two, three, or four times daily.

In some embodiments, topical formulations utilized in accordance with the invention may comprise one or more active or inactive materials which may be cosmetically acceptable or pharmaceutically acceptable. Such materials may be selected from anti-cancer agents, immunomodulators, anti-allergic agents, antifungal agents, antibiotics, steroids, pain relievers, cytoprotective agents, and combinations thereof.

The invention further provides a topical hair-follicle penetrating formulation, the formulation comprising a compound of formula (I) and a carrier:

(I)

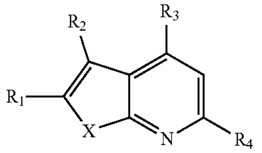

wherein each of the variants and each of the embodiments relating thereto is as disclosed above.

In some embodiments, the compound is selected from:

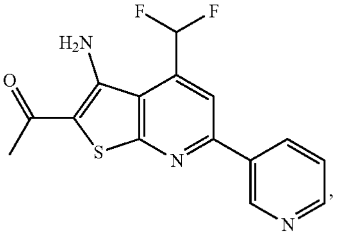

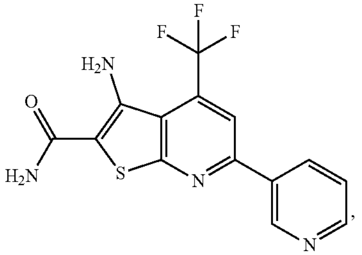

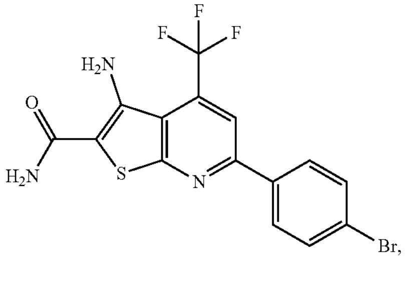

-continued
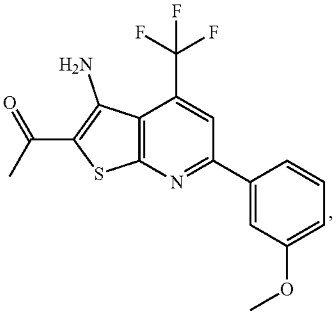
,
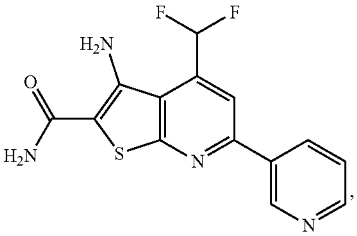
,
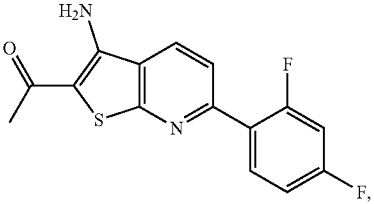
,
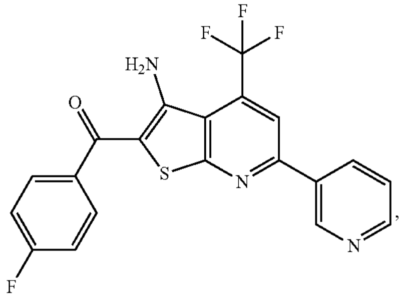
,
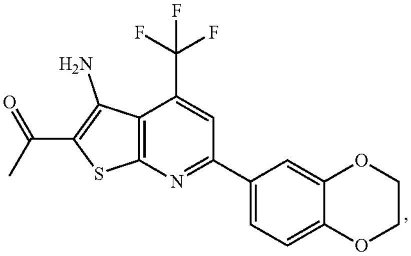
,
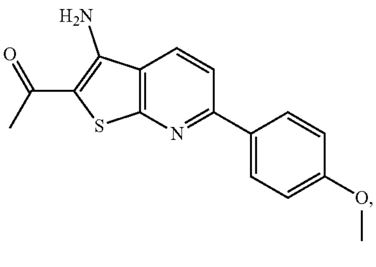
,
-continued
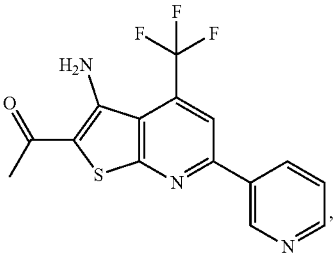
,
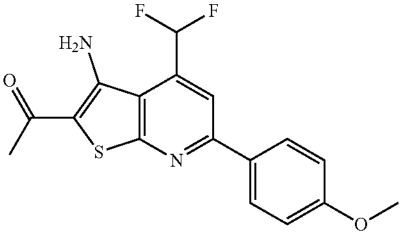
,
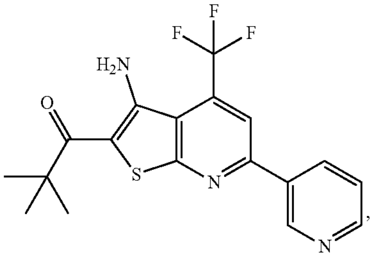
,
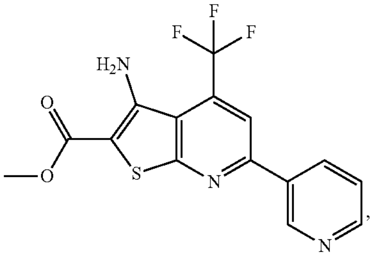
,
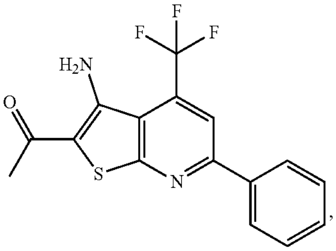
,
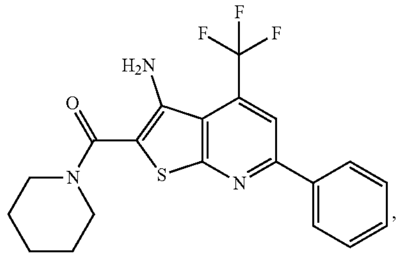
, -continued
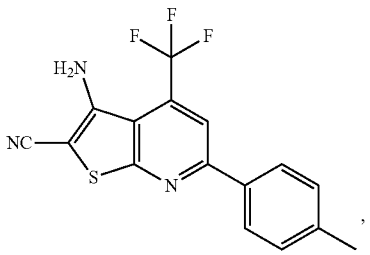
,
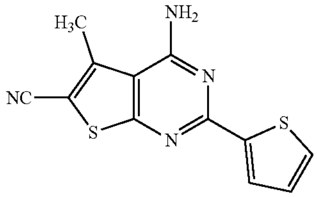
,
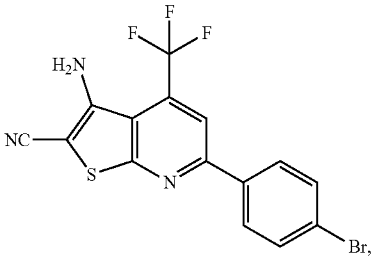
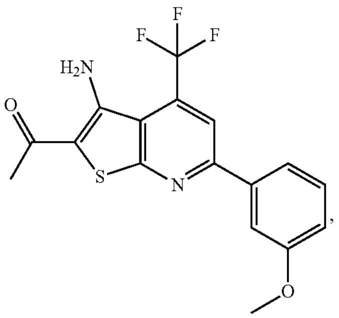
,
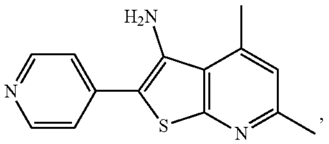
,
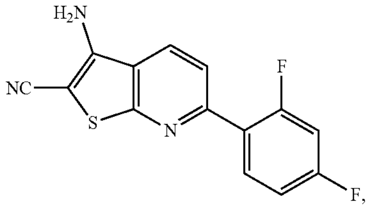
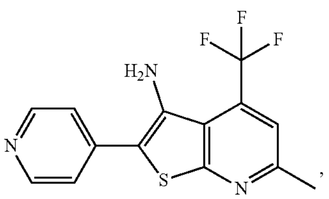
,
-continued
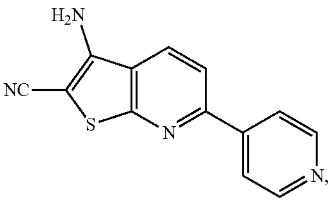
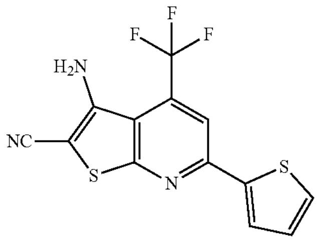
and
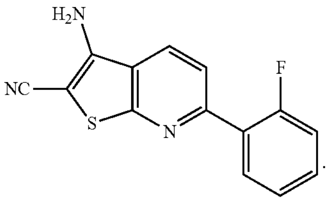
Also provided is a topical hair-follicle penetrating formulation, the formulation comprising a compound of formula (II) and a carrier:
(II)
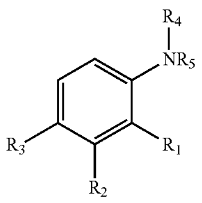
wherein each of the variants and each of the embodiments relating thereto is as disclosed above.
In some embodiments, the compound is selected from:
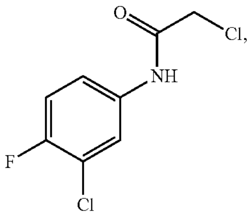
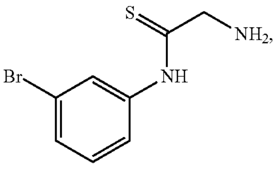
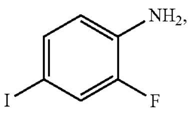
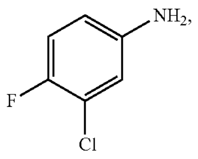

-continued

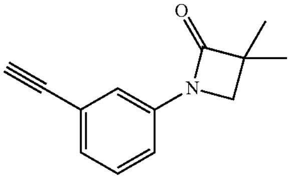

and

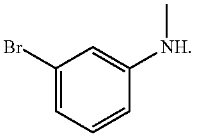

In some embodiments, the compound is any one of.

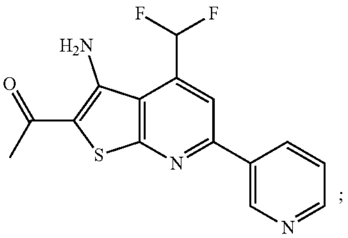

1-[3-amino-4-(difluoromethyl)-6-(3-pyridinyl)thienol[2,3-b]pyridin-2-yl]ethanone (herein referred to as compound G4)

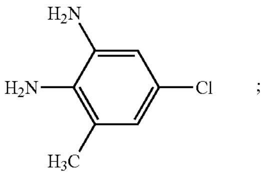

(2-amino-4-chloro-6-methylphenyl) amine hydrochloride (herein refered to as compound E3, as free base or as a salt form, e.g., salt of HCl)

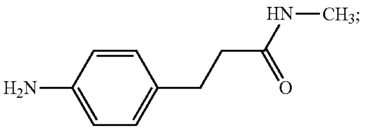

3-(4-aminophenyl)-N-methylpropanamide

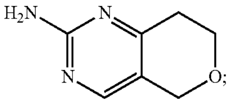

7,8-dihydro-5H-pyrano[4,3-d]pyrimidin-2-amine

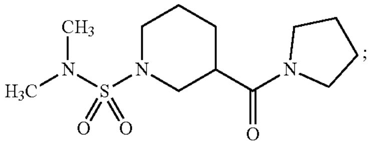

N,N-dimethyl-3-(1-pyrrolidinylcarbonyl)-1-piperidinesulfonamide

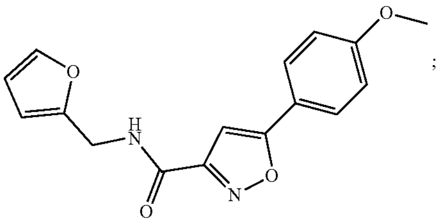

N-(2-furylmethyl)-5-(4-methoxyphenyl)-3-isoxazolecarboxamide

-continued

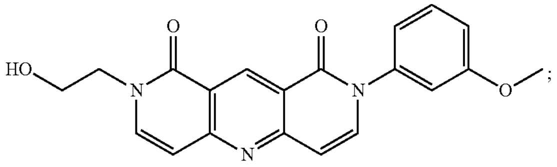

2-(2-hydroxyethyl)-8-(3-methoxyphenyl)pyrido[4,3-b]-1,6-naphthyridine-1,9(2H,8H)-dione

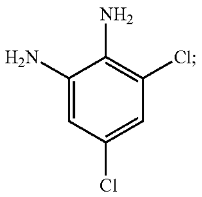

(2-amino-3,5-dichlorophenyl) amine

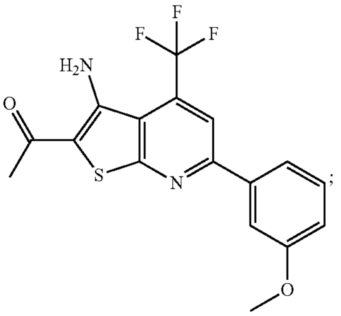

1-[3-amino-6-(3-methoxyphenyl)-4-(trifluoromethyl)thieno[2,3-b]pyridin-2-yl]ethanone

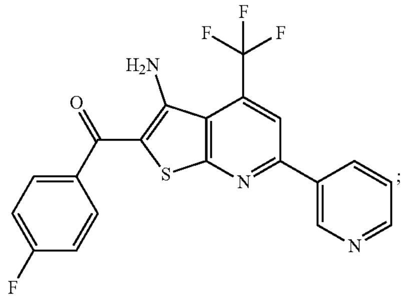

[3-amino-6-(3-pyridinyl)-4-(trifluoromethyl)thieno[2,3-b]pyridin-2-yl](4-fluorophenyl)methanone

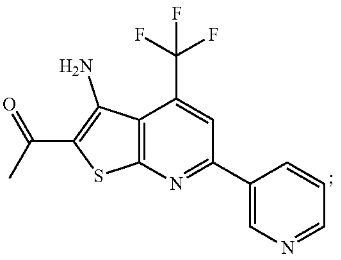

1-[3-amino-6-(3-pyridinyl)-4-(trifluoromethyl)thieno[2,3-b]pyridin-2-yl]ethanone -continued
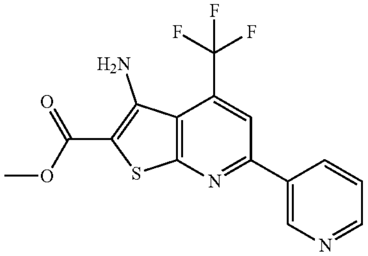
methyl 3-amino-6-(3-pyridinyl)-4-(trifluoromethyl)thieno[2,3-b]pyridine-2-carboxylate
and further a compound selected
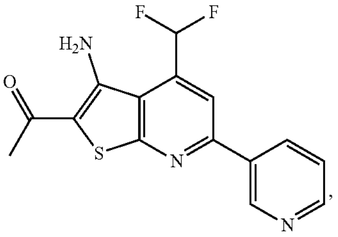
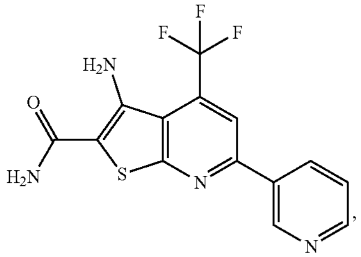
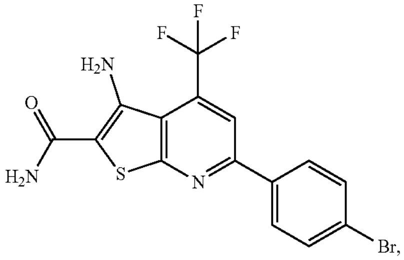
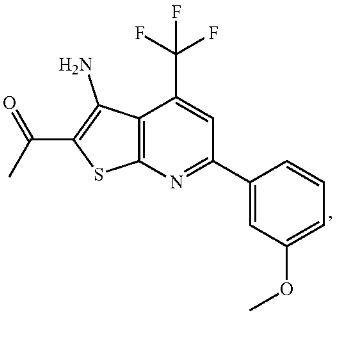
-continued
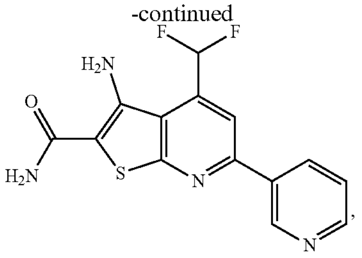
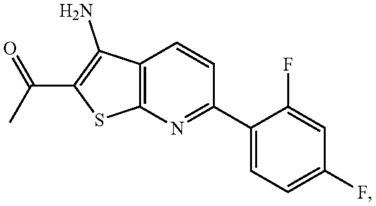
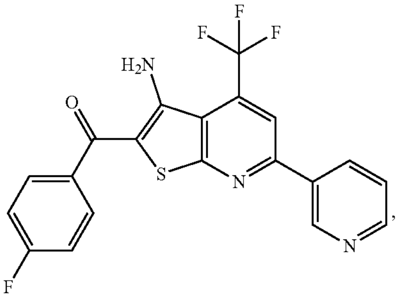
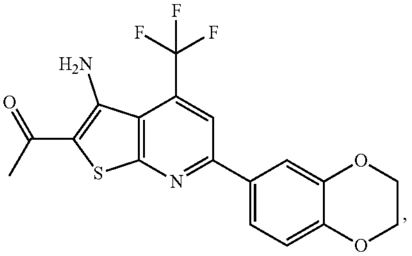
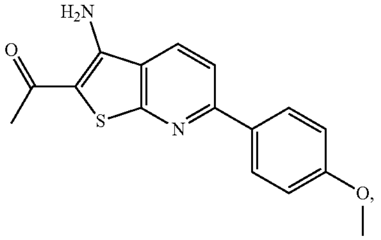
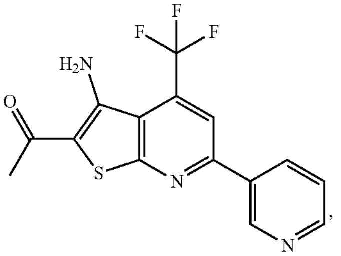
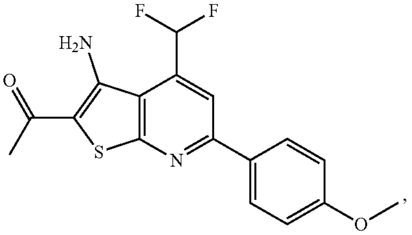

-continued
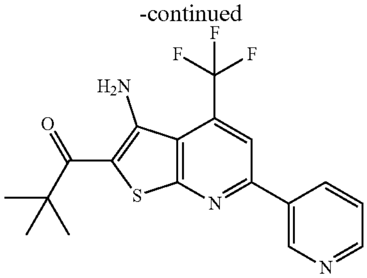
,
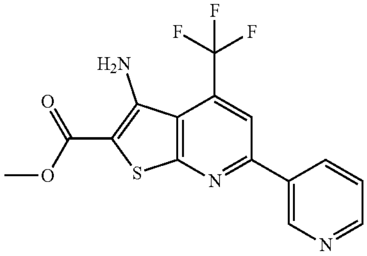
,
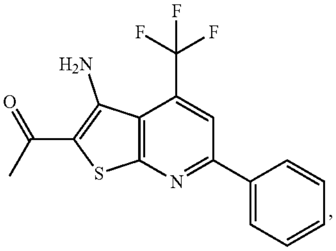
,
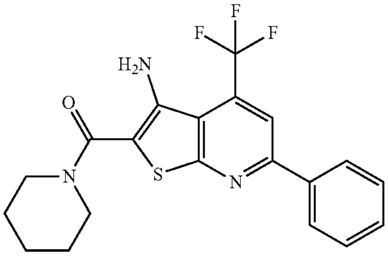
,
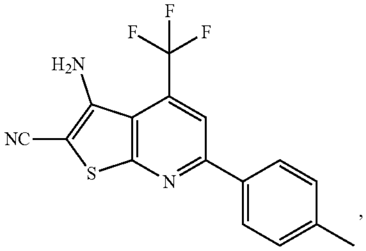
,
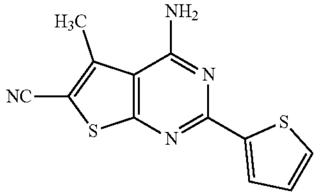
,
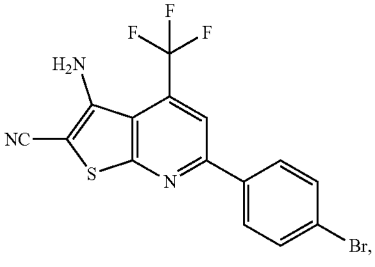
,
-continued
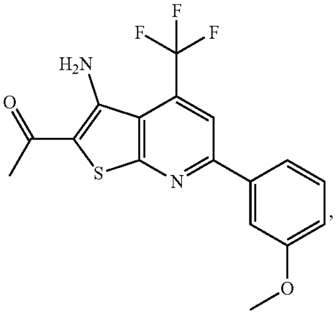
,
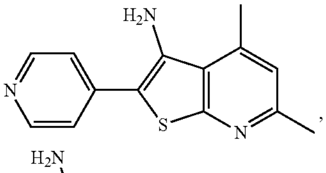
,
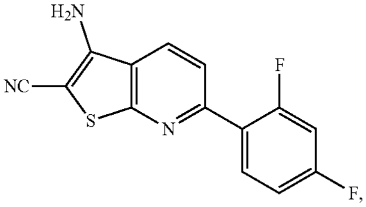
,
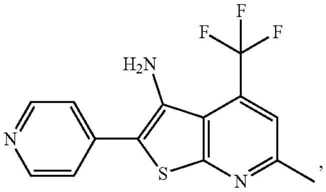
,
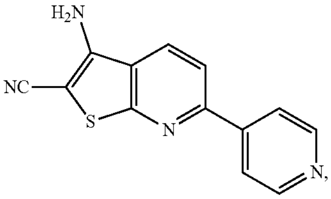
,
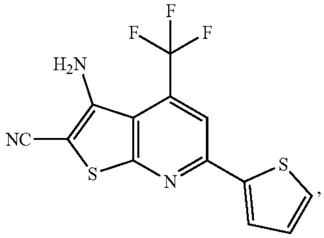
,
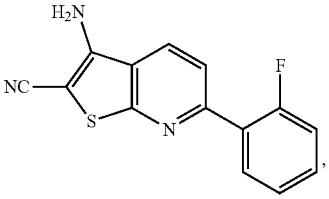
,
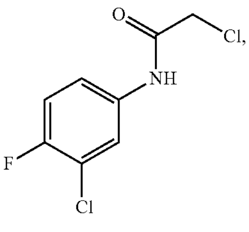
,
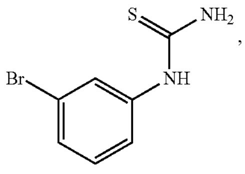
, -continued
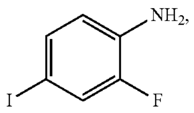
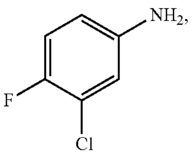
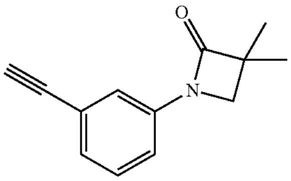
and
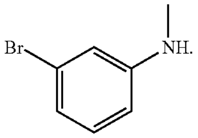
In some embodiments, the compound has a structure selected from:
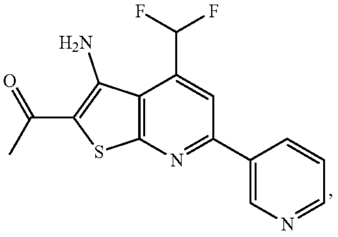
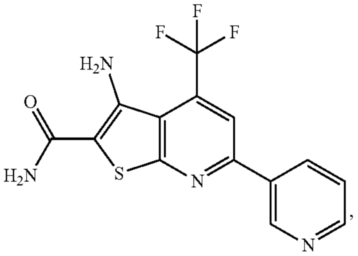
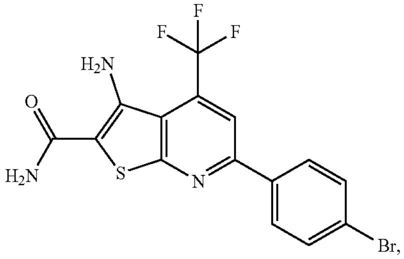
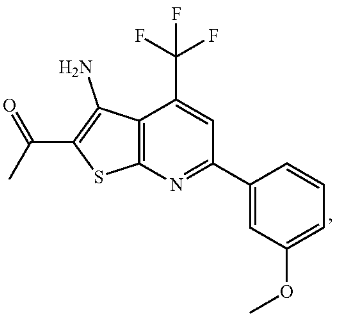
-continued
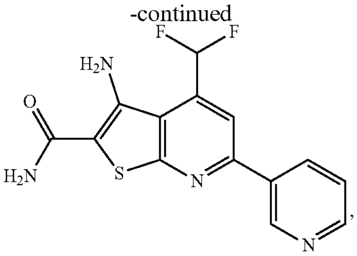
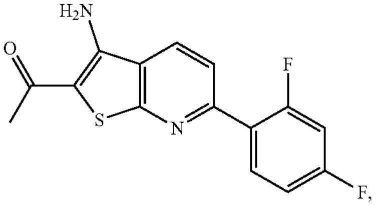
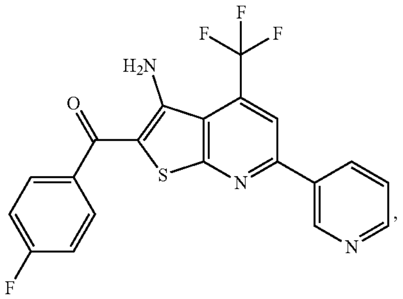
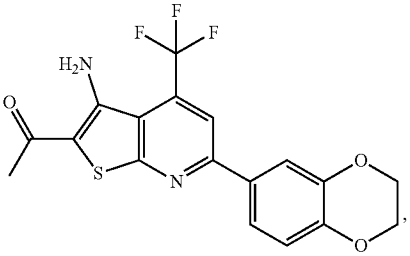
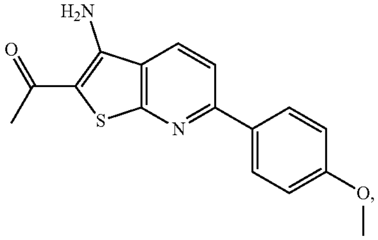
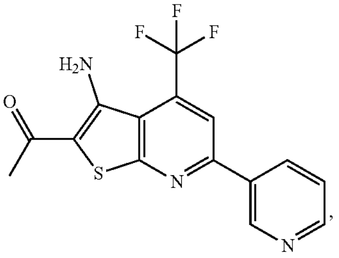
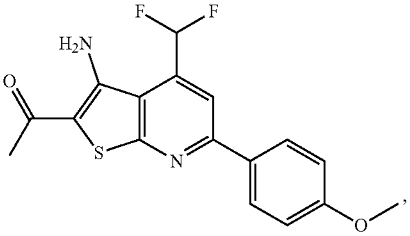

-continued
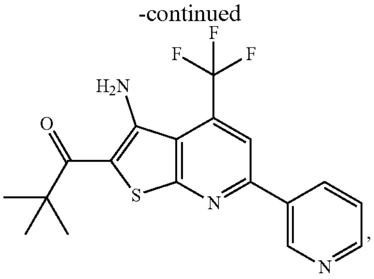,
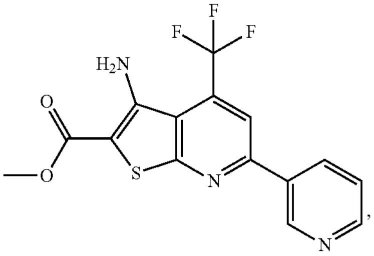,
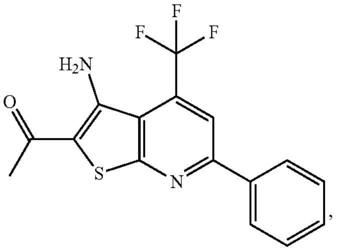,
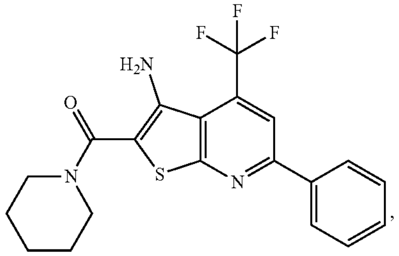,
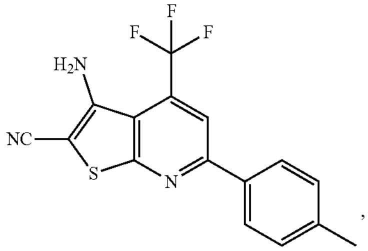,
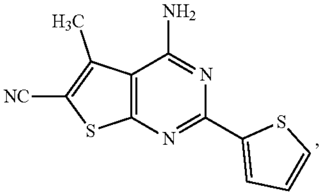,
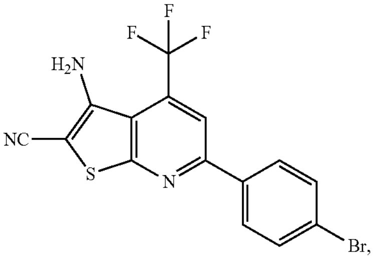,
-continued
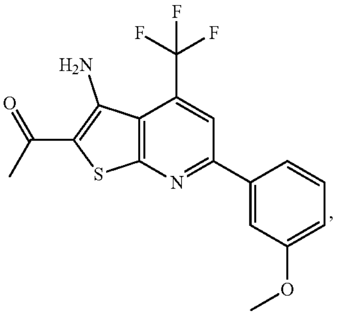,
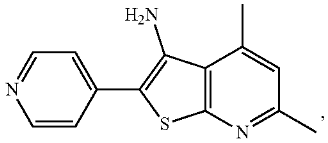,
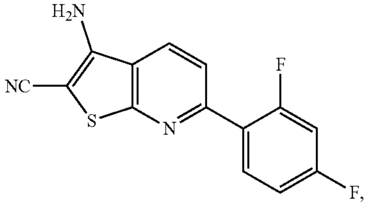,
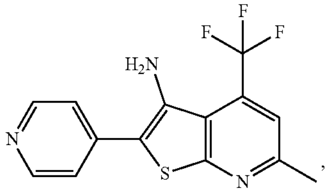,
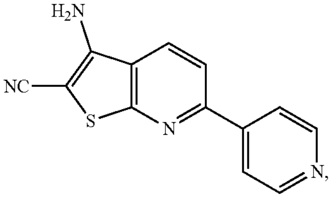,
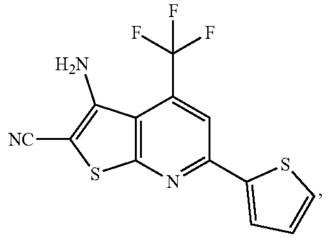,
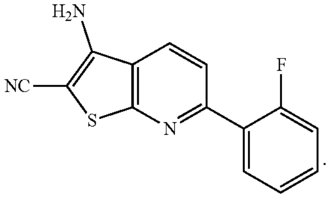.
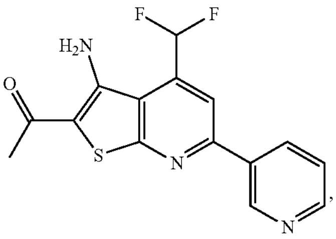, -continued
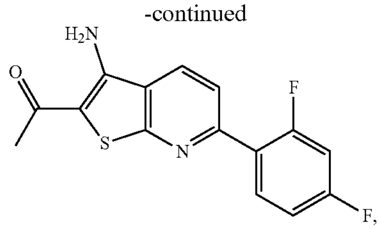
,
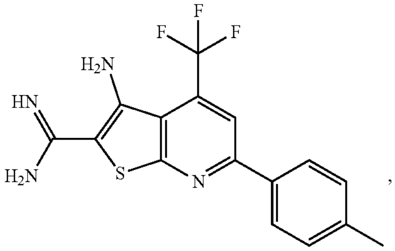
,
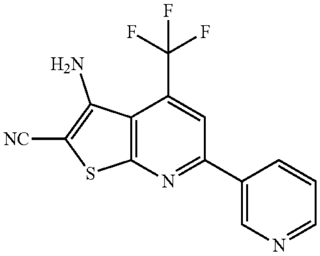
,
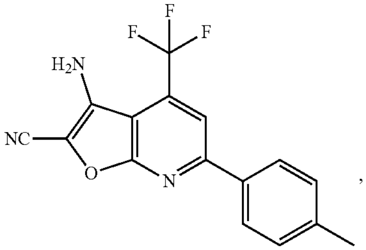
,
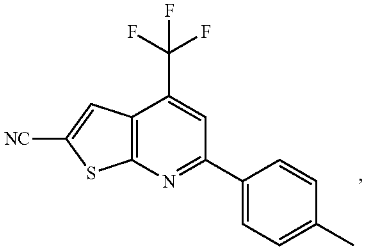
,
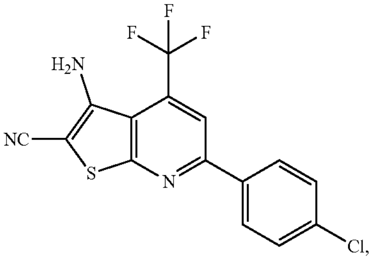
,
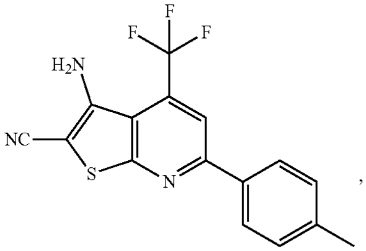
,
-continued
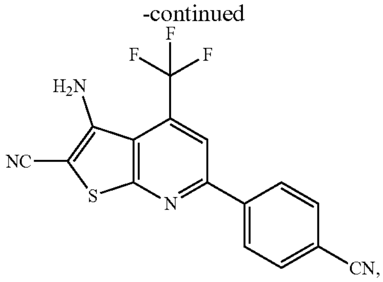
,
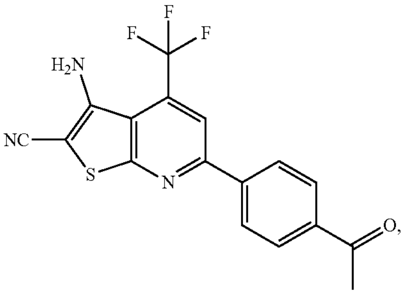
,
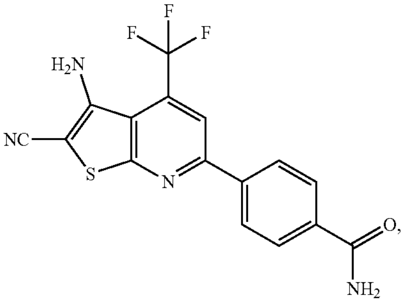
,
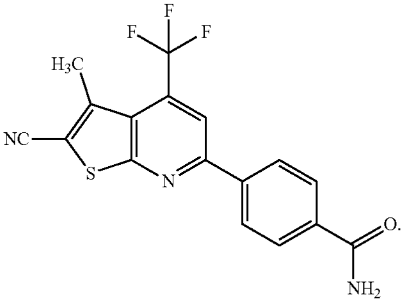
.
In some embodiments, the compound is LW11:
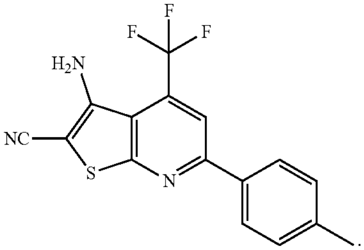 [SMILES: Cc1ccc(-c2cc(C(F)(F)F)c3c(N)c(C#N)sc3n2)cc1]
.
In some embodiments, the compound is provided in a form of a nanoparticle or a microparticle. The nanoparticle or a microparticle may be of a material selected from poly(L-lactide-co-glycolic acid)s (PLGA), poly(ethylene glycol)-polylactide (PEG-PLA), polycprolactone (PCL) and others.

In some embodiments, the compound is provided in nanoparticles having an average diameter of between 10 and 40 nm for PEG-PLA particles, between 50 and 150 nm for PLGA particles and between 300 and 500 nm for PCL particles.

In some embodiments, the compound is provided in a form of a nanoparticle or a microparticle.

In some embodiments, the compound penetrates the hair follicle into the deeper part of the epidermis; the pilosebaceous unit, the sebaceous glands and the hair bulb.

Due to the limitations of targeting the deep skin layers with free small molecules, special drug delivery systems should be developed in order to enhance penetration. Nanoparticles based system were designed and studied for efficient delivery and release of the drug into the pilosebaceous unit. To optimize the best system for follicular delivery, particles penetration capacity was studied using polymeric particles and metallic gold nanoparticles as model vehicles. In the polymeric particles optimal penetration was obtained with particles of size range of 100-200 nm. Biodegradable nanoparticles were fabricated with the ability to encapsulate and release small molecule compound into the hair follicles. Nanoparticles, labeled with 6-Coumarin as a fluorescent marker applied on human skin samples both in suspension or in ointment forms, showed superiority in delivery over the free compound. The nanocarriers are formulated into topical delivery system based on ointments and cream for maximal follicular accumulation.

Also provided are novel compounds used according to the invention, wherein each of the topically administrable compound disclosed herein, specifically or as part of formula (I) or (II) is a novel compound of the invention.

In some embodiments, the novel compound has a structure selected from:

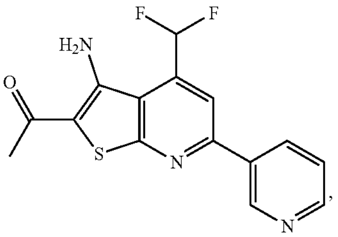
,

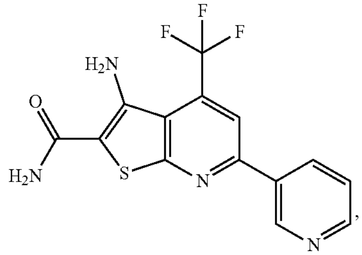
,

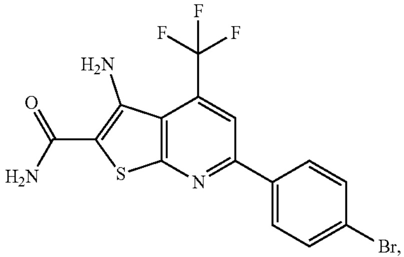
,

-continued

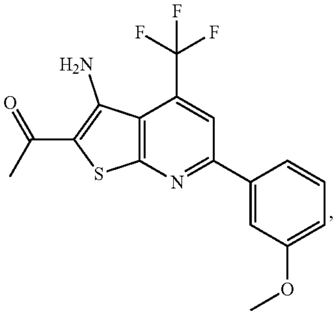
,

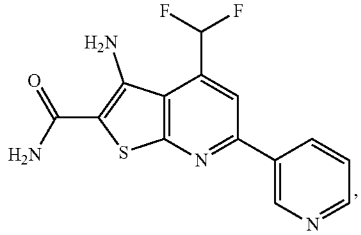
,

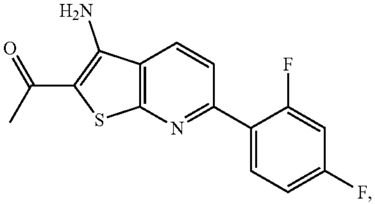
,

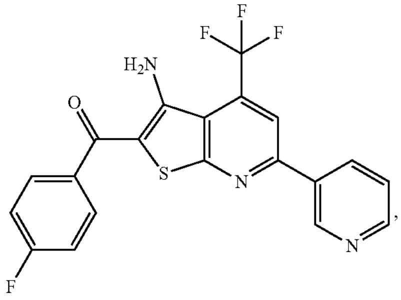
,

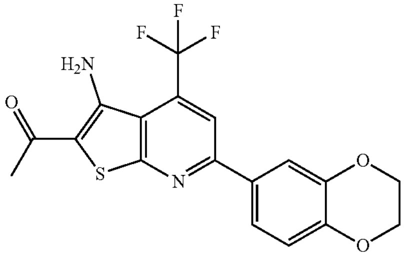
,

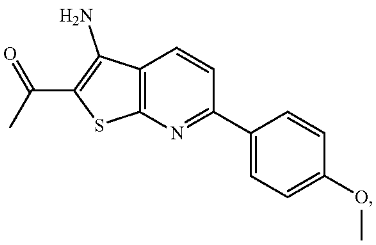
,

-continued
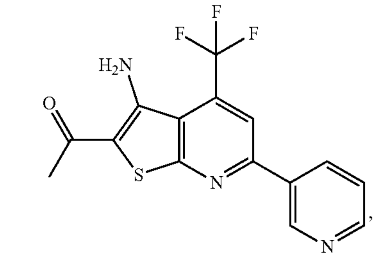
,
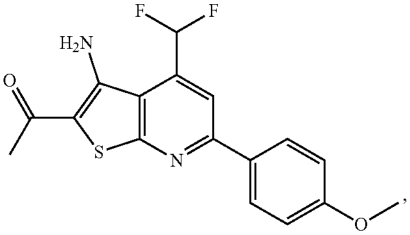
,
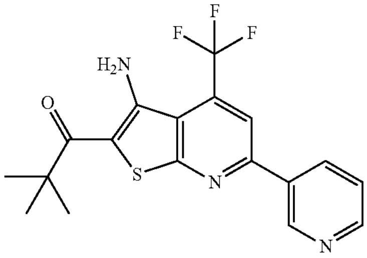
,
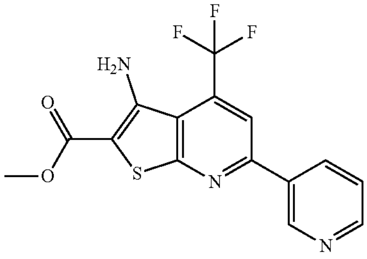
,
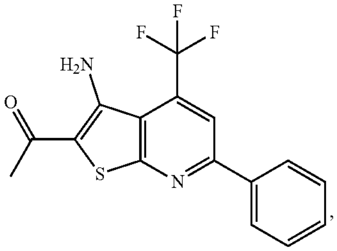
,
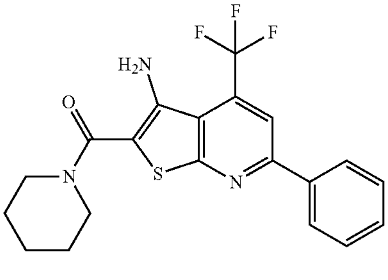
,
-continued
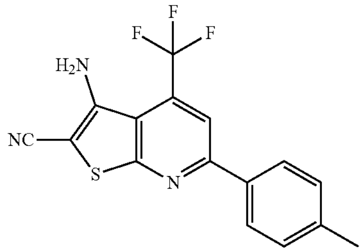
,
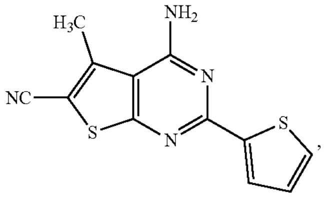
,
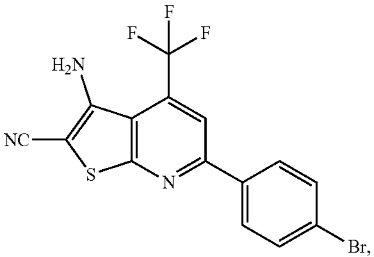
,
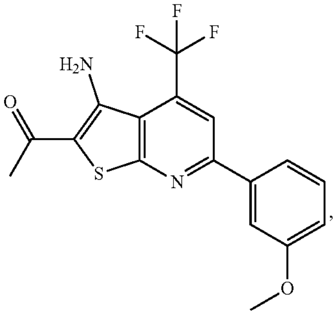
,
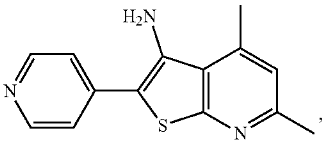
,
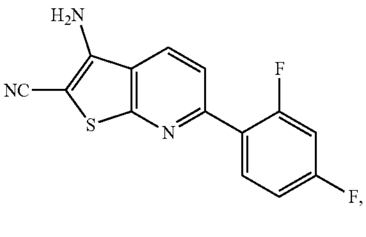
,
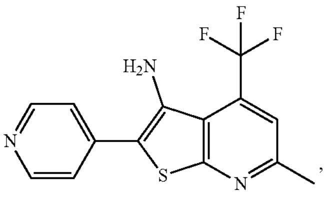
, -continued
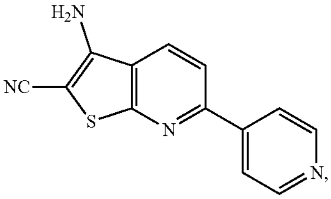
,
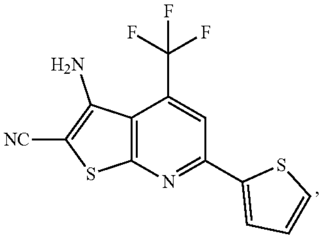
,
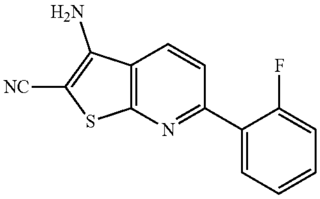
.
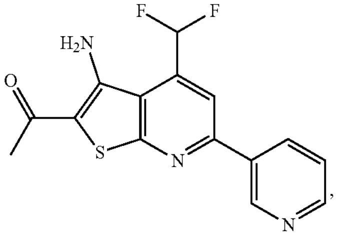
,
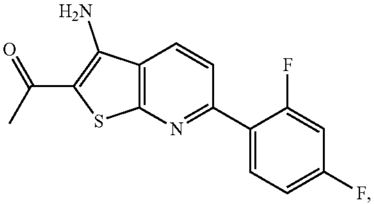
,
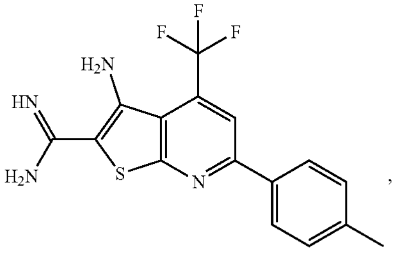
,
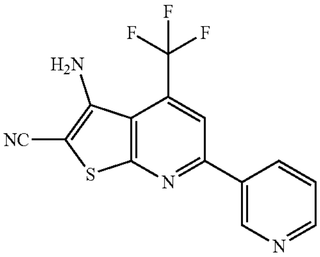
,
-continued
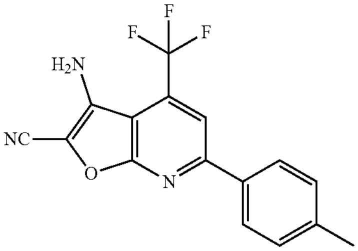
,
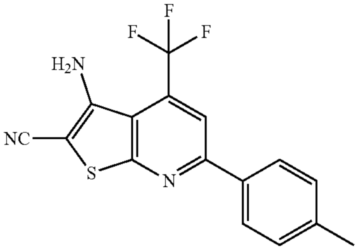
,
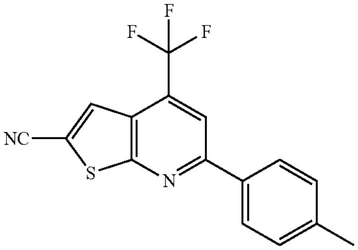
,
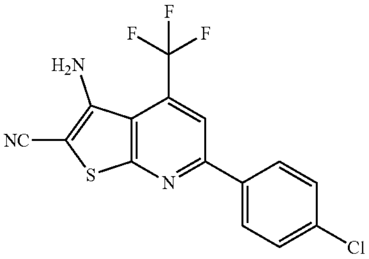
,
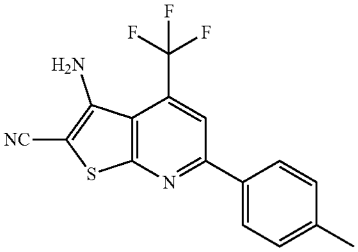
,
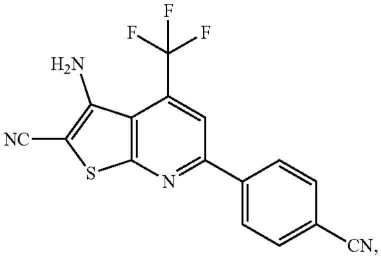
, -continued

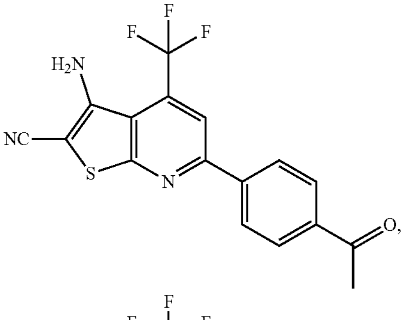

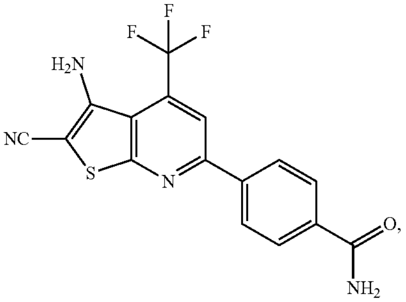

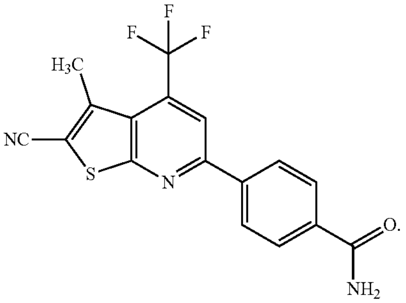

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 15A. Nanoparticles penetrate effectively into the hair follicles and sebaceous glands. FIG. 15B. Dispersed 6-coumarine in an ointment comprising soft paraffin (80%), liquid paraffin (10%) and wool fat (10%) (here in the "Hadassah ointment") as a control dose not penetrate through the SC.

DETAILED DESCRIPTION OF EMBODIMENTS

Figure 1A:
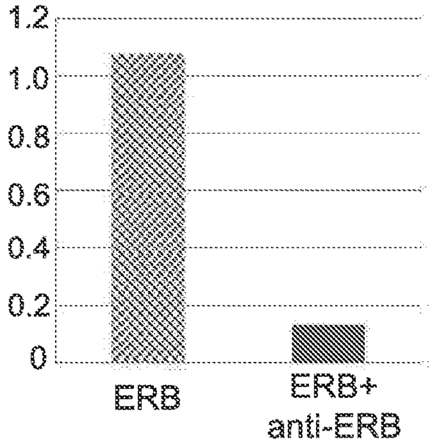
FIGS. 1A-D demonstrate the effect of cetuximab and anti-cetuximab on a human HaCaT cell line.
Figure 1B:
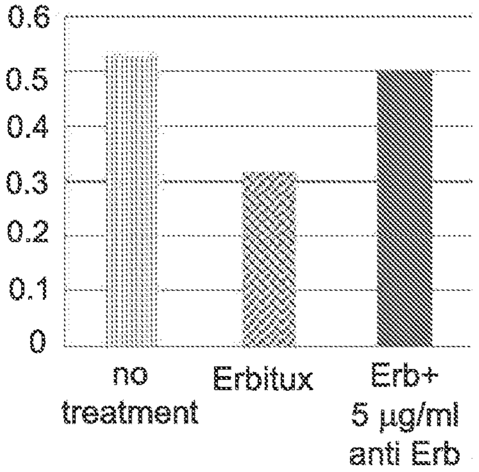
Figure 1C:
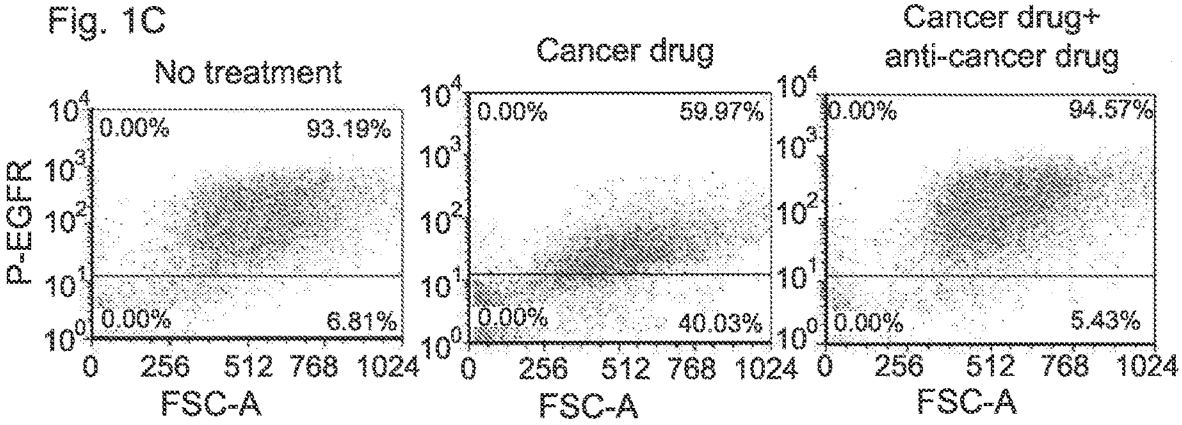
Figure 1D:
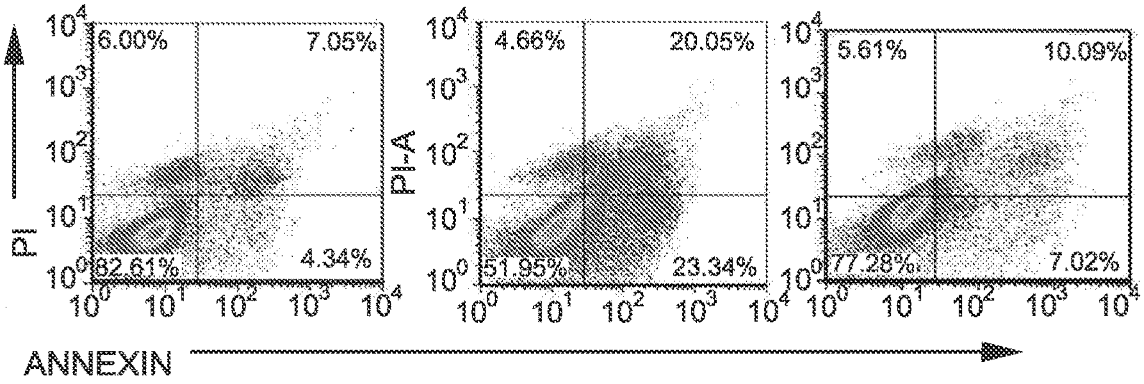

The novel approach proposed by the invention is to specifically target and block the effect of the anti-neoplastic biological targeted agents in the skin. Cetuximab and panitumumab are known monoclonal antibodies that block EGFR. The effect of cetuximab and panitumumab on HaCaT and A431 cell lines was studied. FIG. 1A shows by ELISA that the anti-erbitux mAb blocks the binding of cetuximzb to EGFR. FIG. 1B shows that by blocking the ability of cetuximab to bind to the target receptor the inventors have reversed the damage to keratinocytes shown by improved proliferation using an MTT assay, elevated levels of p-EGFR receptor FIG. 1C. Improved viability shown in FIG. 1D by flow cytometry PI Annexin staining in which the percentage of apoptotic keratinocytes returns to baseline level when treated by cetuximab and anti-cetuximab monoclonal antibody.

In order to apply this approach topically there is a need to find a molecule that blocks binding of EGFR inhibitory monoclonal antibodies to EGFR, but also possesses characteristics that allow its penetration to the epidermis (e.g., molecular weight under 500 dalton). A survey of 3000 small molecules (ChemBridge Corporation ltd.) was performed using an ELISA assay, revealing compounds that repeatedly blocked binding of cetuximab to EGFR in a dose-dependent manner (FIG. 2).

Figure 2A:
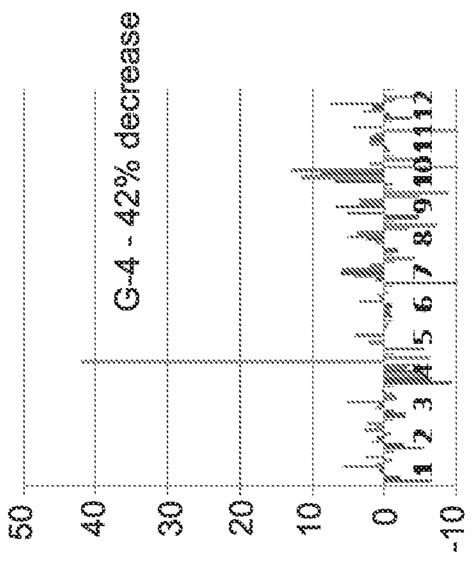
FIGS. 2A-D demonstrate LW11 G4, E3 and molecules block binding of cetuximab to EGFR.
Figure 2B:
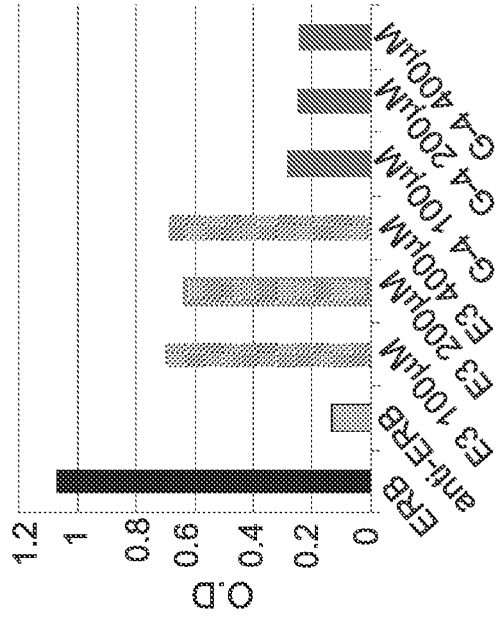
Figure 2C:
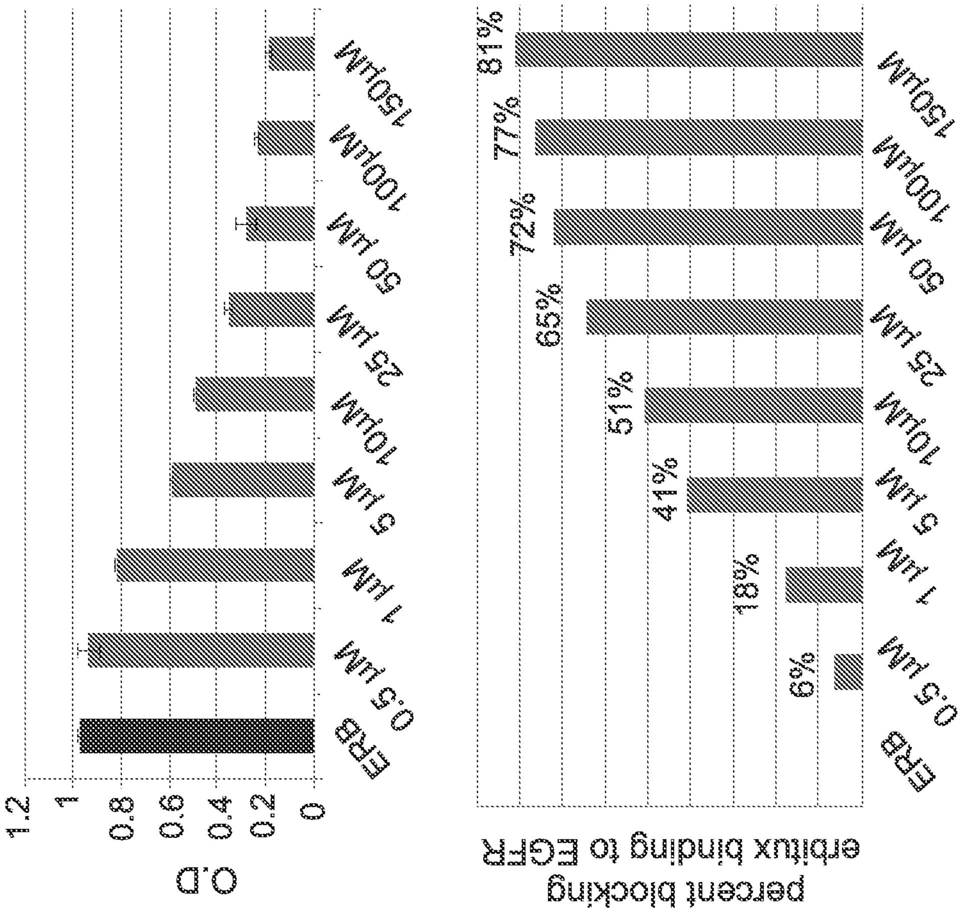

FIG. 2A is an example of screening plate showing sample G4 blocking 42% binding of cetuximab to EGFR. FIG. 2B demonstrates blocking of cetuximab binding to EGFR by G4 and E3 compounds compared to anti-cetuximab [anti-ERB] monoclonal antibody used as control. FIG. 2C shows dose response curve for blocking effect of G4.

Figure 2D:
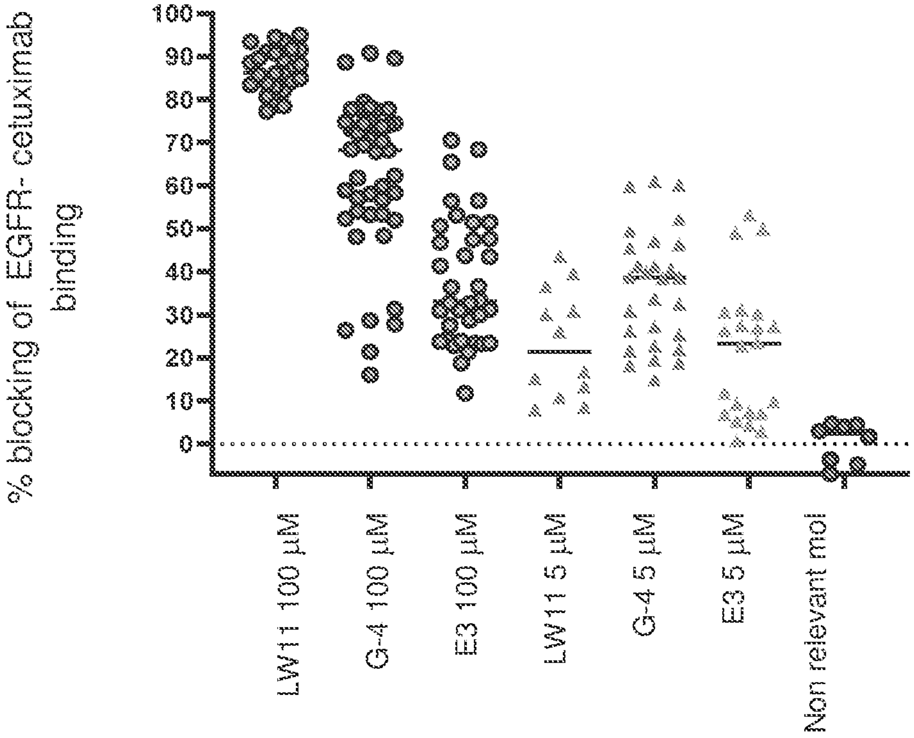

Using an ELISA assay, the blocking of cetuximab binding to EGFR by G4 and E3 and LW11 (G4 derivative) compounds was further used and demonstrated in a dose-dependent manner (FIG. 2D, independent experiments performed in triplicates)

Figure 3:
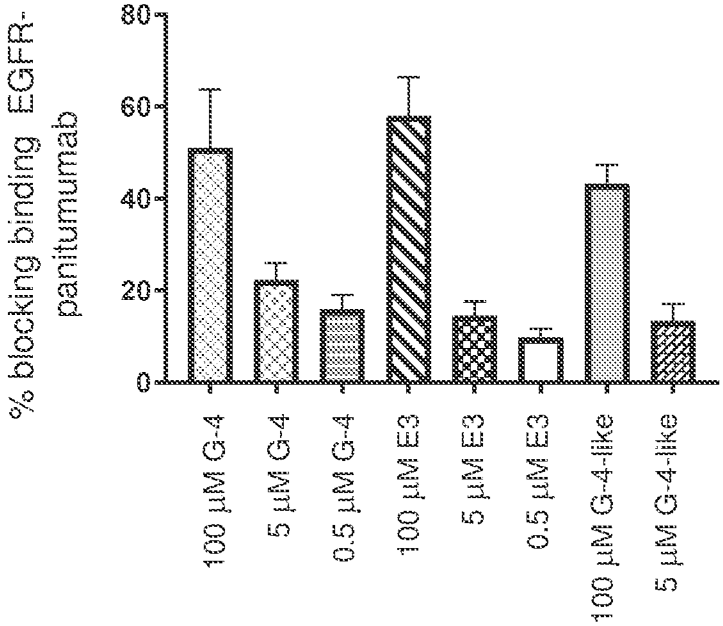
FIG. 3 demonstrates G4, and E3 and G4-L molecules block binding of panitumumab (vectibix) to EGFR.

As depicted in FIG. 3, both E3 and G4 molecules block the binding of another human monoclonal antibody specific to the epidermal growth factor receptor—panitumumab (vectibix).

Figure 4:
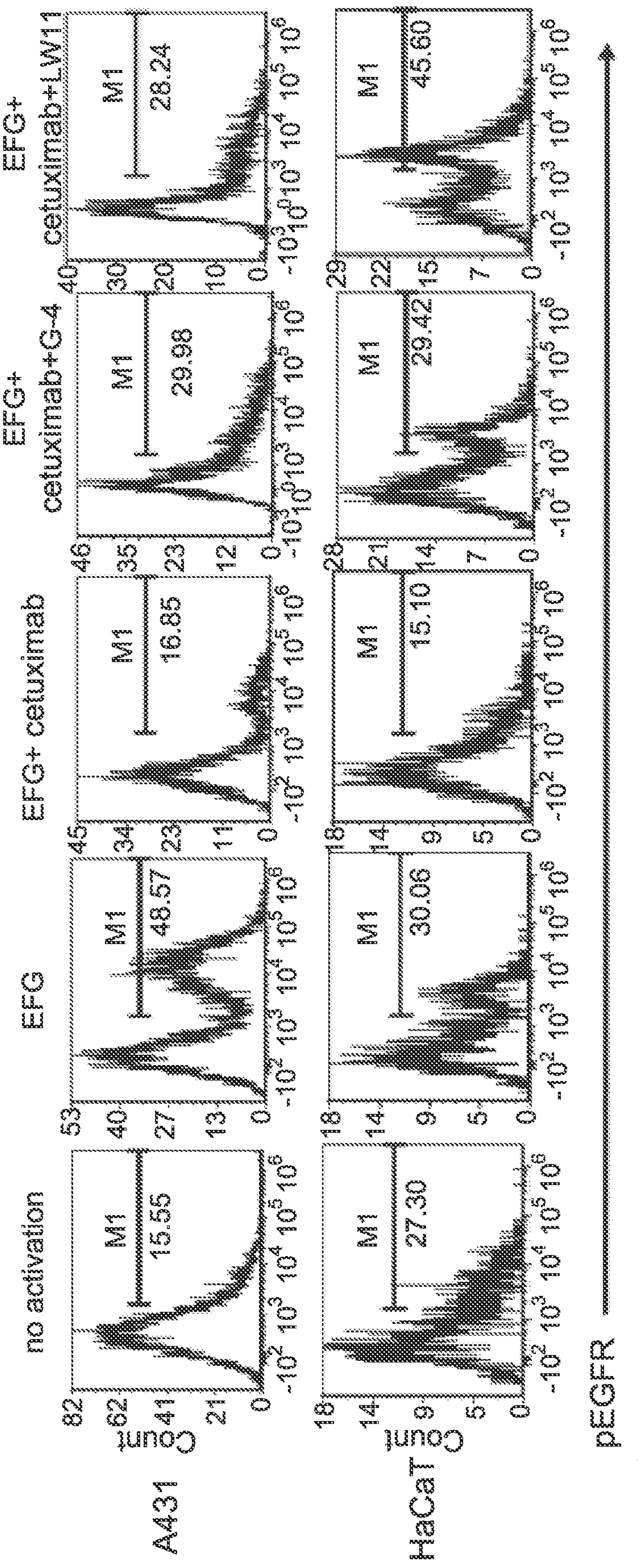
FIG. 4 demonstrate increase in p-EGFR by blocking cetuximab's binding to the target receptor with G4 molecule.
Figures 5A, 5B, 5C:
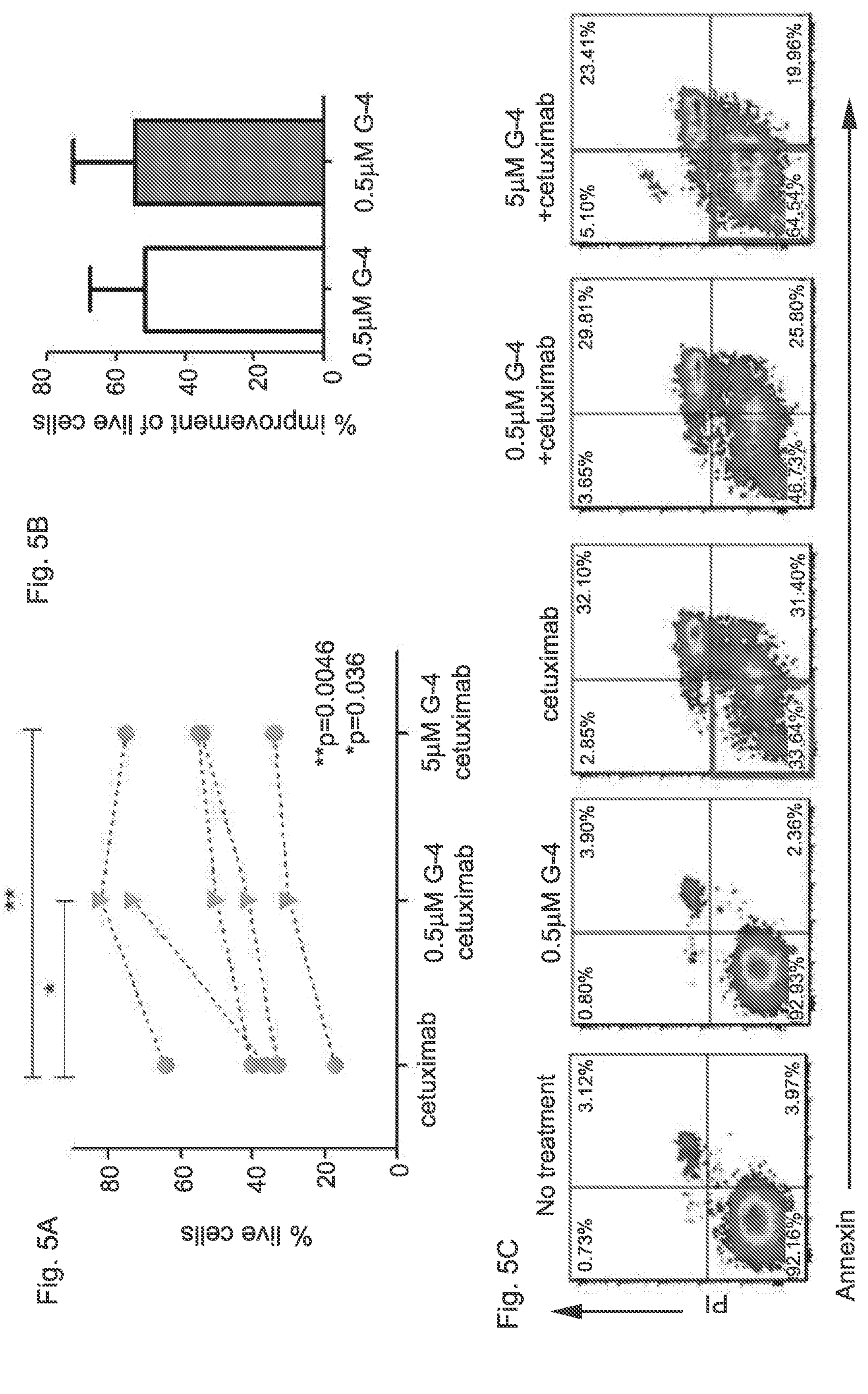
FIGS. 5A-F demonstrate that G-4 protects A431 and HaCaT cell lines from cetuximab induced cell death. EGFRi cetuximab induces death in keratinocytes.
Figures 5D, 5E, 5F:
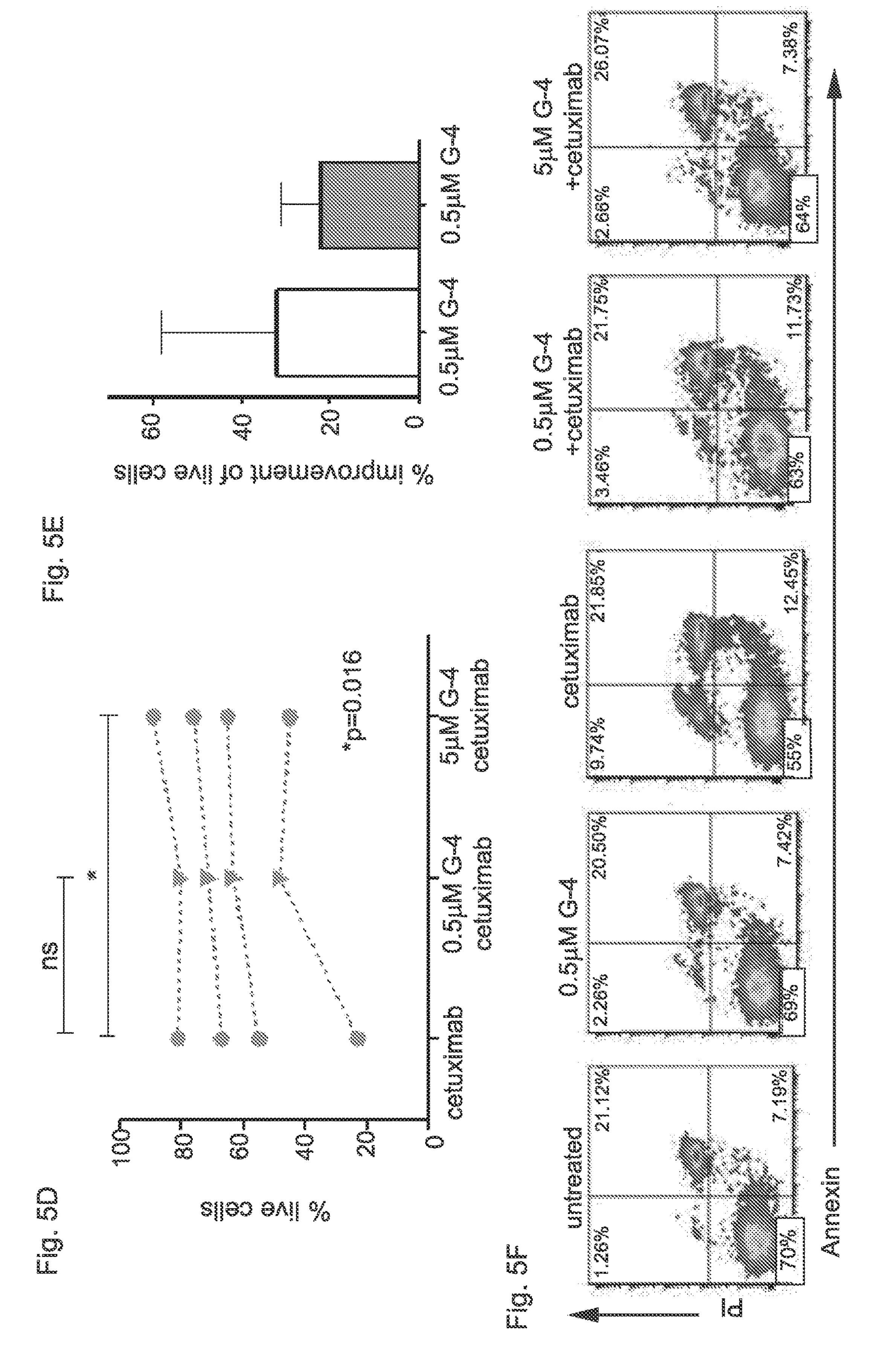

As shown in FIG. 4, G-4 and LW11 increase p-EGFR expression on A431 cells and HaCaT cells treated with cetuximab. A431 and HaCaT cells were treated for 20 minutes with i) 150n/ml EGF. ii) EGF and 5ug/ml cetuximab and iii) EGF cetuximab and 5 uM G-4 or LW11. The level of phosphorylated EGFR receptor was measured in cell lines by flow cytometry. Activated levels of p-EGFR in A431 and HaCaT cells dropped from 48.5% to 16.8% and from 30% to 15% respectively when cetuximab was added. Both G-4 and LW11 were able to reverse the toxic effect of cetuximab on EGFR with p-EGFR levels rising to almost 30% in A431 cells and up to 46% in HaCaT cells treated with cetuximab and LW11.

FIGS. 5A-F demonstrate that G-4 protects A431 and HaCaT cell lines from cetuximab induced cell death. EGFRi cetuximab induces death in keratinocytes. To test if G-4 compound protects keratinocyte from cetuximab induced death A431 and HaCaT cells were treated with cetuximab alone and with cetuximab+0.5 uM and 5 uM G-4 for 72 hours. Apoptosis and cell death were evaluated by annexin-V and propidium-iodide (PI) labeling, followed by flow cytometry. The experiments show improved cell viability of cell lines treated with G-4 and cetuximab as compared to cetuximab alone. A) Five independent experiments showing improved cell viability when adding G-4 compound to A431 cells treated with cetuximab. B) On average G-4 compound improved viability of A431 cell cetuximab induced cell death by more than 50%. C) Flow cytometry of one representative experiment showing elevation of percentage of live cells from 34.6% live cells after cetuximab verses 54.5% live cells after adding G-4 to cetuximab treatment. D) Four independent experiments showing improved cell viability when adding G-4 compound to HaCaT cells treated with cetuximab. E) On average G-4 compound improved viability of HaCaT cetuximab induced cell death by 30%. F) Flow cytometry of one representative experiment showing elevation of percentage of live cells from 55% live cells after cetuximab verses 64% live cells after adding G-4 to cetuximab treatment.

Figure 6A:
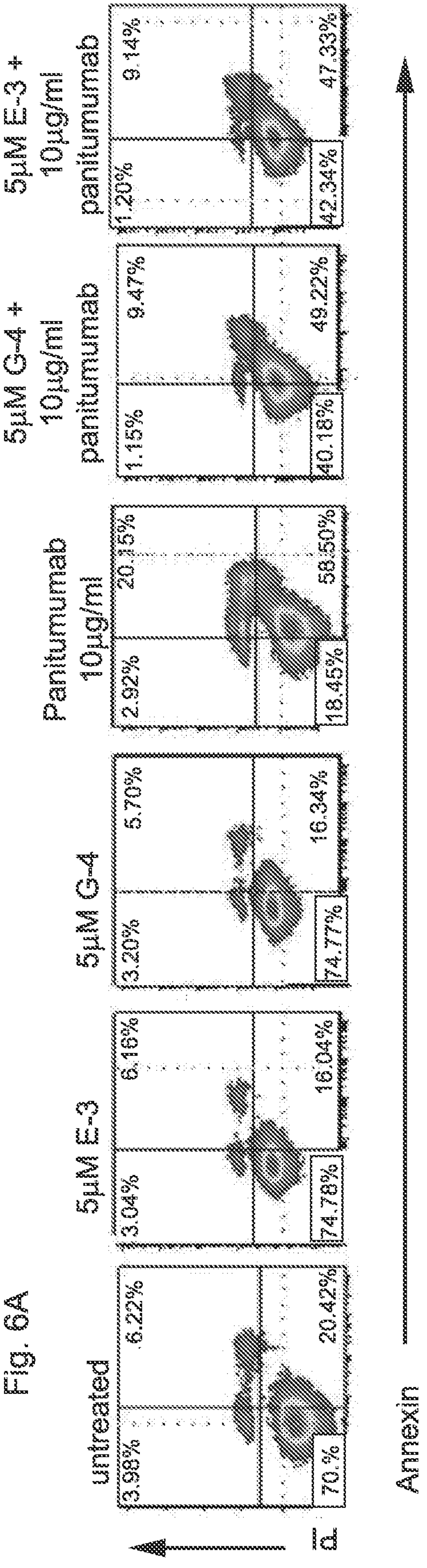
FIG. 6A-B demonstrate improved viability of keratinocytes by blocking panitumumab's binding to the target receptor with E3 and G4 molecules.
Figure 6B:
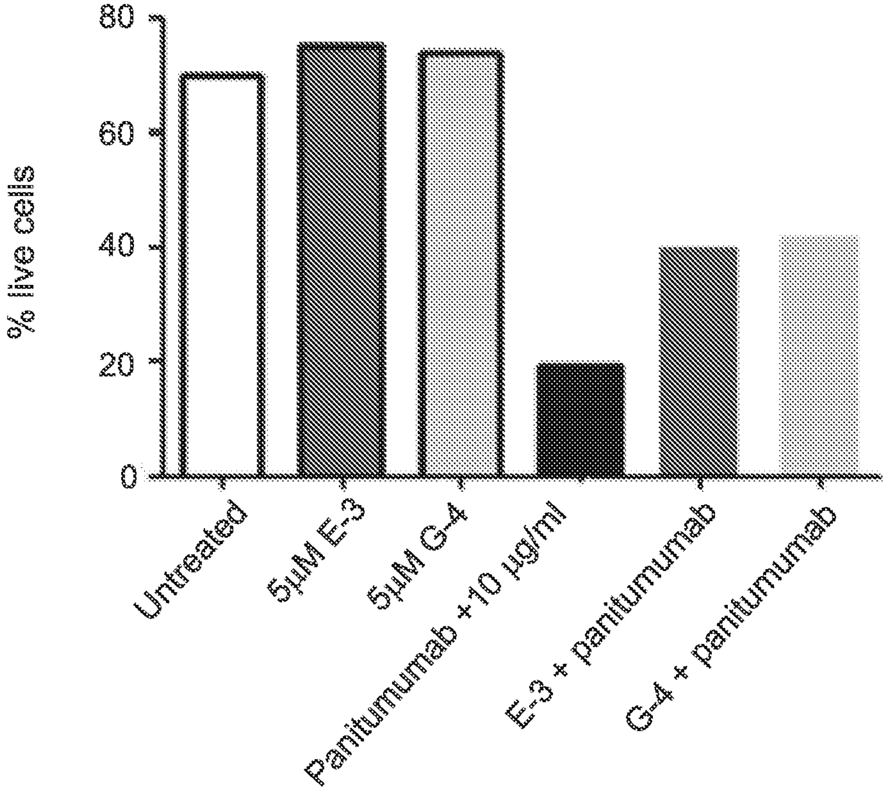

Blocking panitumumab's binding to the target receptor with E3 and G4 molecules also showed improved viability of keratinocytes, as shown by flow cytometry following PI Annexin staining of apoptotic cells in FIGS. 6A-B. To test if G-4 and E-3 compounds protect keratinocyte from panitumumab induced death we treated A431 cells with panitumumab alone and with panitumumab+0.5 uM and 5 uM G-4 and E-3 compounds for 72 hours. Apoptosis and cell death were evaluated by annexin-V and propidium-iodide (PI) labeling, followed by flow cytometry. The experiments show improved cell viability of A431 cells treated with G-4 and E-3 compounds with panitumumab as compared to panitumumab alone. A) flow cytometry of one representative experiment showing elevation of percentage of live cells from 18% live cells after panitumumab alone verses 40% live cells with panitumumab and G-4 compound and 42% live cells with E-3 compound and panitumumab treatment. B) bar graph depicting percent live A431 cells with the different treatment conditions.

Specific small molecules tyrosine kinase inhibitors (TKI's) block EGFR by binding to the adenosine triphosphate (ATP)-binding site of the enzyme. Thus, the function of the EGFR tyrosine kinase is inhibited. These drugs cause prominent and dose-limiting dermatologic complications.

Figure 7A:
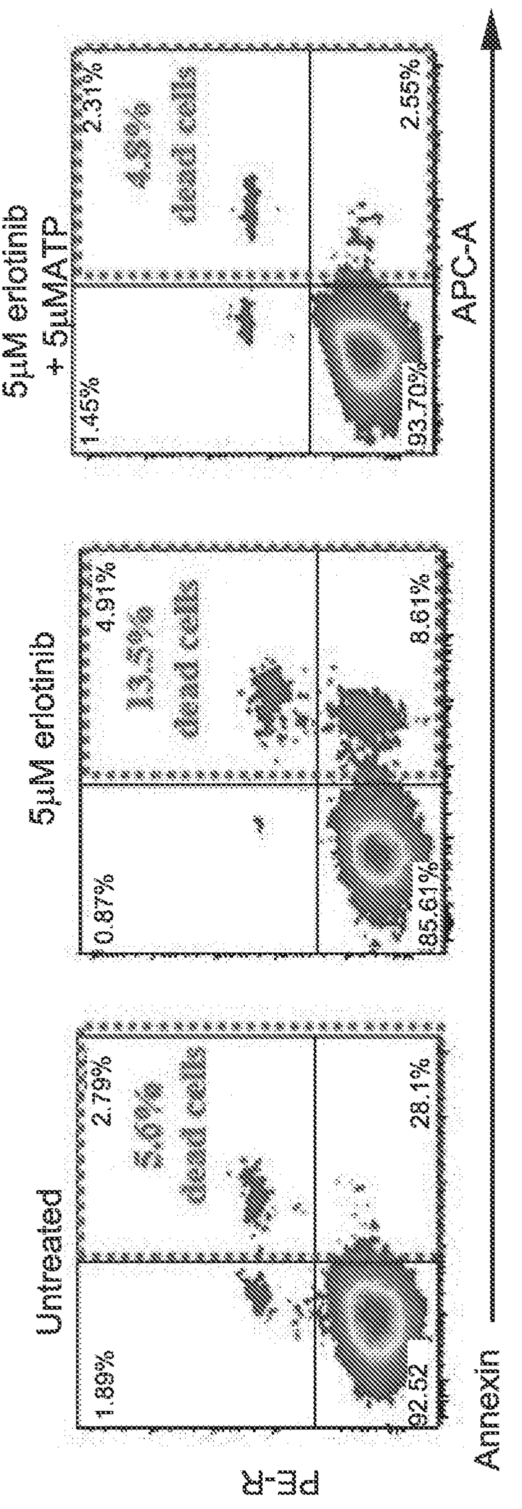
FIGS. 7A-B demonstrates reversal of the toxic effect of EGFRi tyrosine kinase inhibitors (TKI) erlotinib on HaCaT cell induced death by blocking the drug's activity on the ATPase using ATP analogs.
Figure 7B:
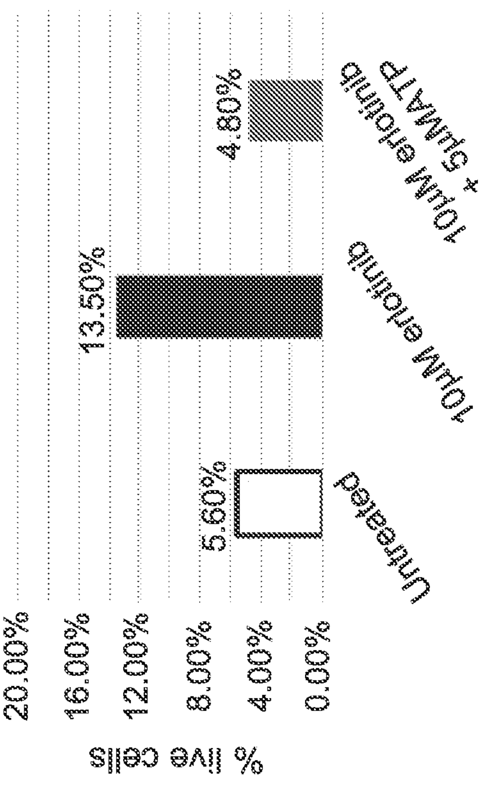

In order to specifically block the TKI's toxic effect on keratinocytes we first tested ATP analogues ability to compete with erlotinib and gefitinib blocking activity on the ATPase. FIGS. 7A-B demonstrate ATP analogues protection of HaCaT cells from erlotinib induced cell death. To test if ATP analogues can protect keratinocyte from erlotinib induced death we treated HaCaT cells with erlotinib alone and with erlotinib+5 uM ATP analogue for 72 hours. Apoptosis and cell death were evaluated by annexin-V and propidium-iodide (PI) labeling, followed by flow cytometry. The experiments show improved cell viability of HaCaT cells treated with ATP analogue and erlotinib as compared to erlotinib alone. A) flow cytometry of one representative experiment showing decreased percentage of dead cells from 13.5% dead cells after erlotinib alone verses 4.8% dead cells with erlotinib and ATP analogue. B) bar graph depicting percent dead HaCaT cells with the different treatment conditions.

Figure 8A:
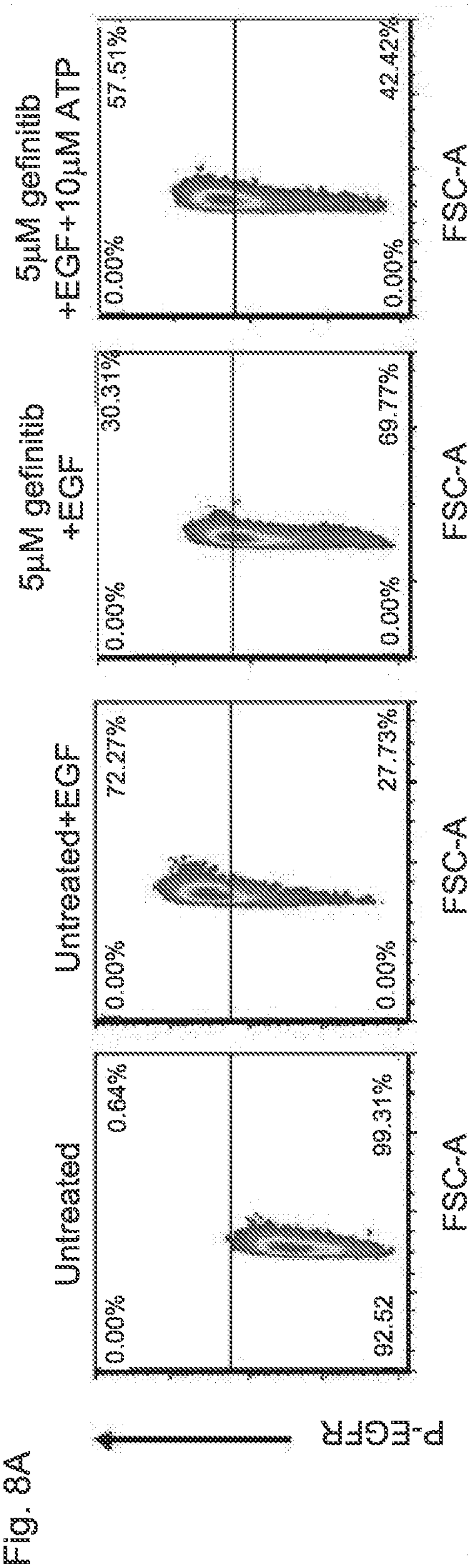
FIGS. 8A-B demonstrates reversal of the toxic effect of EGFRi tyrosine kinase inhibitors (TKI) gefitinib on A431 cells by elevating the p-EGFR expression using ATP analogs.
Figure 8B:
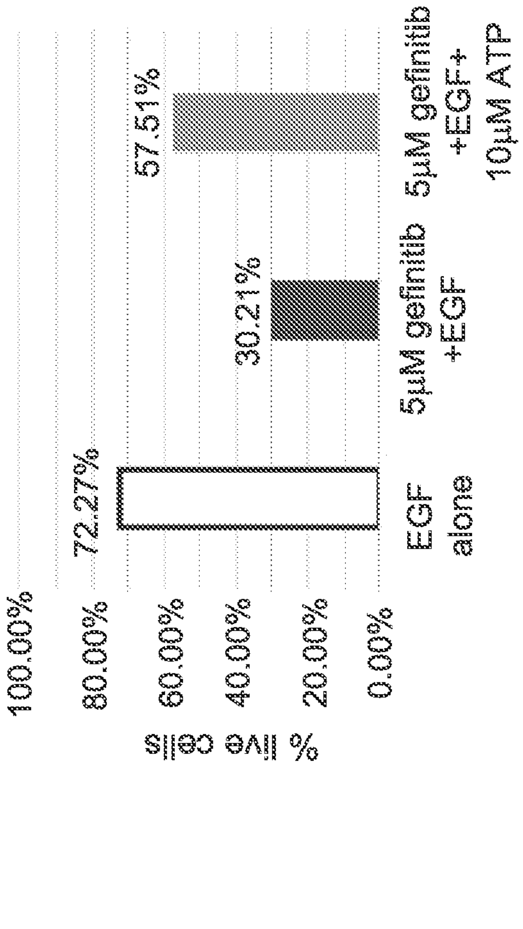

FIG. 8A-B depicts that ATP analogue increases p-EGFR expression on A431 cells treated with gefitinib. A431 cells were treated for 20 minutes with i) 150n/ml EGF. ii) EGF and 5 Um gefitinib and iii) EGF+gefitinib and 10 uM ATP analogue. The level of phosphorylated EGFR receptor was measured in A431 cells by flow cytometry. Activated levels of p-EGFR in A431 cells dropped from 72.27% to 30.21% when gefitinib was added. The ATP analogue was able to reverse the toxic effect of gefitinib on EGFR with p-EGFR levels rising to 57.51%.

In order to block the effect of the TKI's erlotinib and gefitinib (EGFR inhibitors) and trametinib (a selective and highly potent small molecular inhibitor of mitogen-activated extracellular signal-regulated kinase (MEK) inhibitor) on the keratinocytes, we tested a number of small molecules with an aniline moiety (termed in our experiments "sn" molecules) that can occupy the hydrophobic pocket of the ATPase thus blocking the TKI's binding to the ATPase.

Figure 9A:
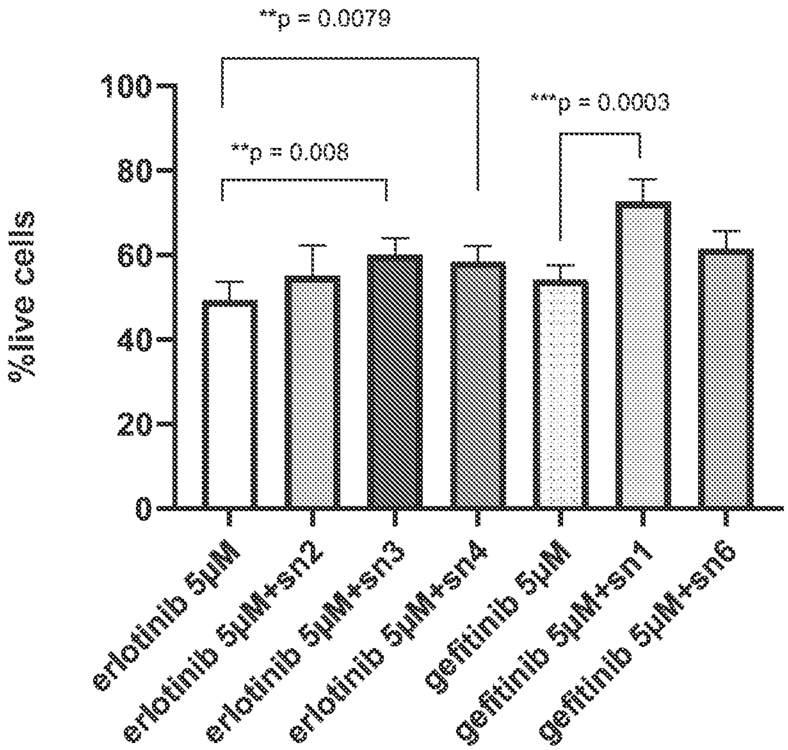
FIGS. 9A-B show the protective effect sn1-sn6 have on A431 cell treated with erlotinib or gefitinib using MTT FIGS. 10A-B demonstrate derivatives of G4 blocking the binding between cetuximab and EGFR.
Figure 9B:
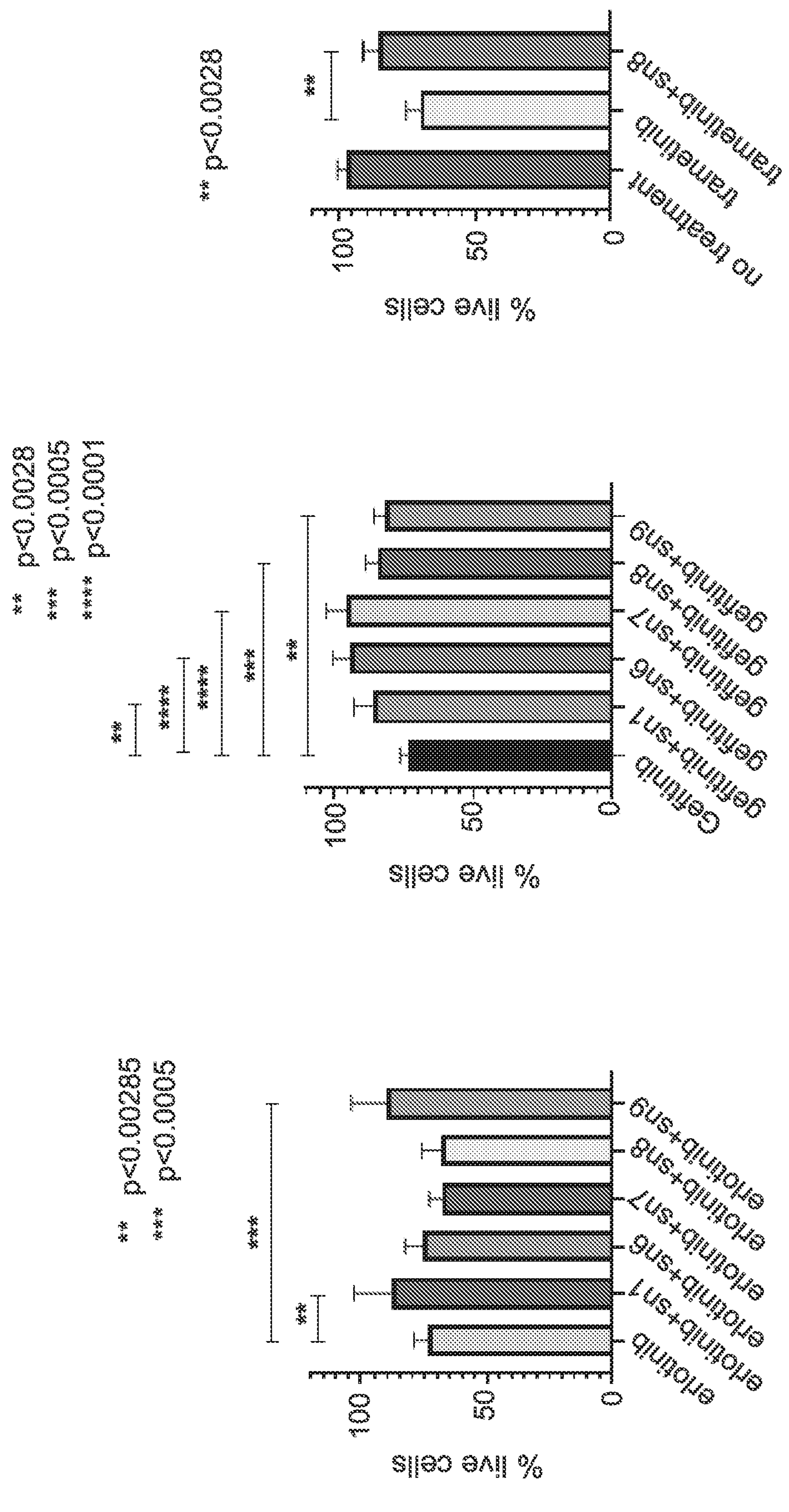
Figure 10A:
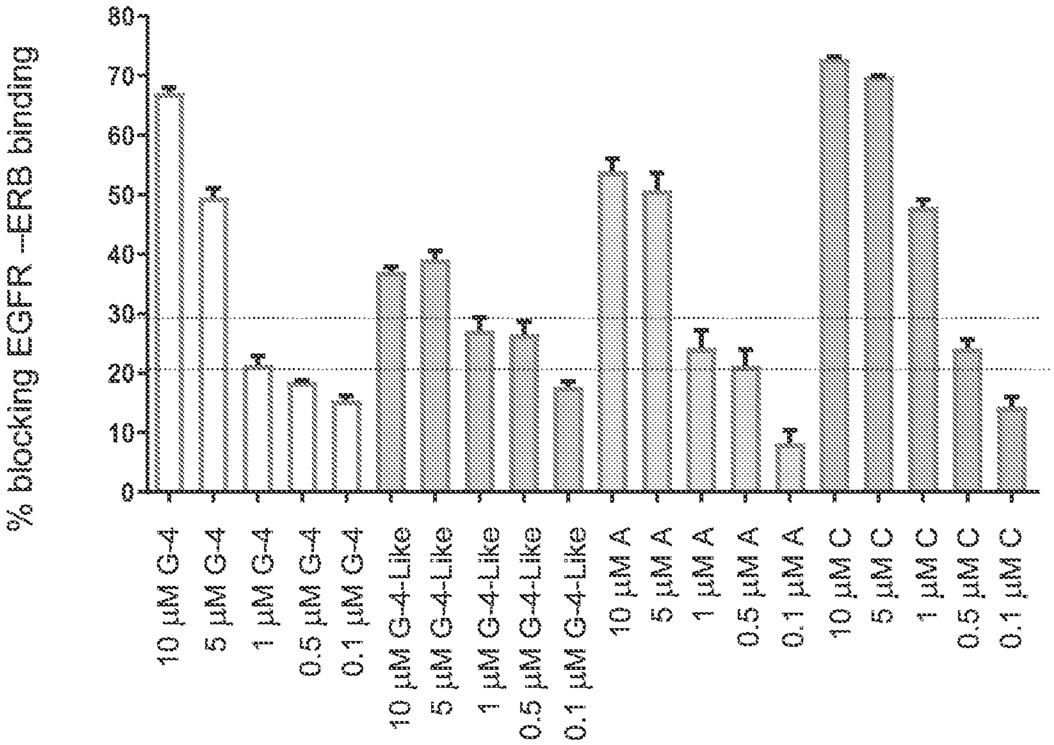
Figure 10B:
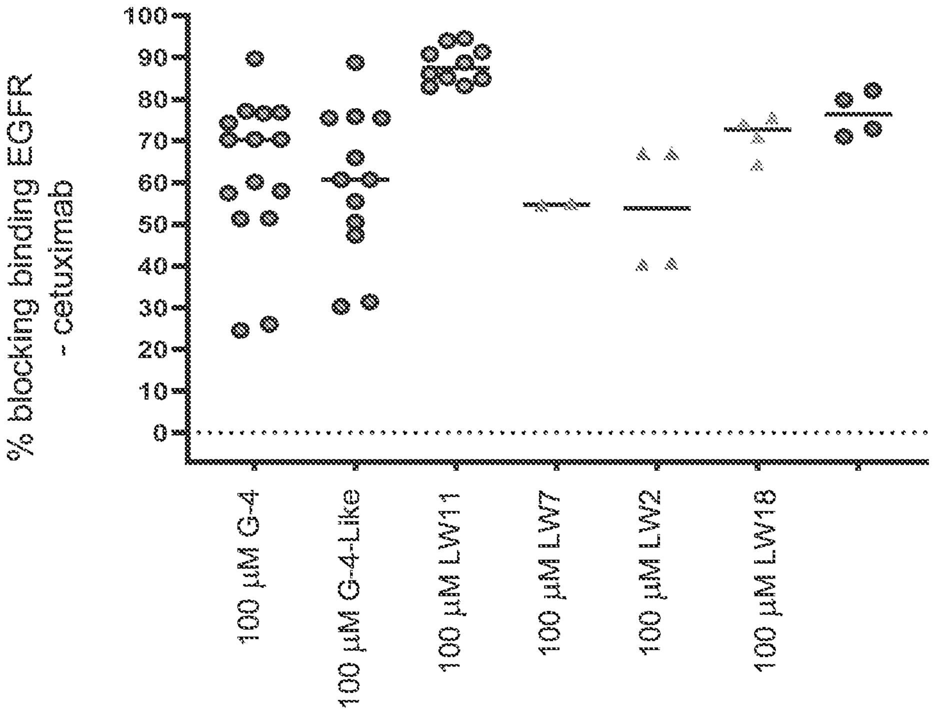

FIG. 9A shows the protective effect sn1-sn6 have on keratinocyte cell line treated with erlotinib or gefitinib using MTT—a colorimetric, non-radioactive assay for assessing cell viability and proliferation. FIG. 9B shows the improved percent live keratinocytes after adding sn1, sn6, sn7, sn8, sn9 to elotinib and gefitinib and improved percent survival of HaCaT keratinocytes when adding sn8 to trametinib FIG. 10A-B demonstrated blocking of cetuximab binding to EGFR by G4 similar compounds and derivatives.

Figure 16:
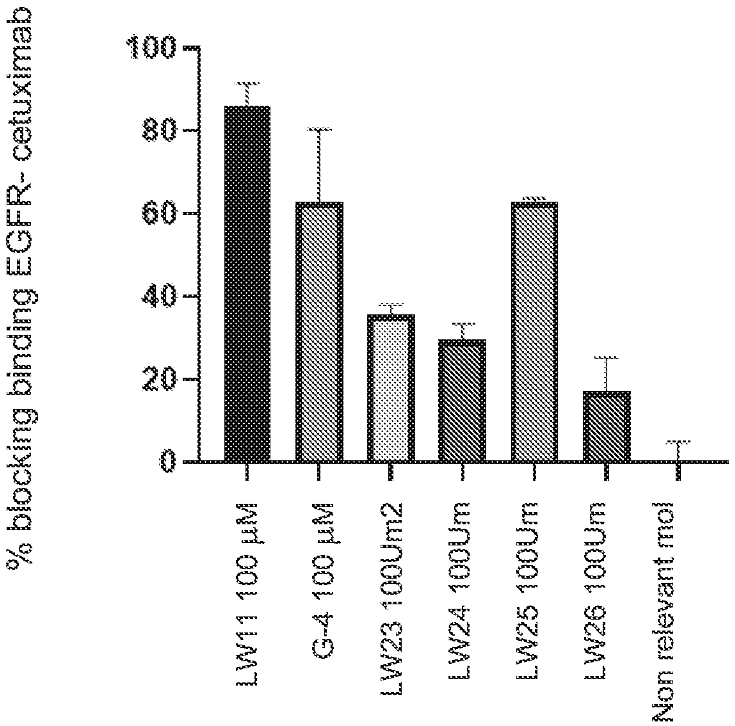
FIG. 16 shows LW molecules block cetuximab binding to EGFR.

Using an ELISA assay, compounds herein designated LW11, G4, LW23, LW24, LW25 and LW26 compounds all block cetuximab's binding to EGFR (FIG. 16).

Development of Topical Slow Release System

The inventors used biodegradable polymers to construct nanoparticles to penetrate the deeper layers of the skin, aiming to target the hair follicles which are rich in EGFR. The nanoparticles can be loaded with lipophilic molecules to be slowly released into the tissue and thus provide long term protection to the skin from the damage of systemic administration of the biological drug.

Figure 11A:
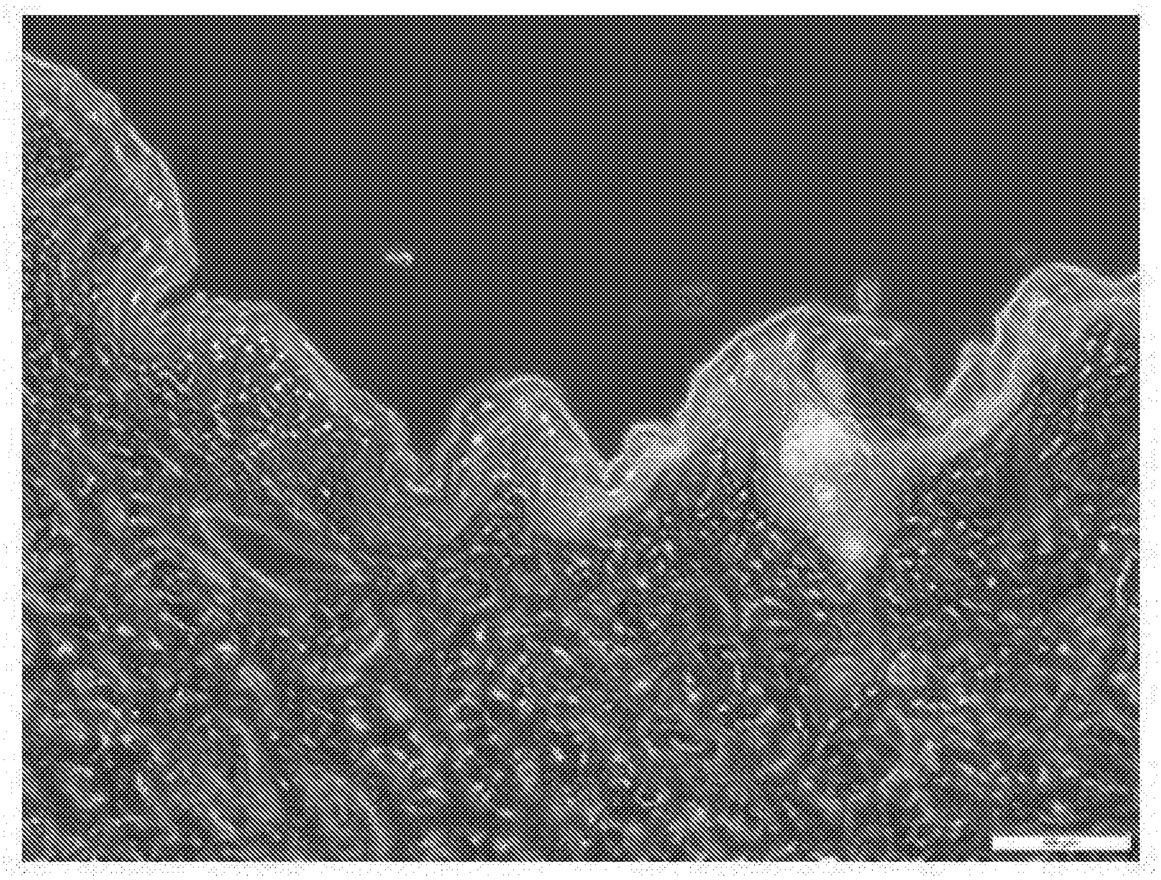
FIGS. 11A-B: A) Fluorescently labeled nanoparticles penetrating the acellular and cellular layers of the epidermis. B) Accumulation of fluorescently labeled nanoparticles in hair follicles and sebaceous glands in close proximity to EGFR.
Figure 11B:
Figure 12:
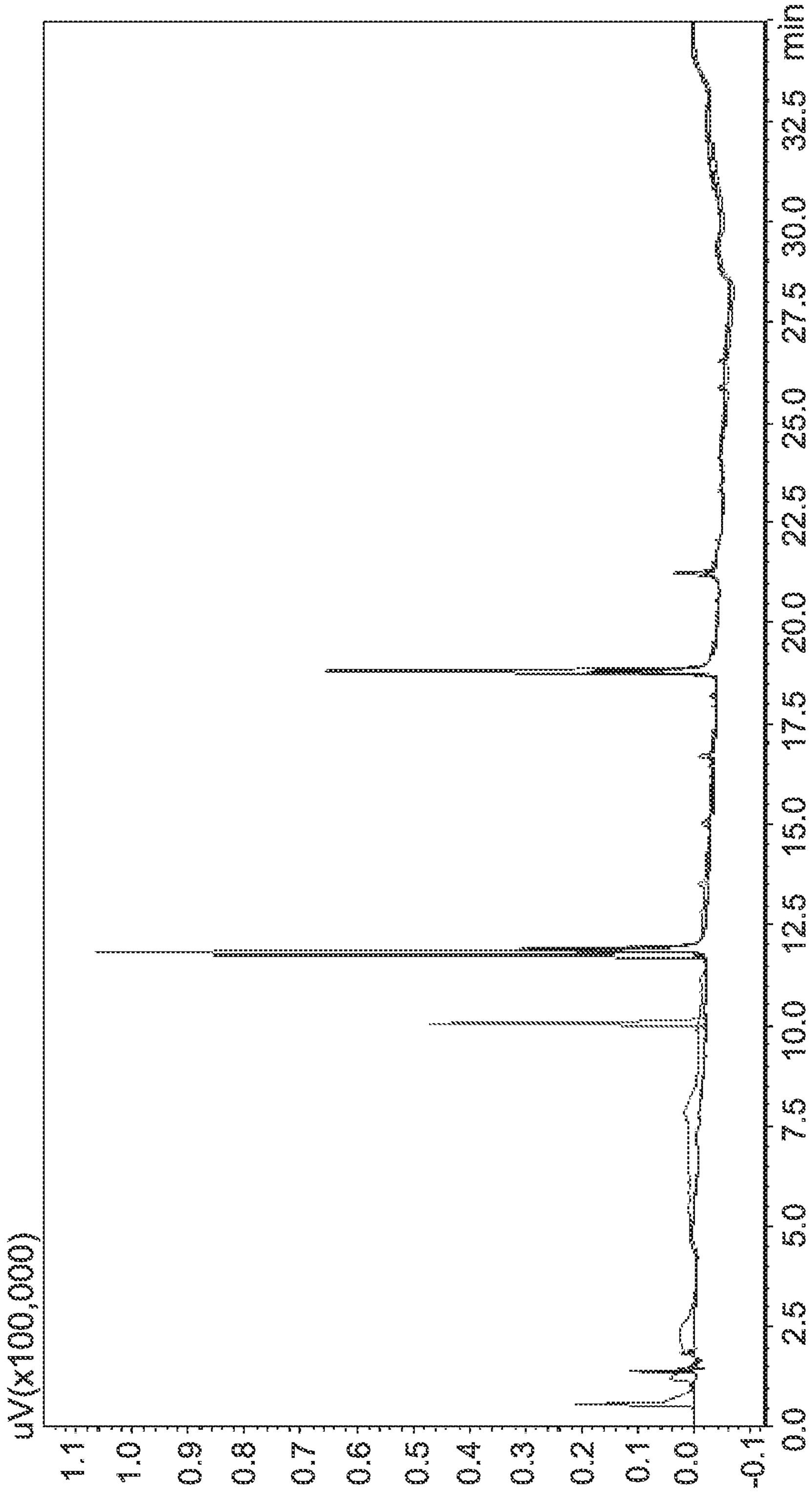
FIG. 12 demonstrates that G-4 compound does not penetrate full human skin as tested in Franz chamber.

The inventors designed and fabricated solidified polymer micelles composed of linear poly(L-lactide-co-glycolic acid)s (PEG-PLA) of ~20 nm, which was previously shown to have stability and ability to penetrate cells efficiently. FIG. 11A demonstrates that the nanoparticles can penetrate the epidermis and accumulate in the hair follicle and sebaceous glands, which are sites with a high concentration of EGFR demonstrates in FIG. 11B. using the Franz chamber the inventors demonstrated that G-4 does not penetrate full human skin as seen in FIG. 12.

Figure 13A:
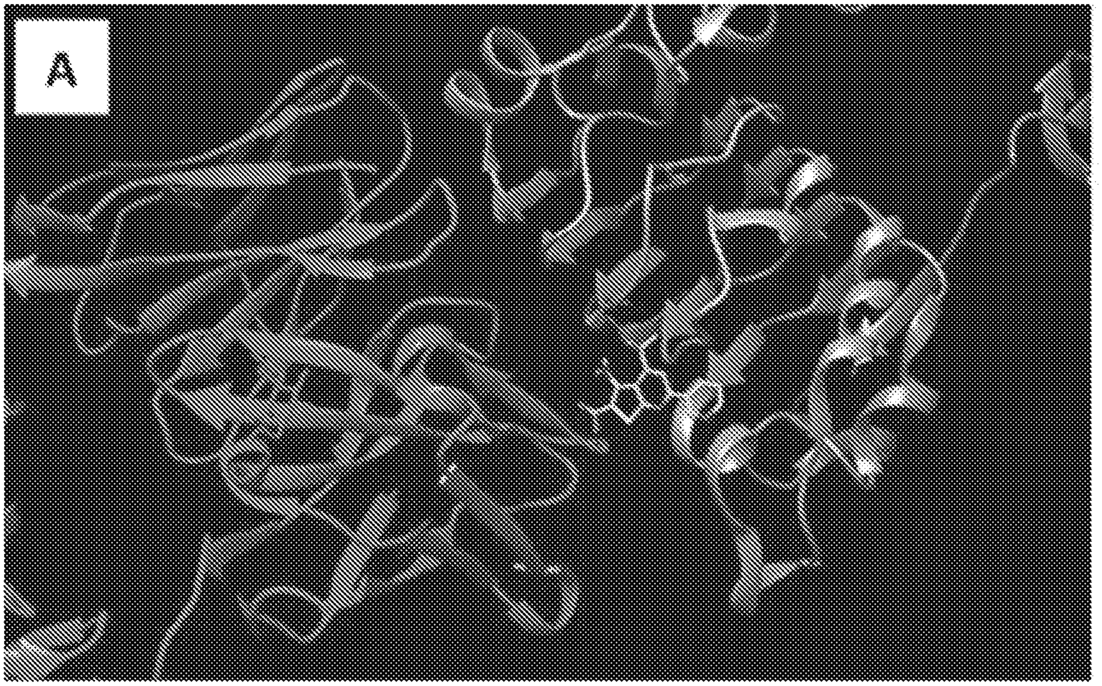
FIGS. 13A-B provides in silico docking hypothesis of G4 and LW11-EGFR interactions.
Figure 13B:
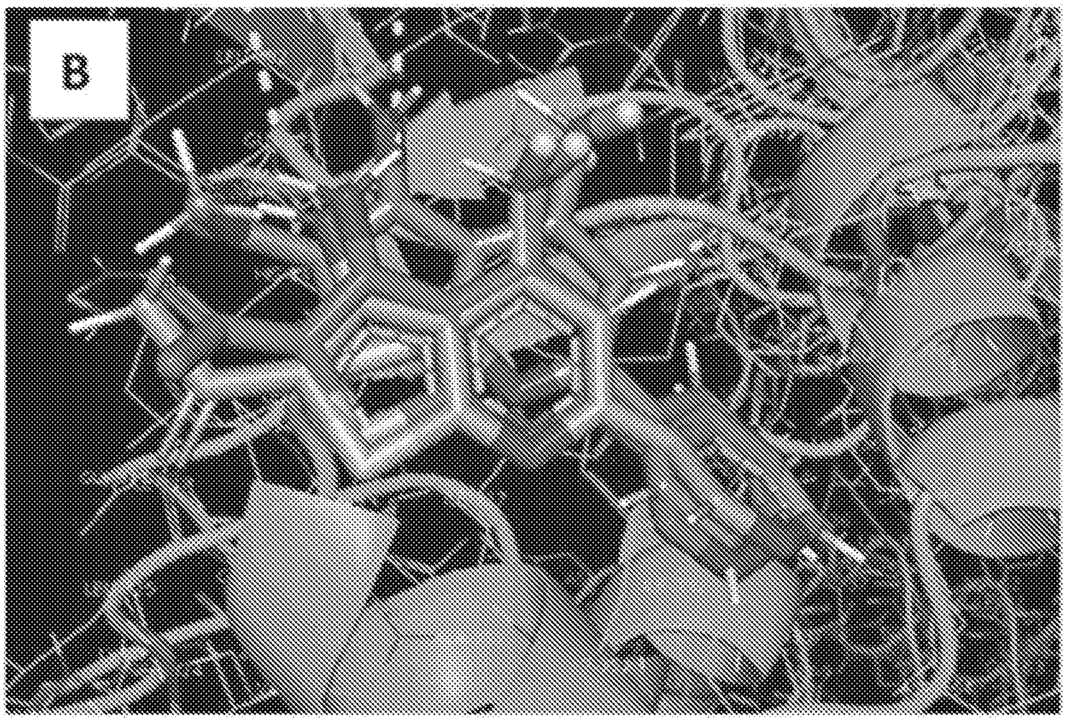

In silico docking hypothesis of G4 and LW11-EGFR interactions based on PDB: lyy9. Docking was performed using AutoDock Vina, AutoDock4, Swissdock and LeDock. The results were visualized by PyMol 2.3 and UCSF Chimera. FIG. 13A) The in silico docking model (Autodock Vina) illustrates the representative interacting surface between cetuximab (magenta) and EGFR (blue). In this model G4 interacts with EGFR adjacent to the cetuximab-EGFR binding site. FIG. 13B) shows all docking models used placed G4 at the same pocket interacting with EGFR.

Figure 14A:
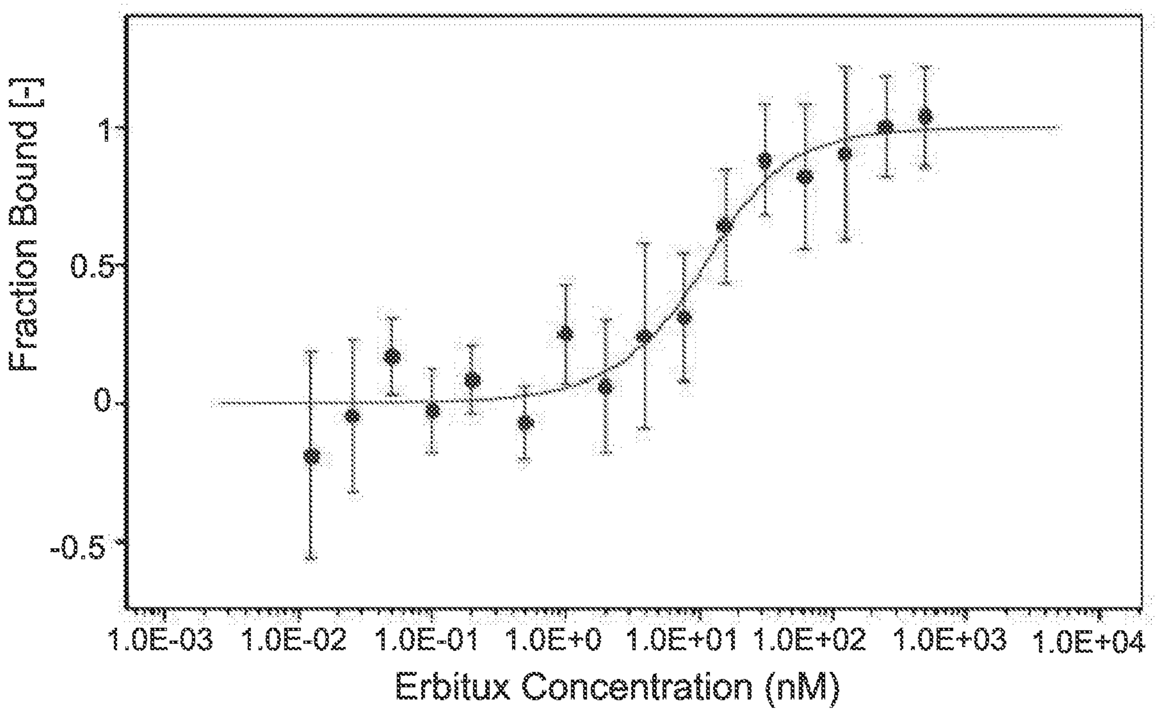
FIGS. 14 A-B provide Micro Scale Thermophoresis (MST) measurement of EGFR and LW11 interaction.
Figure 14B:
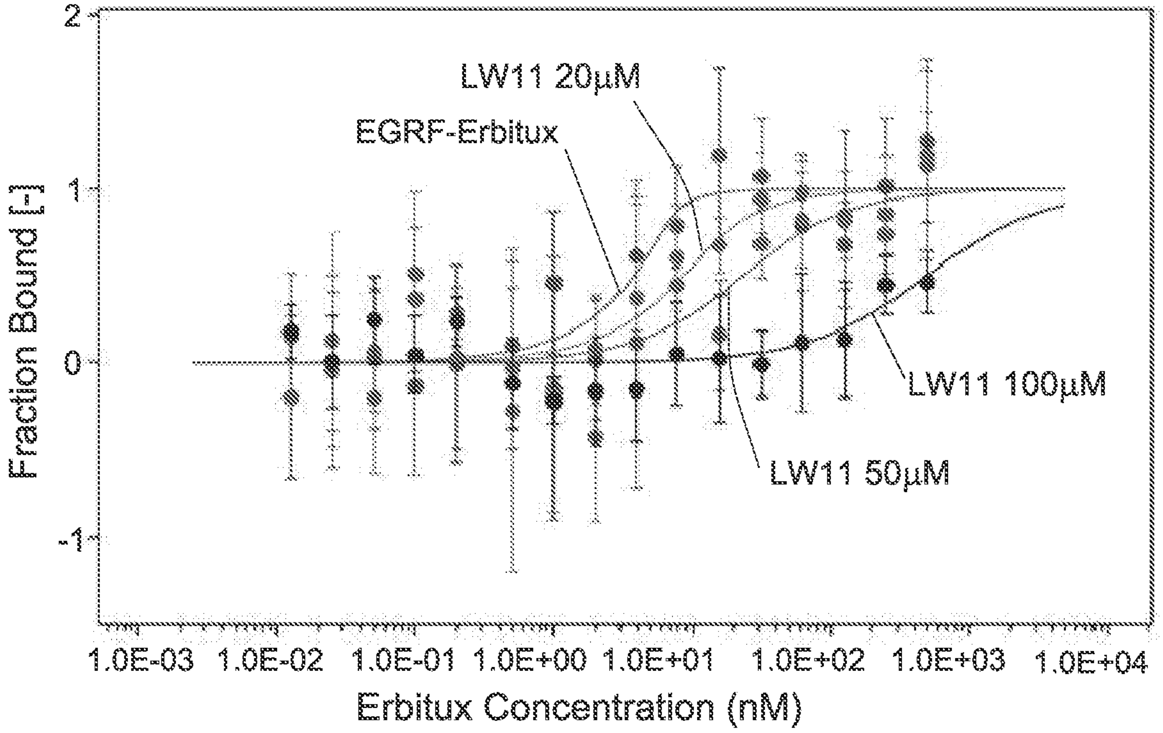

Micro Scale Thermophoresis (MST) measurement was used to examine the interaction between EGFR and LW11, FIG. 14A) A constant concentration of fluorescent EGFR (11.2 nM) with a titrated concentration of Erbitux from 500 nM down to 0.5 nM, demonstrate a binding profile with K_d=0.234±0.99 nM. (B) Addition of LW11 with increase concentration (20, 50 and 100 μM) inhibits Erbitux-EGFR binding and deflecting the curve slope to a higher Erbitux concentration and higher K_d values (3.04, 12.74, 489.86 nM respectively).

Development of Stable and Uniform Biodegradable Nanocarrier System

Figure 15A:
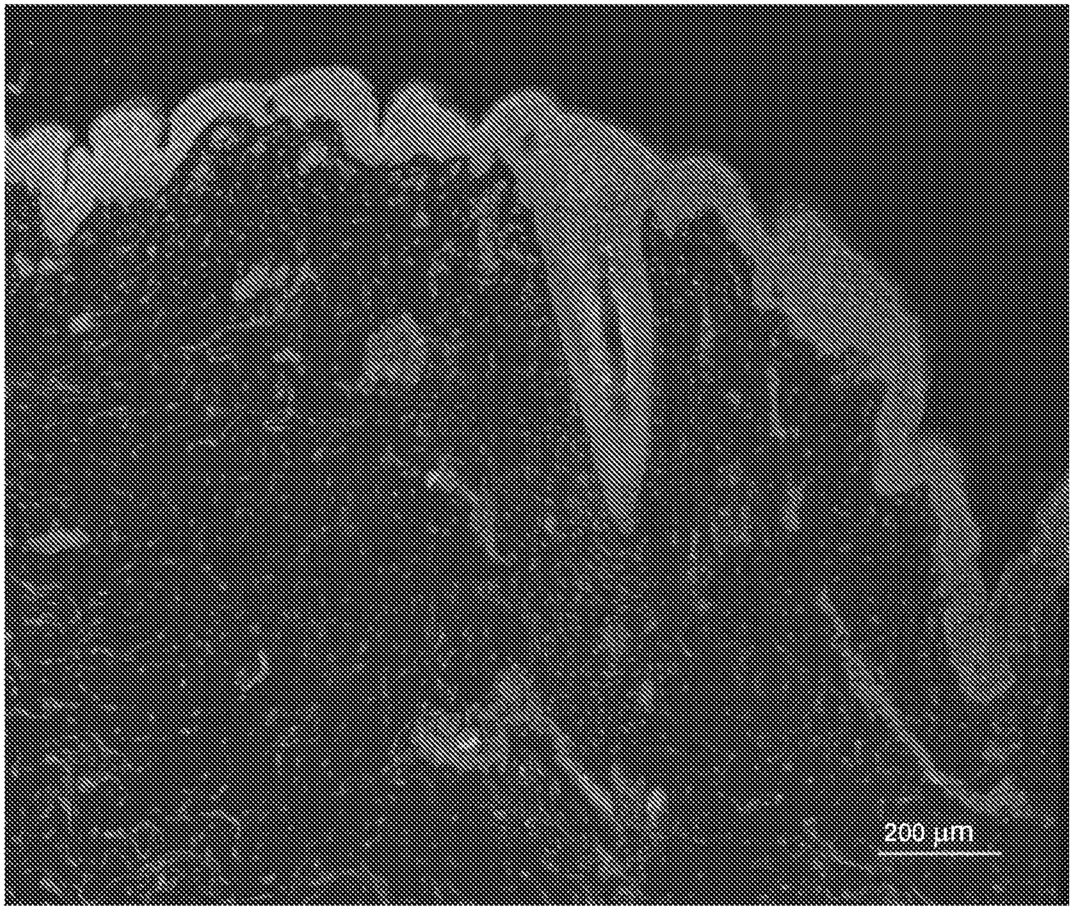
FIGS. 15A-B show NF-5 penetration into the hair follicles. Ex-vivo human skin modeling follicular penetration of NF-5 PLGA formulation loaded with 6-coumarin as a fluorescent drug model.
Figure 15B:
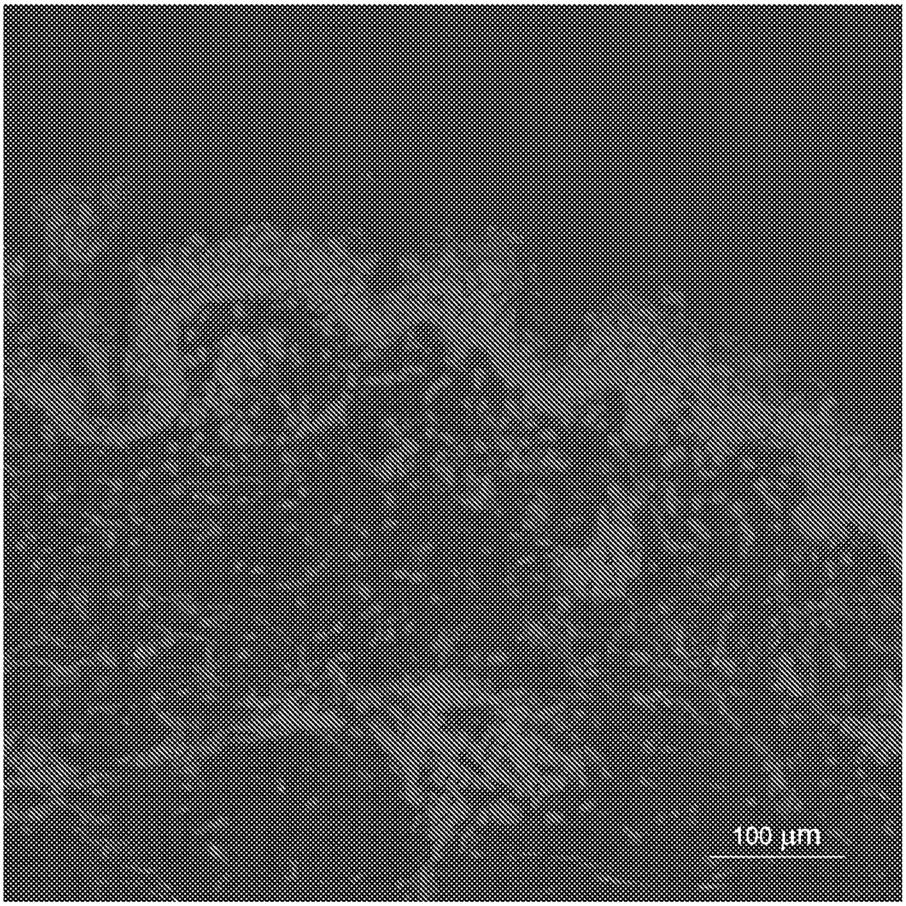

Fabrication of Poly-Lactic-co-Glycolic acid (PLGA) nanoparticles was done using nanoprecipitation/solvent displacement method. Many formulations have been fabricated during this process. The optimal formulation named NF-5 has been characterize with particles diameter of 104.7, poly dispersity index (PDI) of 0.06 which indicate on preparation homogeneity and Zeta potential of −23.6. NF-5 is serving the study for further aims. Results are summarized in Table 1. NF-5 was tested for follicular penetration and demonstrate effective penetration as demonstrated in FIG. 15.

Lead Compound Encapsulation and Release from Nanocarrier System

Evaluation of drug release from the nanocarriers has been performed using 6-coumarin as a drug model. In Table 1 the NF refers to formulation. the compound in this exp was 6 coumarin as a drug MODEL. Release test was done both in neutral and acidic pH (7.44, 5.0), modeling the varying pH in the skin layers. My findings show drug slow-release kinetics from the nanoparticles while no difference was observed between the neutral and the acidic pH. This suggest a successful slow-release biodegradable nanocarriers system that is not affected by the changing conditions of the skin barriers.

TABLE 1

| Formulation | Polymer | Surfactant in the organic phase (W/V %) | Surfactant aqueous phase (W/V %) | Mean diameter (nm) | Dispersion index | ZP (mV) | Remarks |
|---|---|---|---|---|---|---|---|
| NF-1 | PEG-PLA 1-2 kd | — | Soultol 0.1% | 944.7 | 0.6 | −17.3 | |
| NF-2 | PEG-PLA 1-2 kd | Tween 80 0.5% | Soultol 0.1% | 128.2 | 0.35 | NA | |
| NF-3 | PLGA 50:50 50 kd | Tween 80 0.5% | Soultol 0.1% | 77.16 | 0.09 | NA | |
| NF-4 | PLGA 50:50 50 kd | Tween 80 0.1% | Soultol 0.1% | 103.7 | 0.05 | −24.2 | |
| NF-5 | PLGA 50:50 50 kd | Tween 80 0.01% | Soultol 0.1% | 101.1 | 0.065 | −23.6 | |
| NF-6 | PLGA 75:25 50 kd | Tween 80 0.01% | Soultol 0.1% | 104.7 | 0.06 | NA | |
| NF-7 | PLGA 50:50 50 kd | Tween 80 0.01% | Soultol 0.5% | 98.27 | 0.13 | NA | Organic phase-Acetone |
| NF-8 | PLGA 50:50 50 kd | Tween 80 0.01% | Soultol 0.1% | 89.35 | 0.06 | −23.6 | Organic phase-Acetone |
| NF-9 | PLGA 50:50 50 kd | Tween 80 0.01% | Soultol 0.1% | 105.6 | 0.056 | −25.8 | Acidic terminal polymer |
| NF-10 | PLGA 50:50 50 kd | Tween 80 0.01% | Soultol 0.1% | 121.2 | 0.134 | −34.4 | Made by sonication |
| NF-11 | PLGA 50:50 50 kd | Tween 80 0.01% | PVA 0.2% | 1141 | 0.119 | NA | |
| NF-12 | PLGA 50:50 50 kd | Tween 80 0.01% | Pluronic acid 0.5% | 137 | 0.08 | NA | |
| NF-13 | PLGA 50:50 50 kd | Tween 80 0.01% | Pluronic acid 2% | 107 | 0.07 | −19.9 | |
| NF-14 | PLGA 50:50 50 kd | Tween 80 0.01% | Pluronic acid 0.01% | 114 | 0.06 | −29.8 | |
| NF-15 | PCL 14 kd | Tween 80 0.01% | Soultol 0.1% | 430 | 0.21 | | |
| NF-16 | PCL 80 kd | Tween 80 0.01% | Soultol 0.1% | 317 | 0.19 | | |

Biodegradable nanoparticles were prepared by using two different methods. The first method is solvent displacement. This method was based on changing the polymer from organic to aqueous conditions. The process lead to the formation of nanoparticles. Poly(D,L-lactide-co-glycolide) (PLGA) was used as an exemplary system.

Poly lactic-co-glycolic-acid (PLGA) with different ratio and molecular weight polymers was dissolved in acetonitrile (ACN) at a concentration of 0.6% w/v. The ACN solution contained Tween 80 as a stabilizing surfactant. In the next step, the polymer introduced into Solutol® HS 15 or Polyvinyl alcohol (PVA) or Pluronic acid in variant concentration. The ratio of the aqueous phase and the organic phase ratio was 1:2. The change in the surfactant type was done in order to achieve different particles size and Zeta potential.

Stirring of the two phases in a speed of 800 rpm using head stirrer for 15 min followed by vacuum evaporation (Basis HeiVAP, Heidolph instrument, Germany) was done in order to separate the dispersed particles in the aqueous phase from the ACN.

For small nanoparticles (~20 nm) the solvent displacement method was done using a dialysis bag for the solvents exchanging. Briefly, Poly(Ethylene-Glycol)-Poly(Lactic-acid) (PEG-PLA) polymer with average molecular weight of 1-2kd dissolved with the loaded drug in DMSO and placed in a dialysis bag (MCWO:1kD, SpectumLabs). The dialysis bag placed in a 2 L cup under stirring, and water exchanged three times in gapes of 2 hr. Particles have been formed during the solvents exchange.

According to our findings, we choose to work with the NF-5 formulation due to its capability to penetrate and accumulate in the hair follicles, particles uniformity and stability, and drug release profile of slow release kinetics.

The invention claimed is:

1. A method for interrupting binding of cetuximab to epidermal growth factor receptor (EGFR) in a skin region, the method comprising administering to the skin region at least one material prior to, concomitantly with or following systemic administration of the cetuximab, to thereby interrupt binding of the systemically administered cetuximab to EGFR in the skin region, wherein the at least one material is:

LW11

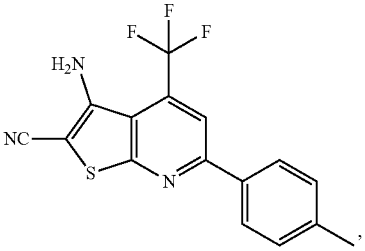

,

G4

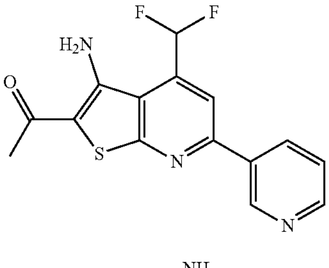

,

LW23

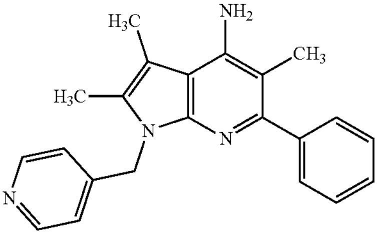

,

-continued

LW24

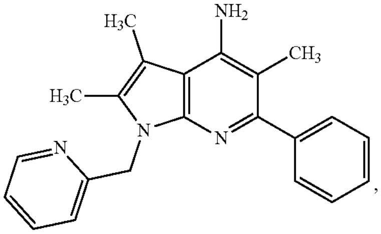

,

LW25

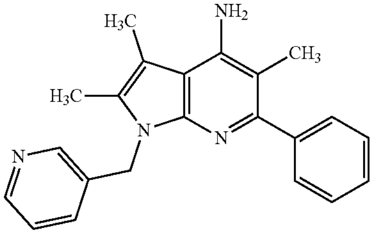

, or

LW26

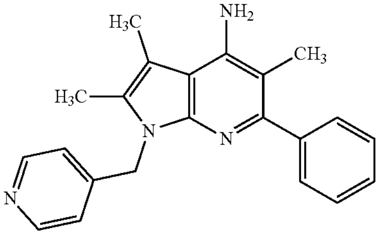

.

2. The method according to claim 1, wherein the at least one material administered to the skin region is provided in a nanoparticulate or microparticulate form.

3. The method according to claim 2, wherein the at least one material administered to the skin region is carried in a carrier selected from nanocapsules, nano-carriers, nanoparticles, microcapsules, micro-carriers and microparticles.

4. The method according to claim 1, wherein the at least one material administered to the skin region is

LW11

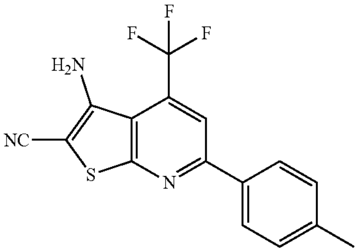

or

G4

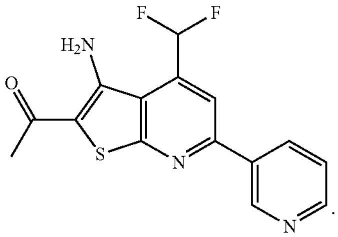

.

* * * * *